US012686708B2

(12) United States Patent
Linnemann et al.

(10) Patent No.: US 12,686,708 B2
(45) Date of Patent: Jul. 21, 2026

(54) PEPTIDE MARKERS TO TRACK GENETICALLY ENGINEERED CELLS

(71) Applicant: NEOGENE THERAPEUTICS B.V., Amsterdam (NL)

(72) Inventors: Carsten Linnemann, Amsterdam (NL); Thomas Kuilman, Amstelveen (NL); Gavin M. Bendle, Amsterdam (NL); Jeroen W.J. van Heijst, Amstelveen (NL); Xiangjun Kong, Amsterdam (NL); Loek Josephus Eggermont, The Hague (NL)

(73) Assignee: NEOGENE THERAPEUTICS B.V., Amsterdam (NL)

( * ) Notice: Subject to any disclaimer, the term of this patent is extended or adjusted under 35 U.S.C. 154(b) by 1245 days.

(21) Appl. No.: 17/557,514

(22) Filed: Dec. 21, 2021

(65) Prior Publication Data

US 2022/0195006 A1      Jun. 23, 2022

Related U.S. Application Data

(60) Provisional application No. 63/170,196, filed on Apr. 2, 2021, provisional application No. 63/129,480, filed on Dec. 22, 2020.

(51) Int. Cl.

| | |
|---|---|
| *C07K 14/705* | (2006.01) |
| *A61K 40/11* | (2025.01) |
| *A61K 40/31* | (2025.01) |
| *A61K 40/32* | (2025.01) |
| *A61K 40/42* | (2025.01) |
| *A61K 47/68* | (2017.01) |
| *C12N 5/0783* | (2010.01) |
| *C12N 15/90* | (2006.01) |

(52) U.S. Cl.
CPC .......... *C07K 14/7051* (2013.01); *A61K 40/11* (2025.01); *A61K 40/31* (2025.01); *A61K 40/32* (2025.01); *A61K 40/4211* (2025.01); *A61K 40/4269* (2025.01); *A61K 47/6813* (2017.08); *A61K 47/6849* (2017.08); *C12N 5/0636* (2013.01); *C12N 15/90* (2013.01); *A61K 2239/57* (2023.05)

(58) Field of Classification Search
CPC ............ C07K 14/7051; C07K 2317/52; C07K 16/2809; C07K 16/2803; C07K 2319/33; C07K 2319/41; C07K 2319/42; C07K 2319/43; C07K 2319/40; A61K 40/11; A61K 40/31; A61K 40/32; A61K 40/4211; A61K 40/4269; A61K 47/6813; A61K 47/6849; A61K 2239/57; A61K 2039/505; A61K 35/17; C12N 5/0636; C12N 15/90; C12N 2510/00; G01N 33/505; G01N 33/56972; A61P 35/00
See application file for complete search history.

(56) References Cited

U.S. PATENT DOCUMENTS

2018/0000913 A1      1/2018   Hacohen et al.

FOREIGN PATENT DOCUMENTS

| | | |
|---|---|---|
| WO | WO 2008/006458 | 1/2008 |
| WO | WO 2014/043441 A1 | 3/2014 |
| WO | WO 2016/079333 | 5/2016 |
| WO | WO 2018/102795 | 6/2018 |
| WO | WO 2020/204527 | 10/2020 |
| WO | WO 2021/011482 | 1/2021 |
| WO | WO 2022/140774 | 6/2022 |

OTHER PUBLICATIONS

Sommermeyer et al. J Immunol (2010) 184 (11): 6223-6231) (Year: 2010).*
Wang et al. The EMBO Journal (1998) 17: 10-26 (Year: 1998).*
Zhang et al. iScience. Nov. 20, 2020;23(12):101828 (Year: 2020).*
Sommermeyer. J Immunol (2010) 184 (11): 6223-6231 (Year: 2010).*
Linnemann et al., "High-throughput identification of antigen-specific TCRs by TCR gene capture", Nature Medicine, vol. 19, No. 11, Nov. 2013, in 10 pages.
Ludwig et al., "High-throughput single-cell sequencing of paired TCRα and TCRβ genes for the direct expression-cloning and functional analysis of murine T-cell receptors", Eur. J. Immunol., 2019, vol. 49, pp. 1269-1277.
Rydzek et al., "Chimeric Antigen Receptor Library Screening Using a Novel NF-KB/NFAT Reporter Cell Platform", Molecular Therapy, vol. 27, No. 2, Feb. 2019, pp. 287-299.
International Search Report and Written Opinion mailed Nov. 5, 2020, in International Application No. PCT/US2020/041824, in 22 pages.
International Search Report and Written Opinion in International Application No. PCT/US2021/073057, mailed on May 31, 2022, in 21 pages.

* cited by examiner

*Primary Examiner* — Sean E Aeder
*Assistant Examiner* — Yie Chia Lee
(74) *Attorney, Agent, or Firm* — KNOBBE, MARTENS, OLSON & BEAR, LLP

(57)      ABSTRACT

To allow control over injected genetically engineered cells, it is helpful that the genetically engineered cells express a marker that can be used to detect such cells among a pool of unmodified cells. Some embodiments relate to a marked protein comprising a TCR constant domain and an exogenous amino acid variation that comprises a sequence that is detectable and identifiable within the TCR constant domain. Other embodiments relate to an antibody epitope that is attached to a TCR chain. Both the marked proteins and the antibody epitopes can be used to track genetically engineered cells.

22 Claims, 30 Drawing Sheets

Specification includes a Sequence Listing.

Figure 1. Diagram of TCR constant domain epitope.
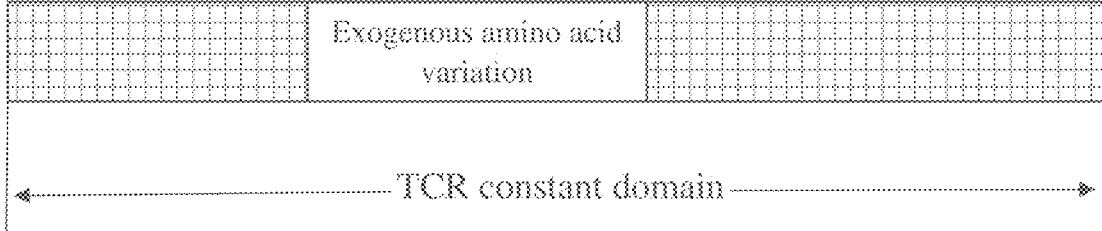

Figure 2A. Diagram of an antibody epitope where the antibody epitope is attached to the C-terminal a TCR chain.

| TCR chain | antibody epitope |
|-----------|------------------|

Figure 2B. Diagram of an antibody epitope where the antibody epitope is attached to the N-terminal of a TCR chain.

| antibody epitope | TCR chain |
|------------------|-----------|

Figure 2C. Diagram of an antibody epitope where the antibody epitope is inserted into a TCR chain.

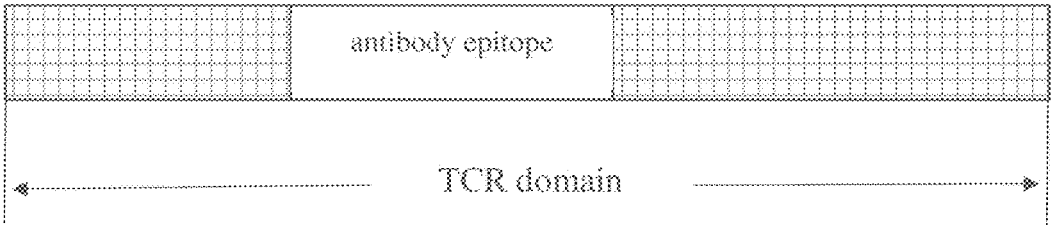

Figure 2D. Diagram of an antibody epitope where the antibody epitope is used to connect TCRα and TCRβ chains. The positions of TCRα and TCRβ chains can be switched.

| TCRα chain | antibody epitope | TCRβ chain |
|------------|------------------|------------|

Figure 5:
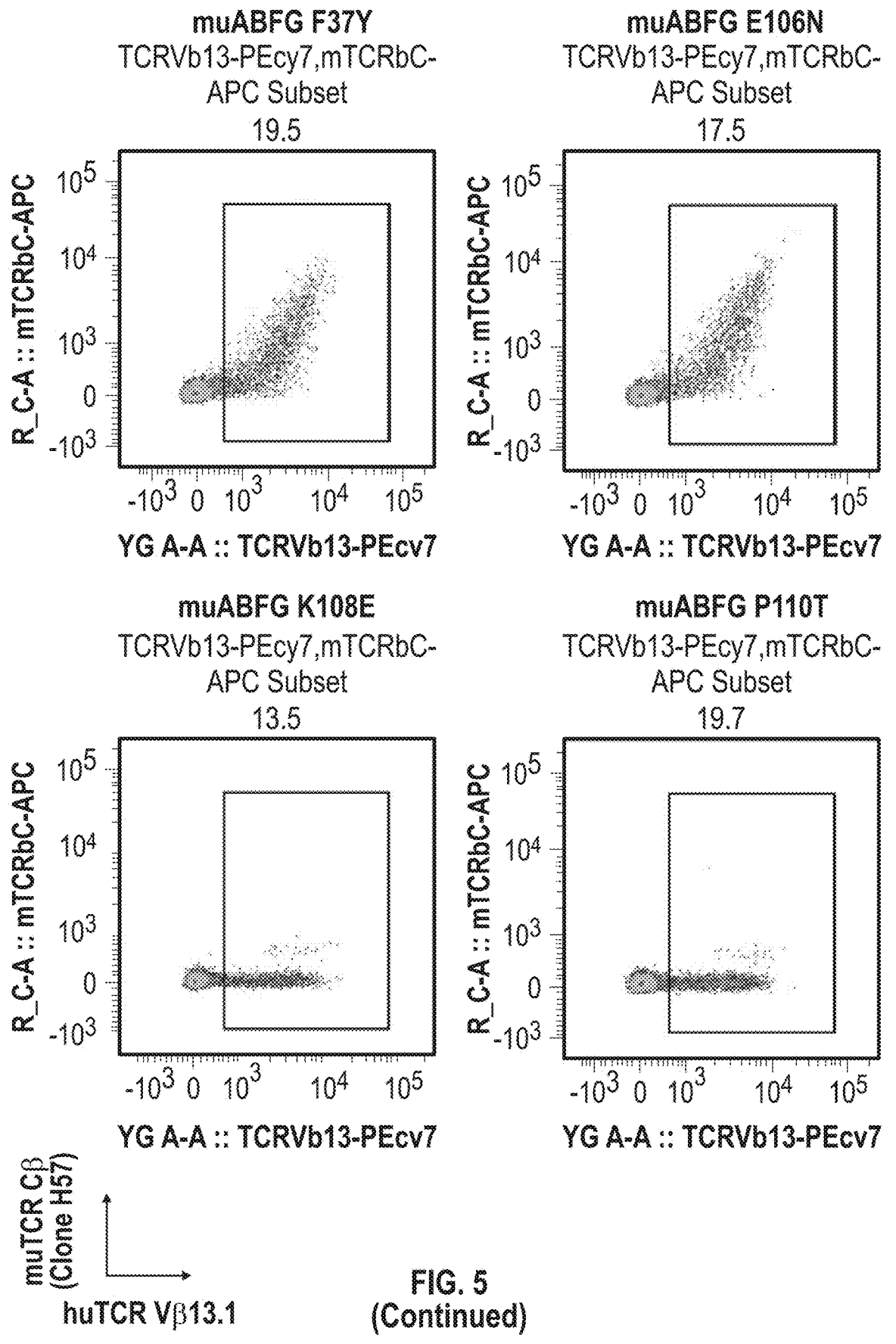

FIG. 5 muABFG F37Y
TCRVb13-PEcy7,mTCRbC-
APC Subset
19.5 muABFG E106N
TCRVb13-PEcy7,mTCRbC-
APC Subset
17.5 muABFG K108E
TCRVb13-PEcy7,mTCRbC-
APC Subset
13.5 muABFG P110T
TCRVb13-PEcy7,mTCRbC-
APC Subset
19.7

YG A-A :: TCRVb13-PEcv7 muTCR Cβ (Clone H57)

huTCR Vβ13.1

Figure 10. Immunogen used to raise 2A peptide antibody 3H4 (SEQ ID NO: 1)

CGDVEENPG

Figure 11. T2A peptide sequence (SEQ ID NO: 2)

EGRGSLLTCGDVEENPGP

Figure 12. P2A peptide sequence (SEQ ID NO: 3)

ATNFSLLKQAGDVEENPGP

Figure 13. Human TCR Cβ2 domain containing the murine TCR epitope detectable by the H57 antibody (SEQ ID NO: 4)

XDLRNVFPPKVAVFEPSEAEISHTQKATLVCLATGFYPDHVELSWWVNG
    KEVHSGVSTDPQPLKEQPALNDSRYCLSSRLRVSATFWQNPRNHFRCQV
    QFYGLSENDKWPEGSAKPVTQIVSAEAWGRADCGFTSESYQQGVLSATIL
    YEILLGKATLYAVLVSALVLMAMVKRKDSRG

Figure 14. Human TCR Cβ2 domain linked to the T2A peptide epitope detectable by the 3H4 antibody (SEQ ID NO: 5)

XDLKNVFPPKVAVFEPSEAEISHTQKATLVCLATGFYPDHVELSWWVNG
    KEVHSGVSTDPQPLKEQPALNDSRYCLSSRLRVSATFWQNPRNHFRCQV
    QFYGLSENDEWTQDRAKPVTQIVSAEAWGRADCGFTSESYQQGVLSATI
    LYEILLGKATLYAVLVSALVLMAMVKRKDSRGGSGEGRGSLLTCGDVEE
    NPGP

Figure 15. A fragment of a T2A or P2A peptide sequence (SEQ ID NO: 6)

GDVEENPG

Figure 16. A fragment of a E2A or F2A peptide sequence (SEQ ID NO: 7)

GDVESNPG

Figure 17. Human TCR Cβ2 domain (SEQ ID NO: 8)

XDLKNVFPPKVAVFEPSEAEISHTQKATLVCLATGFYPDHVELSWWVNG
KEVHSGVSTDPQPLKEQPALNDSRYCLSSRLRVSATFWQNPRNHFRCQV
QFYGLSENDEWTQDRAKPVTQIVSAEAWGRADCGFTSESYQQGVLSATI
LYEILLGKATLYAVLVSALVLMAMVKRKDSRG

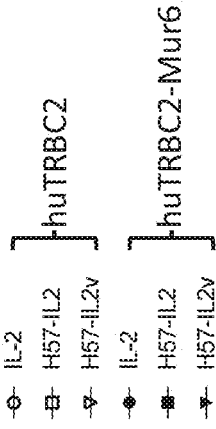
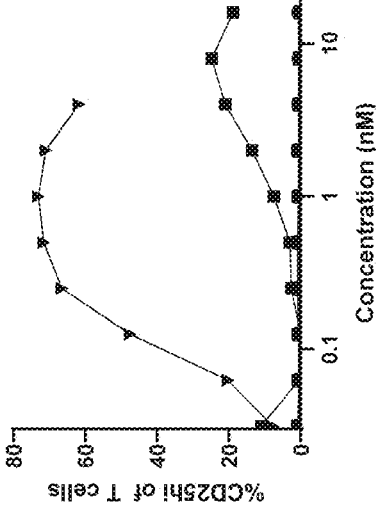
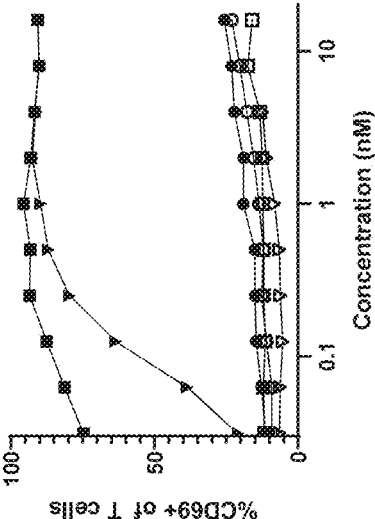
Fig. 22

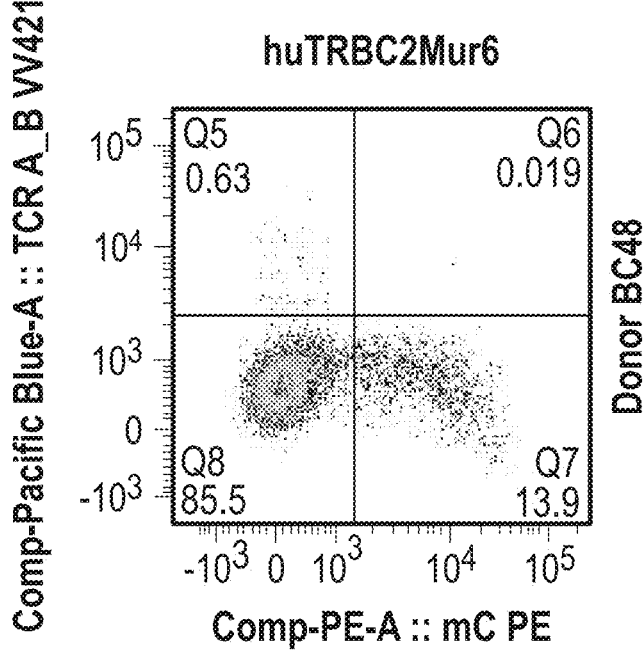
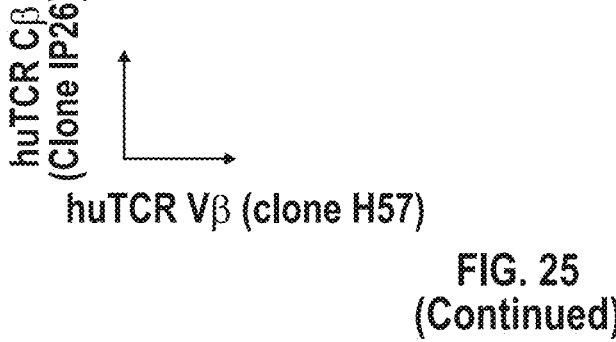
FIG. 25
(Continued)

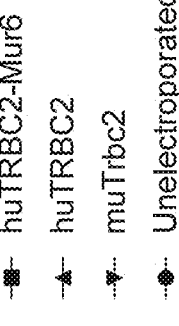
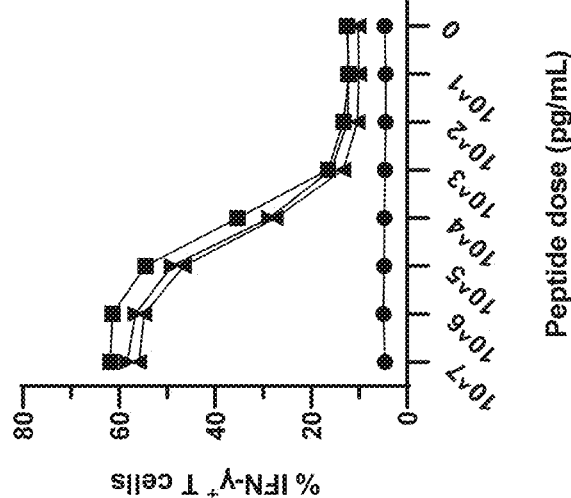
Fig. 26A

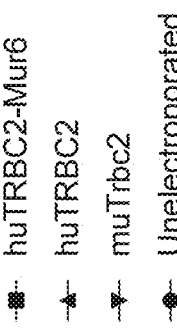
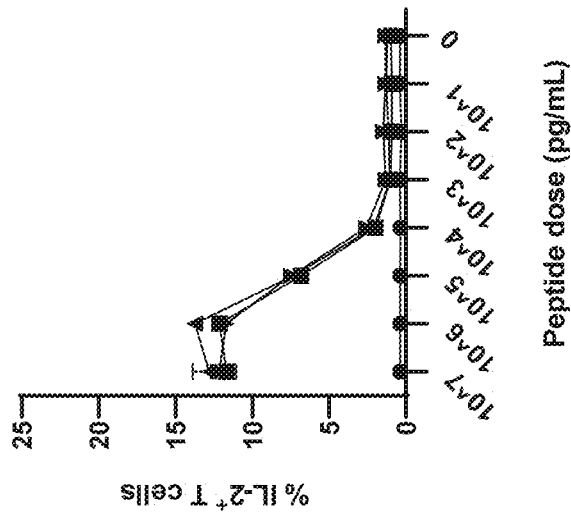
Fig. 26C

SEQUENCE LISTING

```
<160> NUMBER OF SEQ ID NOS: 40

<210> SEQ ID NO 1
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1

Cys Gly Asp Val Glu Glu Asn Pro Gly
1               5

<210> SEQ ID NO 2
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 2

Glu Gly Arg Gly Ser Leu Leu Thr Cys Gly Asp Val Glu Glu Asn Pro
1               5                   10                  15

Gly Pro

<210> SEQ ID NO 3
<211> LENGTH: 19
<212> TYPE: PRT
<213> ORGANISM: Artificial Sequence
<220> FEATURE:
<223> OTHER INFORMATION: Synthetic Polypeptide
```

<400> SEQUENCE: 3

Ala Thr Asn Phe Ser Leu Leu Lys Gln Ala Gly Asp Val Glu Glu Asn
1               5                   10                  15

Pro Gly Pro

<210> SEQ ID NO 4
<211> LENGTH: 179
<212> TYPE: PRT
<213> ORGANISM: Artificial Sequence
<220> FEATURE:
<223> OTHER INFORMATION: Synthetic Polypeptide
<220> FEATURE:
<221> NAME/KEY: VARIANT
<222> LOCATION: (1)...(1)
<223> OTHER INFORMATION: Xaa is any natural amino acid

<400> SEQUENCE: 4

Xaa Asp Leu Arg Asn Val Phe Pro Pro Lys Val Ala Val Phe Glu Pro
1               5                   10                  15

Ser Glu Ala Glu Ile Ser His Thr Gln Lys Ala Thr Leu Val Cys Leu
                20                  25                  30

Ala Thr Gly Phe Tyr Pro Asp His Val Glu Leu Ser Trp Trp Val Asn
            35                  40                  45

Gly Lys Glu Val His Ser Gly Val Ser Thr Asp Pro Gln Pro Leu Lys
        50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Lys Trp Pro Glu Gly
            100                 105                 110

Ser Ala Lys Pro Val Thr Gln Ile Val Ser Ala Glu Ala Trp Gly Arg
        115                 120                 125

Ala Asp Cys Gly Phe Thr Ser Glu Ser Tyr Gln Gln Gly Val Leu Ser
        130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly

<210> SEQ ID NO 5
<211> LENGTH: 200
<212> TYPE: PRT
<213> ORGANISM: Artificial Sequence
<220> FEATURE:
<223> OTHER INFORMATION: Synthetic Polypeptide
<220> FEATURE:
<221> NAME/KEY: VARIANT
<222> LOCATION: (1)...(1)
<223> OTHER INFORMATION: Xaa is any natural amino acid

<400> SEQUENCE: 5

Xaa Asp Leu Lys Asn Val Phe Pro Pro Lys Val Ala Val Phe Glu Pro
1               5                   10                  15

Ser Glu Ala Glu Ile Ser His Thr Gln Lys Ala Thr Leu Val Cys Leu
                20                  25                  30

Ala Thr Gly Phe Tyr Pro Asp His Val Glu Leu Ser Trp Trp Val Asn
            35                  40                  45

-continued

```
Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
                100                 105                 110

Arg Ala Lys Pro Val Thr Gln Ile Val Ser Ala Glu Ala Trp Gly Arg
            115                 120                 125

Ala Asp Cys Gly Phe Thr Ser Glu Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly Gly Ser Gly Glu Gly Arg Gly Ser Leu Leu Thr Cys Gly
                180                 185                 190

Asp Val Glu Glu Asn Pro Gly Pro
        195                 200
```

```
<210> SEQ ID NO 6
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 6

Gly Asp Val Glu Glu Asn Pro Gly
1               5
```

```
<210> SEQ ID NO 7
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 7

Gly Asp Val Glu Ser Asn Pro Gly
1               5
```

```
<210> SEQ ID NO 8
<211> LENGTH: 179
<212> TYPE: PRT
<213> ORGANISM: Artificial Sequence
<220> FEATURE:
<223> OTHER INFORMATION: Synthetic Polypeptide
<220> FEATURE:
<221> NAME/KEY: VARIANT
<222> LOCATION: (1)...(1)
<223> OTHER INFORMATION: Xaa is any natural amino acid

<400> SEQUENCE: 8

Xaa Asp Leu Lys Asn Val Phe Pro Pro Lys Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Tyr Pro Asp His Val Glu Leu Ser Trp Trp Val Asn
        35                  40                  45
```

-continued

```
Gly Lys Glu Val His Ser Gly Val Ser Thr Asp Pro Gln Pro Leu Lys
    50              55              60

Glu Gln Pro Ala Leu Asn Asp Ser Arg Tyr Cys Leu Ser Ser Arg Leu
65              70              75              80

Arg Val Ser Ala Thr Phe Trp Gln Asn Pro Arg Asn His Phe Arg Cys
                85              90              95

Gln Val Gln Phe Tyr Gly Leu Ser Glu Asn Asp Glu Trp Thr Gln Asp
            100             105             110

Arg Ala Lys Pro Val Thr Gln Ile Val Ser Ala Glu Ala Trp Gly Arg
        115             120             125

Ala Asp Cys Gly Phe Thr Ser Glu Ser Tyr Gln Gln Gly Val Leu Ser
    130             135             140

Ala Thr Ile Leu Tyr Glu Ile Leu Leu Gly Lys Ala Thr Leu Tyr Ala
145             150             155             160

Val Leu Val Ser Ala Leu Val Leu Met Ala Met Val Lys Arg Lys Asp
            165             170             175

Ser Arg Gly

<210> SEQ ID NO 9
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 9

Gln Cys Thr Asn Tyr Ala Leu Leu Lys Leu Ala Gly Asp Val Glu Ser
1               5               10              15

Asn Pro Gly Pro
            20

<210> SEQ ID NO 10
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 10

Val Lys Gln Thr Leu Asn Phe Asp Leu Leu Lys Leu Ala Gly Asp Val
1               5               10              15

Glu Ser Asn Pro Gly Pro
            20

<210> SEQ ID NO 11
<211> LENGTH: 177
<212> TYPE: PRT
<213> ORGANISM: Artificial Sequence
<220> FEATURE:
<223> OTHER INFORMATION: Synthetic Polypeptide
<220> FEATURE:
<221> NAME/KEY: VARIANT
<222> LOCATION: (1)...(1)
<223> OTHER INFORMATION: Xaa is any natural amino acid

<400> SEQUENCE: 11

Xaa Asp Leu Asn Lys Val Phe Pro Pro Glu Val Ala Val Phe Glu Pro
1               5               10              15

Ser Glu Ala Glu Ile Ser His Thr Gln Lys Ala Thr Leu Val Cys Leu
            20              25              30
```

```
Ala Thr Gly Phe Phe Pro Asp His Val Glu Leu Ser Trp Trp Val Asn
        35              40              45

Gly Lys Glu Val His Ser Gly Val Ser Thr Asp Pro Gln Pro Leu Lys
    50              55              60

Glu Gln Pro Ala Leu Asn Asp Ser Arg Tyr Cys Leu Ser Ser Arg Leu
65              70              75              80

Arg Val Ser Ala Thr Phe Trp Gln Asn Pro Arg Asn His Phe Arg Cys
                85              90              95

Gln Val Gln Phe Tyr Gly Leu Ser Glu Asn Asp Glu Trp Thr Gln Asp
            100             105             110

Arg Ala Lys Pro Val Thr Gln Ile Val Ser Ala Glu Ala Trp Gly Arg
        115             120             125

Ala Asp Cys Gly Phe Thr Ser Val Ser Tyr Gln Gln Gly Val Leu Ser
    130             135             140

Ala Thr Ile Leu Tyr Glu Ile Leu Leu Gly Lys Ala Thr Leu Tyr Ala
145             150             155             160

Val Leu Val Ser Ala Leu Val Leu Met Ala Met Val Lys Arg Lys Asp
                165             170             175

Phe
```

<210> SEQ ID NO 12
<211> LENGTH: 171
<212> TYPE: PRT
<213> ORGANISM: Artificial Sequence
<220> FEATURE:
<223> OTHER INFORMATION: Synthetic Polypeptide
<220> FEATURE:
<221> NAME/KEY: VARIANT
<222> LOCATION: (1)...(1)
<223> OTHER INFORMATION: Xaa is any natural amino acid

<400> SEQUENCE: 12

```
Xaa Asp Leu Arg Asn Val Thr Pro Pro Lys Val Ser Leu Phe Glu Pro
1               5               10              15

Ser Lys Ala Glu Ile Ala Asn Lys Gln Lys Ala Thr Leu Val Cys Leu
            20              25              30

Ala Arg Gly Phe Phe Pro Asp His Val Glu Leu Ser Trp Trp Val Asn
        35              40              45

Gly Lys Glu Val His Ser Gly Val Ser Thr Asp Pro Gln Ala Tyr Lys
    50              55              60

Glu Ser Asn Tyr Ser Tyr Cys Leu Ser Ser Arg Leu Arg Val Ser Ala
65              70              75              80

Thr Phe Trp His Asn Pro Arg Asn His Phe Arg Cys Gln Val Gln Phe
            85              90              95

His Gly Leu Ser Glu Glu Asp Lys Trp Pro Glu Gly Ser Pro Lys Pro
            100             105             110

Val Thr Gln Asn Ile Ser Ala Glu Ala Trp Gly Arg Ala Asp Cys Gly
        115             120             125

Ile Thr Ser Ala Ser Tyr Gln Gln Gly Val Leu Ser Ala Thr Ile Leu
    130             135             140

Tyr Glu Ile Leu Leu Gly Lys Ala Thr Leu Tyr Ala Val Leu Val Ser
145             150             155             160

Thr Leu Val Val Met Ala Met Val Arg Asn Arg
                165             170
```

<210> SEQ ID NO 13
<211> LENGTH: 173

-continued

```
<212> TYPE: PRT
<213> ORGANISM: Artificial Sequence
<220> FEATURE:
<223> OTHER INFORMATION: Synthetic Polypeptide
<220> FEATURE:
<221> NAME/KEY: VARIANT
<222> LOCATION: (1)...(1)
<223> OTHER INFORMATION: Xaa is any natural amino acid

<400> SEQUENCE: 13

Xaa Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
        35                  40                  45

Gly Lys Glu Val His Ser Gly Val Ser Thr Asp Pro Gln Ala Tyr Lys
    50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp Cys Gly
            115                 120                 125

Ile Thr Ser Ala Ser Tyr His Gln Gly Val Leu Ser Ala Thr Ile Leu
    130                 135                 140

Tyr Glu Ile Leu Leu Gly Lys Ala Thr Leu Tyr Ala Val Leu Val Ser
145                 150                 155                 160

Gly Leu Val Leu Met Ala Met Val Lys Lys Lys Asn Ser
                165                 170

<210> SEQ ID NO 14
<211> LENGTH: 177
<212> TYPE: PRT
<213> ORGANISM: Artificial Sequence
<220> FEATURE:
<223> OTHER INFORMATION: Synthetic Polypeptide

<400> SEQUENCE: 14

Glu Asp Leu Asn Lys Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Phe Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Glu Asp Lys Trp Pro Glu Gly
            100                 105                 110

Ser Pro Lys Pro Val Thr Gln Ile Val Ser Ala Glu Ala Trp Gly Arg
            115                 120                 125

Ala Asp Cys Gly Phe Thr Ser Val Ser Tyr Gln Gln Gly Val Leu Ser
```

-continued

```
            130             135             140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Phe

<210> SEQ ID NO 15
<211> LENGTH: 179
<212> TYPE: PRT
<213> ORGANISM: Artificial Sequence
<220> FEATURE:
<223> OTHER INFORMATION: Synthetic Polypeptide

<400> SEQUENCE: 15

Glu Asp Leu Arg Asn Val Thr Pro Pro Lys Val Ala Val Phe Glu Pro
1                   5                   10                  15

Ser Glu Ala Glu Ile Ser His Thr Gln Lys Ala Thr Leu Val Cys Leu
                20                  25                  30

Ala Thr Gly Phe Phe Pro Asp His Val Glu Leu Ser Trp Trp Val Asn
            35                  40                  45

Gly Lys Glu Val His Ser Gly Val Ser Thr Asp Pro Gln Pro Leu Lys
        50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Glu Asp Lys Trp Pro Glu Gly
                100                 105                 110

Ser Pro Lys Pro Val Thr Gln Ile Val Ser Ala Glu Ala Trp Gly Arg
            115                 120                 125

Ala Asp Cys Gly Phe Thr Ser Glu Ser Tyr Gln Gln Gly Val Leu Ser
            130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly

<210> SEQ ID NO 16
<211> LENGTH: 179
<212> TYPE: PRT
<213> ORGANISM: Artificial Sequence
<220> FEATURE:
<223> OTHER INFORMATION: Synthetic Polypeptide

<400> SEQUENCE: 16

Glu Asp Leu Lys Asn Val Thr Pro Pro Lys Val Ala Val Phe Glu Pro
1                   5                   10                  15

Ser Glu Ala Glu Ile Ser His Thr Gln Lys Ala Thr Leu Val Cys Leu
                20                  25                  30

Ala Thr Gly Phe Phe Pro Asp His Val Glu Leu Ser Trp Trp Val Asn
            35                  40                  45

Gly Lys Glu Val His Ser Gly Val Ser Thr Asp Pro Gln Pro Leu Lys
        50                  55                  60

Glu Gln Pro Ala Leu Asn Asp Ser Arg Tyr Cys Leu Ser Ser Arg Leu
65                  70                  75                  80
```

```
Arg Val Ser Ala Thr Phe Trp Gln Asn Pro Arg Asn His Phe Arg Cys
              85                  90                  95

Gln Val Gln Phe Tyr Gly Leu Ser Glu Glu Asp Lys Trp Pro Glu Gly
              100                 105                 110

Ser Pro Lys Pro Val Thr Gln Ile Val Ser Ala Glu Ala Trp Gly Arg
              115                 120                 125

Ala Asp Cys Gly Phe Thr Ser Glu Ser Tyr Gln Gln Gly Val Leu Ser
          130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                  165                 170                 175

Ser Arg Gly
```

<210> SEQ ID NO 17
<211> LENGTH: 179
<212> TYPE: PRT
<213> ORGANISM: Artificial Sequence
<220> FEATURE:
<223> OTHER INFORMATION: Synthetic Polypeptide

<400> SEQUENCE: 17

```
Glu Asp Leu Arg Asn Val Phe Pro Pro Lys Val Ala Val Phe Glu Pro
1               5                   10                  15

Ser Glu Ala Glu Ile Ser His Thr Gln Lys Ala Thr Leu Val Cys Leu
              20                  25                  30

Ala Thr Gly Phe Phe Pro Asp His Val Glu Leu Ser Trp Trp Val Asn
              35                  40                  45

Gly Lys Glu Val His Ser Gly Val Ser Thr Asp Pro Gln Pro Leu Lys
          50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
              85                  90                  95

Gln Val Gln Phe Tyr Gly Leu Ser Glu Glu Asp Lys Trp Pro Glu Gly
              100                 105                 110

Ser Pro Lys Pro Val Thr Gln Ile Val Ser Ala Glu Ala Trp Gly Arg
              115                 120                 125

Ala Asp Cys Gly Phe Thr Ser Glu Ser Tyr Gln Gln Gly Val Leu Ser
          130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                  165                 170                 175

Ser Arg Gly
```

<210> SEQ ID NO 18
<211> LENGTH: 179
<212> TYPE: PRT
<213> ORGANISM: Artificial Sequence
<220> FEATURE:
<223> OTHER INFORMATION: Synthetic Polypeptide

<400> SEQUENCE: 18

```
Glu Asp Leu Arg Asn Val Thr Pro Pro Lys Val Ala Val Phe Glu Pro
1               5                   10                  15
```

-continued

```
Ser Glu Ala Glu Ile Ser His Thr Gln Lys Ala Thr Leu Val Cys Leu
        20                  25                  30

Ala Thr Gly Phe Tyr Pro Asp His Val Glu Leu Ser Trp Trp Val Asn
        35                  40                  45

Gly Lys Glu Val His Ser Gly Val Ser Thr Asp Pro Gln Pro Leu Lys
        50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Glu Asp Lys Trp Pro Glu Gly
            100                 105                 110

Ser Pro Lys Pro Val Thr Gln Ile Val Ser Ala Glu Ala Trp Gly Arg
            115                 120                 125

Ala Asp Cys Gly Phe Thr Ser Glu Ser Tyr Gln Gln Gly Val Leu Ser
            130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly
```

```
<210> SEQ ID NO 19
<211> LENGTH: 179
<212> TYPE: PRT
<213> ORGANISM: Artificial Sequence
<220> FEATURE:
<223> OTHER INFORMATION: Synthetic Polypeptide

<400> SEQUENCE: 19

Glu Asp Leu Arg Asn Val Thr Pro Pro Lys Val Ala Val Phe Glu Pro
1               5                   10                  15

Ser Glu Ala Glu Ile Ser His Thr Gln Lys Ala Thr Leu Val Cys Leu
        20                  25                  30

Ala Thr Gly Phe Phe Pro Asp His Val Glu Leu Ser Trp Trp Val Asn
        35                  40                  45

Gly Lys Glu Val His Ser Gly Val Ser Thr Asp Pro Gln Pro Leu Lys
        50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Lys Trp Pro Glu Gly
            100                 105                 110

Ser Pro Lys Pro Val Thr Gln Ile Val Ser Ala Glu Ala Trp Gly Arg
            115                 120                 125

Ala Asp Cys Gly Phe Thr Ser Glu Ser Tyr Gln Gln Gly Val Leu Ser
            130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly
```

```
<210> SEQ ID NO 20
```

```
<211> LENGTH: 179
<212> TYPE: PRT
<213> ORGANISM: Artificial Sequence
<220> FEATURE:
<223> OTHER INFORMATION: Synthetic Polypeptide

<400> SEQUENCE: 20

Glu Asp Leu Arg Asn Val Thr Pro Pro Lys Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Phe Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Glu Asp Glu Trp Pro Glu Gly
            100                 105                 110

Ser Pro Lys Pro Val Thr Gln Ile Val Ser Ala Glu Ala Trp Gly Arg
        115                 120                 125

Ala Asp Cys Gly Phe Thr Ser Glu Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly

<210> SEQ ID NO 21
<211> LENGTH: 179
<212> TYPE: PRT
<213> ORGANISM: Artificial Sequence
<220> FEATURE:
<223> OTHER INFORMATION: Synthetic Polypeptide

<400> SEQUENCE: 21

Glu Asp Leu Arg Asn Val Thr Pro Pro Lys Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Phe Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Glu Asp Lys Trp Thr Glu Gly
            100                 105                 110

Ser Pro Lys Pro Val Thr Gln Ile Val Ser Ala Glu Ala Trp Gly Arg
        115                 120                 125

Ala Asp Cys Gly Phe Thr Ser Glu Ser Tyr Gln Gln Gly Val Leu Ser
    130                 135                 140
```

-continued

```
Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly

<210> SEQ ID NO 22
<211> LENGTH: 179
<212> TYPE: PRT
<213> ORGANISM: Artificial Sequence
<220> FEATURE:
<223> OTHER INFORMATION: Synthetic Polypeptide

<400> SEQUENCE: 22

Glu Asp Leu Arg Asn Val Thr Pro Pro Lys Val Ala Val Phe Glu Pro
1               5                   10                  15

Ser Glu Ala Glu Ile Ser His Thr Gln Lys Ala Thr Leu Val Cys Leu
                20                  25                  30

Ala Thr Gly Phe Phe Pro Asp His Val Glu Leu Ser Trp Trp Val Asn
            35                  40                  45

Gly Lys Glu Val His Ser Gly Val Ser Thr Asp Pro Gln Pro Leu Lys
        50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Glu Asp Lys Trp Pro Gln Gly
            100                 105                 110

Ser Pro Lys Pro Val Thr Gln Ile Val Ser Ala Glu Ala Trp Gly Arg
        115                 120                 125

Ala Asp Cys Gly Phe Thr Ser Glu Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly

<210> SEQ ID NO 23
<211> LENGTH: 179
<212> TYPE: PRT
<213> ORGANISM: Artificial Sequence
<220> FEATURE:
<223> OTHER INFORMATION: Synthetic Polypeptide

<400> SEQUENCE: 23

Glu Asp Leu Arg Asn Val Thr Pro Pro Lys Val Ala Val Phe Glu Pro
1               5                   10                  15

Ser Glu Ala Glu Ile Ser His Thr Gln Lys Ala Thr Leu Val Cys Leu
                20                  25                  30

Ala Thr Gly Phe Phe Pro Asp His Val Glu Leu Ser Trp Trp Val Asn
            35                  40                  45

Gly Lys Glu Val His Ser Gly Val Ser Thr Asp Pro Gln Pro Leu Lys
        50                  55                  60

Glu Gln Pro Ala Leu Asn Asp Ser Arg Tyr Cys Leu Ser Ser Arg Leu
65                  70                  75                  80
```

-continued

```
Arg Val Ser Ala Thr Phe Trp Gln Asn Pro Arg Asn His Phe Arg Cys
                85                  90                  95

Gln Val Gln Phe Tyr Gly Leu Ser Glu Glu Asp Lys Trp Pro Glu Asp
            100                 105                 110

Ser Pro Lys Pro Val Thr Gln Ile Val Ser Ala Glu Ala Trp Gly Arg
        115                 120                 125

Ala Asp Cys Gly Phe Thr Ser Glu Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly

<210> SEQ ID NO 24
<211> LENGTH: 179
<212> TYPE: PRT
<213> ORGANISM: Artificial Sequence
<220> FEATURE:
<223> OTHER INFORMATION: Synthetic Polypeptide

<400> SEQUENCE: 24

Glu Asp Leu Arg Asn Val Thr Pro Pro Lys Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Phe Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Glu Asp Lys Trp Pro Glu Gly
            100                 105                 110

Arg Pro Lys Pro Val Thr Gln Ile Val Ser Ala Glu Ala Trp Gly Arg
        115                 120                 125

Ala Asp Cys Gly Phe Thr Ser Glu Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly

<210> SEQ ID NO 25
<211> LENGTH: 179
<212> TYPE: PRT
<213> ORGANISM: Artificial Sequence
<220> FEATURE:
<223> OTHER INFORMATION: Synthetic Polypeptide

<400> SEQUENCE: 25

Glu Asp Leu Arg Asn Val Thr Pro Pro Lys Val Ala Val Phe Glu Pro
1               5                   10                  15

Ser Glu Ala Glu Ile Ser His Thr Gln Lys Ala Thr Leu Val Cys Leu
```

-continued

```
                20              25              30

Ala Thr Gly Phe Phe Pro Asp His Val Glu Leu Ser Trp Trp Val Asn
            35              40              45

Gly Lys Glu Val His Ser Gly Val Ser Thr Asp Pro Gln Pro Leu Lys
        50              55              60

Glu Gln Pro Ala Leu Asn Asp Ser Arg Tyr Cys Leu Ser Ser Arg Leu
65              70              75              80

Arg Val Ser Ala Thr Phe Trp Gln Asn Pro Arg Asn His Phe Arg Cys
                85              90              95

Gln Val Gln Phe Tyr Gly Leu Ser Glu Glu Asp Lys Trp Pro Glu Gly
            100             105             110

Ser Ala Lys Pro Val Thr Gln Ile Val Ser Ala Glu Ala Trp Gly Arg
        115             120             125

Ala Asp Cys Gly Phe Thr Ser Glu Ser Tyr Gln Gln Gly Val Leu Ser
        130             135             140

Ala Thr Ile Leu Tyr Glu Ile Leu Leu Gly Lys Ala Thr Leu Tyr Ala
145             150             155             160

Val Leu Val Ser Ala Leu Val Leu Met Ala Met Val Lys Arg Lys Asp
            165             170             175

Ser Arg Gly
```

```
<210> SEQ ID NO 26
<211> LENGTH: 179
<212> TYPE: PRT
<213> ORGANISM: Artificial Sequence
<220> FEATURE:
<223> OTHER INFORMATION: Synthetic Polypeptide

<400> SEQUENCE: 26
```

```
Glu Asp Leu Arg Asn Val Thr Pro Pro Lys Val Ala Val Phe Glu Pro
1               5               10              15

Ser Glu Ala Glu Ile Ser His Thr Gln Lys Ala Thr Leu Val Cys Leu
            20              25              30

Ala Thr Gly Phe Tyr Pro Asp His Val Glu Leu Ser Trp Trp Val Asn
            35              40              45

Gly Lys Glu Val His Ser Gly Val Ser Thr Asp Pro Gln Pro Leu Lys
        50              55              60

Glu Gln Pro Ala Leu Asn Asp Ser Arg Tyr Cys Leu Ser Ser Arg Leu
65              70              75              80

Arg Val Ser Ala Thr Phe Trp Gln Asn Pro Arg Asn His Phe Arg Cys
                85              90              95

Gln Val Gln Phe Tyr Gly Leu Ser Glu Asn Asp Lys Trp Pro Glu Gly
            100             105             110

Ser Ala Lys Pro Val Thr Gln Ile Val Ser Ala Glu Ala Trp Gly Arg
        115             120             125

Ala Asp Cys Gly Phe Thr Ser Glu Ser Tyr Gln Gln Gly Val Leu Ser
        130             135             140

Ala Thr Ile Leu Tyr Glu Ile Leu Leu Gly Lys Ala Thr Leu Tyr Ala
145             150             155             160

Val Leu Val Ser Ala Leu Val Leu Met Ala Met Val Lys Arg Lys Asp
            165             170             175

Ser Arg Gly
```

```
<210> SEQ ID NO 27
<211> LENGTH: 179
```

```
<212> TYPE: PRT
<213> ORGANISM: Artificial Sequence
<220> FEATURE:
<223> OTHER INFORMATION: Synthetic Polypeptide

<400> SEQUENCE: 27

Glu Asp Leu Arg Asn Val Phe Pro Pro Lys Val Ala Val Phe Glu Pro
1               5                   10                  15

Ser Glu Ala Glu Ile Ser His Thr Gln Lys Ala Thr Leu Val Cys Leu
                20                  25                  30

Ala Thr Gly Phe Tyr Pro Asp His Val Glu Leu Ser Trp Trp Val Asn
            35                  40                  45

Gly Lys Glu Val His Ser Gly Val Ser Thr Asp Pro Gln Pro Leu Lys
        50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Lys Trp Pro Glu Gly
            100                 105                 110

Ser Ala Lys Pro Val Thr Gln Ile Val Ser Ala Glu Ala Trp Gly Arg
        115                 120                 125

Ala Asp Cys Gly Phe Thr Ser Glu Ser Tyr Gln Gln Gly Val Leu Ser
        130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly

<210> SEQ ID NO 28
<211> LENGTH: 276
<212> TYPE: PRT
<213> ORGANISM: Artificial Sequence
<220> FEATURE:
<223> OTHER INFORMATION: Synthetic Polypeptide

<400> SEQUENCE: 28

Met Lys Ser Leu Arg Val Leu Leu Val Ile Leu Trp Leu Gln Leu Ser
1               5                   10                  15

Trp Val Trp Ser Gln Lys Gln Glu Val Thr Gln Ile Pro Ala Ala Leu
                20                  25                  30

Ser Val Pro Glu Gly Glu Asn Leu Val Leu Asn Cys Ser Phe Thr Asp
            35                  40                  45

Ser Ala Ile Tyr Asn Leu Gln Trp Phe Arg Gln Asp Pro Gly Lys Gly
        50                  55                  60

Leu Thr Ser Leu Leu Leu Ile Gln Ser Ser Gln Arg Glu Gln Thr Ser
65                  70                  75                  80

Gly Arg Leu Asn Ala Ser Leu Asp Lys Ser Ser Gly Arg Ser Thr Leu
                85                  90                  95

Tyr Ile Ala Ala Ser Gln Pro Gly Asp Ser Ala Thr Tyr Leu Cys Ala
            100                 105                 110

Val Arg Pro Leu Tyr Gly Gly Ser Tyr Ile Pro Thr Phe Gly Arg Gly
        115                 120                 125

Thr Ser Leu Ile Val His Pro Tyr Ile Gln Asn Pro Asp Pro Ala Val
        130                 135                 140
```

-continued

```
Tyr Gln Leu Arg Asp Ser Lys Ser Ser Asp Lys Ser Val Cys Leu Phe
145                 150                 155                 160

Thr Asp Phe Asp Ser Gln Thr Asn Val Ser Gln Ser Lys Asp Ser Asp
                165                 170                 175

Val Tyr Ile Thr Asp Lys Thr Val Leu Asp Met Arg Ser Met Asp Phe
                180                 185                 190

Lys Ser Asn Ser Ala Val Ala Trp Ser Asn Lys Ser Asp Phe Ala Cys
                195                 200                 205

Ala Asn Ala Phe Asn Asn Ser Ile Ile Pro Glu Asp Thr Phe Phe Pro
                210                 215                 220

Ser Pro Glu Ser Ser Cys Asp Val Lys Leu Val Glu Lys Ser Phe Glu
225                 230                 235                 240

Thr Asp Thr Asn Leu Asn Phe Gln Asn Leu Ser Val Ile Gly Phe Arg
                245                 250                 255

Ile Leu Leu Leu Lys Val Ala Gly Phe Asn Leu Leu Met Thr Leu Arg
                260                 265                 270

Leu Trp Ser Ser
                275

<210> SEQ ID NO 29
<211> LENGTH: 311
<212> TYPE: PRT
<213> ORGANISM: Artificial Sequence
<220> FEATURE:
<223> OTHER INFORMATION: Synthetic Polypeptide

<400> SEQUENCE: 29

Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
                20                  25                  30

Lys Thr Gly Gln Ser Met Thr Leu Gln Cys Ala Gln Asp Met Asn His
            35                  40                  45

Glu Tyr Met Ser Trp Tyr Arg Gln Asp Pro Gly Met Gly Leu Arg Leu
        50                  55                  60

Ile His Tyr Ser Val Gly Ala Gly Ile Thr Asp Gln Gly Glu Val Pro
65                  70                  75                  80

Asn Gly Tyr Asn Val Ser Arg Ser Thr Thr Glu Asp Phe Pro Leu Arg
                85                  90                  95

Leu Leu Ser Ala Ala Pro Ser Gln Thr Ser Val Tyr Phe Cys Ala Ser
                100                 105                 110

Ser Tyr Val Gly Asn Thr Gly Glu Leu Phe Phe Gly Glu Gly Ser Arg
                115                 120                 125

Leu Thr Val Leu Glu Asp Leu Lys Asn Val Phe Pro Pro Lys Val Ala
            130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
                180                 185                 190

Gln Pro Leu Lys Glu Gln Pro Ala Leu Asn Asp Ser Arg Tyr Cys Leu
            195                 200                 205

Ser Ser Arg Leu Arg Val Ser Ala Thr Phe Trp Gln Asn Pro Arg Asn
        210                 215                 220
```

-continued

```
His Phe Arg Cys Gln Val Gln Phe Tyr Gly Leu Ser Glu Asn Asp Glu
225                 230                 235             240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
                260                 265                 270

Gly Val Leu Ser Ala Thr Ile Leu Tyr Glu Ile Leu Leu Gly Lys Ala
            275                 280                 285

Thr Leu Tyr Ala Val Leu Val Ser Ala Leu Val Leu Met Ala Met Val
            290                 295                 300

Lys Arg Lys Asp Ser Arg Gly
305                 310

<210> SEQ ID NO 30
<211> LENGTH: 135
<212> TYPE: PRT
<213> ORGANISM: Artificial Sequence
<220> FEATURE:
<223> OTHER INFORMATION: Synthetic Polypeptide

<400> SEQUENCE: 30

Met Lys Ser Leu Arg Val Leu Leu Val Ile Leu Trp Leu Gln Leu Ser
1               5                   10                  15

Trp Val Trp Ser Gln Lys Gln Glu Val Thr Gln Ile Pro Ala Ala Leu
                20                  25                  30

Ser Val Pro Glu Gly Glu Asn Leu Val Leu Asn Cys Ser Phe Thr Asp
            35                  40                  45

Ser Ala Ile Tyr Asn Leu Gln Trp Phe Arg Gln Asp Pro Gly Lys Gly
            50                  55                  60

Leu Thr Ser Leu Leu Leu Ile Gln Ser Ser Gln Arg Glu Gln Thr Ser
65                  70                  75                  80

Gly Arg Leu Asn Ala Ser Leu Asp Lys Ser Ser Gly Arg Ser Thr Leu
                85                  90                  95

Tyr Ile Ala Ala Ser Gln Pro Gly Asp Ser Ala Thr Tyr Leu Cys Ala
                100                 105                 110

Val Arg Pro Leu Tyr Gly Gly Ser Tyr Ile Pro Thr Phe Gly Arg Gly
            115                 120                 125

Thr Ser Leu Ile Val His Pro
    130                 135

<210> SEQ ID NO 31
<211> LENGTH: 132
<212> TYPE: PRT
<213> ORGANISM: Artificial Sequence
<220> FEATURE:
<223> OTHER INFORMATION: Synthetic Polypeptide

<400> SEQUENCE: 31

Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
                20                  25                  30

Lys Thr Gly Gln Ser Met Thr Leu Gln Cys Ala Gln Asp Met Asn His
            35                  40                  45

Glu Tyr Met Ser Trp Tyr Arg Gln Asp Pro Gly Met Gly Leu Arg Leu
            50                  55                  60

Ile His Tyr Ser Val Gly Ala Gly Ile Thr Asp Gln Gly Glu Val Pro
65                  70                  75                  80
```

-continued

```
Asn Gly Tyr Asn Val Ser Arg Ser Thr Thr Glu Asp Phe Pro Leu Arg
            85                  90                  95

Leu Leu Ser Ala Ala Pro Ser Gln Thr Ser Val Tyr Phe Cys Ala Ser
            100                 105                 110

Ser Tyr Val Gly Asn Thr Gly Glu Leu Phe Phe Gly Glu Gly Ser Arg
        115                 120                 125

Leu Thr Val Leu
    130

<210> SEQ ID NO 32
<211> LENGTH: 120
<212> TYPE: PRT
<213> ORGANISM: Artificial Sequence
<220> FEATURE:
<223> OTHER INFORMATION: Synthetic Polypeptide

<400> SEQUENCE: 32

Glu Val Tyr Leu Val Glu Ser Gly Gly Asp Leu Val Gln Pro Gly Ser
1               5                   10                  15

Ser Leu Lys Val Ser Cys Ala Ala Ser Gly Phe Thr Phe Ser Asp Phe
            20                  25                  30

Trp Met Tyr Trp Val Arg Gln Ala Pro Gly Lys Gly Leu Glu Trp Val
        35                  40                  45

Gly Arg Ile Lys Asn Ile Pro Asn Asn Tyr Ala Thr Glu Tyr Ala Asp
    50                  55                  60

Ser Val Arg Gly Arg Phe Thr Ile Ser Arg Asp Asp Ser Arg Asn Ser
65                  70                  75                  80

Ile Tyr Leu Gln Met Asn Arg Leu Arg Val Asp Asp Thr Ala Ile Tyr
            85                  90                  95

Tyr Cys Thr Arg Ala Gly Arg Phe Asp His Phe Asp Tyr Trp Gly Gln
            100                 105                 110

Gly Thr Met Val Thr Val Ser Ser
        115                 120

<210> SEQ ID NO 33
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 33

Tyr Glu Leu Ile Gln Pro Ser Ser Ala Ser Val Thr Val Gly Glu Thr
1               5                   10                  15

Val Lys Ile Thr Cys Ser Gly Asp Gln Leu Pro Lys Asn Phe Ala Tyr
            20                  25                  30

Trp Phe Gln Gln Lys Ser Asp Lys Asn Ile Leu Leu Leu Ile Tyr Met
        35                  40                  45

Asp Asn Lys Arg Pro Ser Gly Ile Pro Glu Arg Phe Ser Gly Ser Thr
    50                  55                  60

Ser Gly Thr Thr Ala Thr Leu Thr Ile Ser Gly Ala Gln Pro Glu Asp
65                  70                  75                  80

Glu Ala Ala Tyr Tyr Cys Leu Ser Ser Tyr Gly Asp Asn Asn Asp Leu
            85                  90                  95

Val Phe Gly Ser Gly Thr Gln Leu Thr Val Leu
        100                 105
```

-continued

<210> SEQ ID NO 34
<211> LENGTH: 133
<212> TYPE: PRT
<213> ORGANISM: Artificial Sequence
<220> FEATURE:
<223> OTHER INFORMATION: Synthetic Polypeptide

<400> SEQUENCE: 34

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Ala Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Gly Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
    130

<210> SEQ ID NO 35
<211> LENGTH: 133
<212> TYPE: PRT
<213> ORGANISM: Artificial Sequence
<220> FEATURE:
<223> OTHER INFORMATION: Synthetic Polypeptide

<400> SEQUENCE: 35

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 36
<211> LENGTH: 15
<212> TYPE: PRT
<213> ORGANISM: Artificial Sequence
<220> FEATURE:

-continued

```
<223> OTHER INFORMATION: Synthetic Polypeptide

<400> SEQUENCE: 36

Gly Gly Gly Gly Ser Gly Gly Gly Gly Ser Gly Gly Gly Gly Ser
1               5                   10                  15

<210> SEQ ID NO 37
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 37

Asp Tyr Lys Asp Asp Asp Asp Lys
1               5

<210> SEQ ID NO 38
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 38

Glu Gln Lys Leu Ile Ser Glu Glu Asp Leu
1               5                   10

<210> SEQ ID NO 39
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 39

Tyr Pro Tyr Asp Val Pro Asp Tyr Ala
1               5

<210> SEQ ID NO 40
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 40

Gly Lys Pro Ile Pro Asn Pro Leu Leu Gly Leu Asp Ser Thr
1               5                   10
```

PEPTIDE MARKERS TO TRACK GENETICALLY ENGINEERED CELLS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

REFERENCE TO SEQUENCE LISTING

The present application is being filed along with a Sequence Listing in electronic format. The Sequence Listing is provided as a file entitled SeqList_NTBV016A created on Dec. 20, 2021, which is 47,154 bytes in size. The information in the electronic format of the Sequence Listing is incorporated herein by reference in its entirety.

BACKGROUND

Cell therapy is a therapy in which viable cells are injected, grafted or implanted into a patient in order to effectuate a medicinal effect, for example, by transplanting T-cells capable of fighting cancer cells via cell-mediated immunity in the course of immunotherapy, or grafting stem cells to regenerate diseased tissues.

SUMMARY

Some embodiments described herein relate to a marked protein comprising a TCR constant domain and an exogenous amino acid variation that comprises a sequence that is detectable and identifiable within the TCR constant domain.

In some embodiments, a marked protein that can be used for the detection, isolation, or depletion of genetically engineered cells. A marked protein or protein marker can function as a marker; any cells containing the marked protein can be detected, isolated, or depleted by finding the marker. A marked protein can comprise an epitope peptide, which can be identified by a suitable antibody.

Some embodiments described herein relate to a marked protein used for the detection, isolation, or depletion of genetically engineered T cells that have been modified by the introduction of therapeutic TCR genes, wherein the marked protein is derived from the murine TCR Cβ domain and introduced into the human TCR Cβ2 domain by mutation of existing amino acids within the human TCR Cβ2 domain.

In some embodiments a marked protein is provided for the detection, isolation or depletion of a cell modified with a novel TCR gene for the treatment of cancer, comprising the marked protein of any one of the embodiments provided herein.

Some embodiments relate to a kit used for detection, isolation or depletion of genetically engineered cells having the marked protein of any one of the above embodiments, comprising an antibody or binding agent that recognizes the marked protein.

Some embodiments relate to a marked protein used for targeted delivery of one or more payloads to genetically engineered cells expressing such a marked protein, comprising the marked protein of any one of embodiments described herein.

Some embodiments relate to a method for targeted delivery of one or more payloads to genetically engineered cells expressing a marked protein. The method includes a) obtaining a conjugate comprising the one or more payloads and a binding agent, wherein the binding agent specifically binds to the marked protein, and b) contacting the genetically engineered cells with the conjugate.

Some embodiments relate to an antibody epitope that can be inserted or made part of a TCR chain. In some embodiments, the epitope can be used for the detection of genetically engineered cells expressing such an antibody epitope, wherein the antibody epitope is attached to a TCR chain or a Chimeric Antigen Receptor. In some embodiments, the antibody epitope comprises a 2A peptide sequence, a HA.11 epitope tag, a FLAG epitope tag, a Myc epitope tag, or a V5 epitope tag. In some embodiments, the antibody epitope is inserted into the constant domain of a TCR chain and not the variable domain of a TCR. In some embodiments the antibody epitope is introduced by amino acid exchange in one or more positions of a TCR chain and not by addition of additional exogenous amino acids to the TCR chain.

Some embodiments relate to an antibody epitope used for the detection of genetically engineered T cells that have been modified by the introduction of therapeutic TCR genes, comprise the antibody epitope of any one of above embodiments.

Some embodiments relate to an antibody epitope for the detection of a cell modified with a novel TCR or CAR gene for the treatment of cancer, comprise the antibody epitope of any one of above embodiments.

Some embodiments relate to a kit used for detection of genetically engineered cells expressing the antibody epitope of any one of above embodiments.

Some embodiments relate to a genetic construct comprising a nucleotide sequence capable of expressing a 2A peptide sequence or a sequence that is at least 90% identical thereto, wherein the construct is configured for the expression of multiple proteins from a single open reading frame, and wherein the nucleotide sequence does not increase the size of the genetic construct by more than 25 amino acids. As used herein, "gene" in the context of the relevant peptide, denotes the nucleic acid sequence encoding the peptide sequence; it does not denote anything more than that.

Some embodiments relate to a genetically engineered cell expressing the marked protein of any one of the preceding embodiments.

These and other features, aspects, and advantages of the present invention will become better understood with reference to the following description and appended claims.

BRIEF DESCRIPTION OF THE DRAWINGS

FIG. 1. Diagram of TCR constant domain epitope.

FIG. 2A shows the diagram of an antibody epitope where the antibody epitope is attached to the C-terminus of a TCR chain.

FIG. 2B shows the diagram of an antibody epitope where the antibody epitope is attached to the N-terminus of a TCR chain.

FIG. 2C shows the diagram of an antibody epitope where the antibody epitope is inserted into a TCR chain.

FIG. 2D shows the diagram of an antibody epitope where the antibody epitope is used to connect TCRα and TCRβ chains; the positions of TCRα and TCRβ chains can be switched.

FIG. 5 shows FACS analysis of human primary T cells with knock-in of the NY-ESO-1 1G4 TCR at the endogenous TRAC locus using various repair templates. The data shows that 6 amino acid residues from the murine Trbc2 A strand and FG loop are necessary to enable H57 antibody recognition.

FIG. 10 shows the sequence of an immunogen used to raise 2A peptide antibody 3H4 (SEQ ID NO: 1).

FIG. 11 shows a T2A peptide sequence (SEQ ID NO: 2).

FIG. 12 shows a P2A peptide sequence (SEQ ID NO: 3).

FIG. 13 shows the sequence of a Human TCR Cβ2 domain containing the murine TCR epitope detectable by the H57 antibody (SEQ ID NO: 4).

FIG. 14 shows the sequence of a Human TCR Cβ2 domain linked to the T2A peptide epitope detectable by the 3H4 antibody (SEQ ID NO: 5).

FIG. 15 shows a fragment of a T2A or P2A peptide sequence (SEQ ID NO: 6).

FIG. 16 shows a fragment of a E2A or F2A peptide sequence (SEQ ID NO: 7).

FIG. 17 shows the sequence of a Human TCR Cβ2 domain (SEQ ID NO: 8).

FIG. 22 shows the CD25 and CD69 expression response over a range of concentrations of IL2, H57-IL2, or H57-IL2v fusion proteins.

FIGS. 26A-26D shows the increase in IFN-γ and IL2 in primary T cells expressing muTRBC2, huTRBC2, and huTRBC2-Mur6 1G4 TCR. FIG. 26A (IFN-γ) and 26C (IL2) show the concentration response for a range of concentrations of the NY-ESO peptide loaded onto target cells. FIG. 26B (IFN-γ) and 26D (IL2) show dot plots for the percentage of cells expressing the marker in individual experiments for the highest peptide loading concentration.

DETAILED DESCRIPTION

Figure 3:
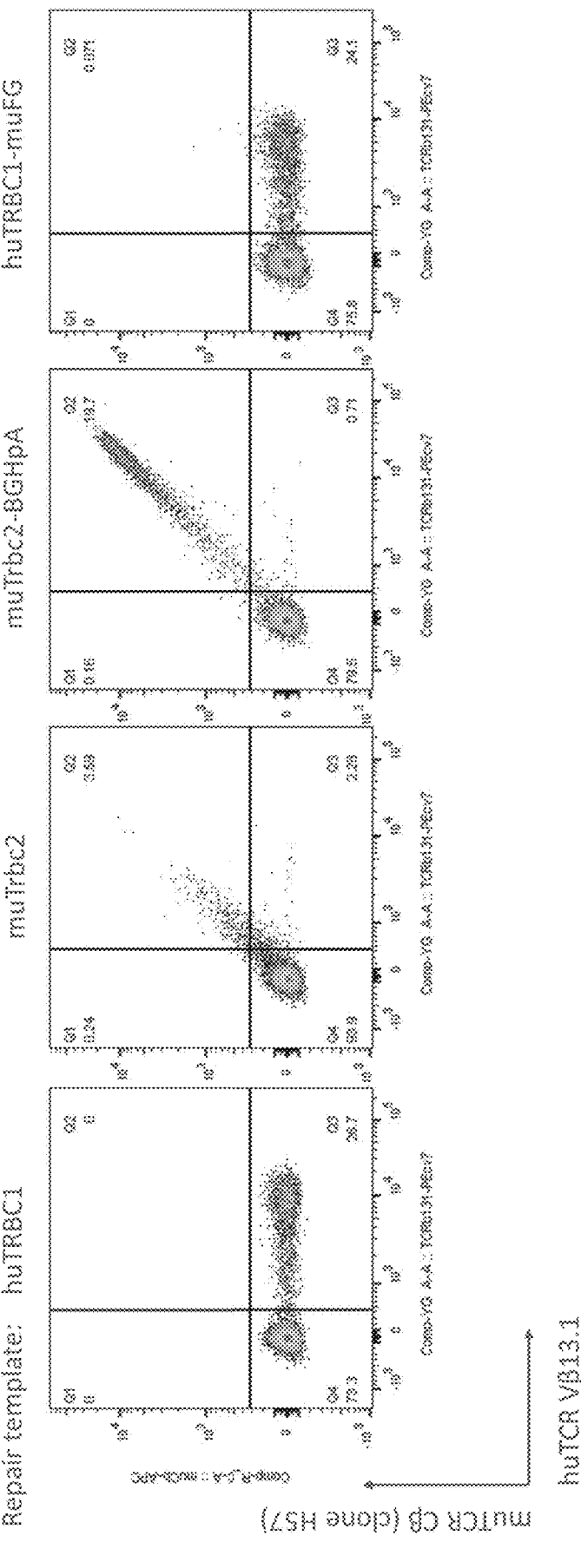
FIG. 3 shows FACS analysis of human primary T cells with knock-in of the NY-ESO-1 1G4 TCR at the endogenous TRAC locus using various repair templates. The data shows that an exogenous polyA signal is useful for TCR expression when using a fully murine Trbc2 sequence, and that cells that express a fully murine Trbc2 sequence can be recognized by the H57 antibody.

In the Summary Section above and the Detailed Description Section, and the claims below, reference is made to particular features of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

Cell therapy includes therapies in which cells are injected or otherwise transplanted into a patient. Genetically engineered T cells are one such material. To allow for control over injected genetically engineered T cells, it is useful that the genetically engineered T cells express a marker that can be used to detect such T cells among a pool of unmodified cells. Ideally, such a maker can also be used to isolate the successfully modified T cells during manufacturing, or once administered to a patient, can be used to track, or deplete those T cells. Further, such a marker should be non-immunogenic and should form a natural part of the therapeutic gene construct. For example, such a marker can be a polypeptide, which can form an epitope to which an antibody can bind.

Some embodiments described herein relate to a marked protein that can be used for the detection, isolation, or depletion of genetically engineered cells. A marked protein or protein marker can function as a marker; any cells containing the marked protein can be detected, isolated, or depleted by finding the marker. In some embodiments, a marked protein comprises a TCR constant domain and an exogenous amino acid variation that comprises a sequence that is detectable and identifiable within the TCR constant domain.

Some embodiments relate to a marked protein used for targeted delivery of one or more payloads to genetically engineered cells expressing such a marked protein, comprising the marked protein of any one of embodiments described herein.

Some embodiments relate to an antibody epitope that can be inserted or made part of a TCR chain. In some embodiments, the epitope can be used for the detection of genetically engineered cells expressing such an antibody epitope, wherein the antibody epitope is attached to a TCR chain or a Chimeric Antigen Receptor.

Definitions

Throughout this specification the word "comprise," or variations such as "comprises" or "comprising," will be understood to imply the inclusion of a stated element, integer or step, or group of elements, integers or steps, but not the exclusion of any other element, integer or step, or group of elements, integers or steps.

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a nucleic acid molecule" includes single or plural nucleic acid molecules and is considered equivalent to the phrase "comprising at least one nucleic acid molecule." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. Unless otherwise specified, the definitions provided herein control when the present definitions may be different from other possible definitions.

Unless explained otherwise, all technical and scientific terms used herein have the same meaning as commonly understood to one of ordinary skill in the art to which this disclosure belongs. All HUGO Gene Nomenclature Committee (HGNC) identifiers (IDs) mentioned herein are incorporated by reference in their entirety. Although methods and materials similar or equivalent to those described herein can be used in the practice or testing of the present disclosure, suitable methods and materials are described below. The materials, methods, and examples are illustrative only and not intended to be limiting.

"T cell receptor" or "TCR" denotes a molecule found on the surface of T cells or T lymphocytes that recognizes antigen bound as peptides to major histocompatibility complex (MHC) molecules. The TCR is composed of two different protein chains (that is, it is a hetero dimer). In humans, in 95% of T cells the TCR consists of an alpha (α) chain and a beta (β) chain (encoded by TRA and TRB, respectively), whereas in 5% of T cells the TCR consists of gamma and delta (γ/δ) chains (encoded by TRG and TRD, respectively). This ratio changes during ontogeny and in diseased states (such as leukemia). It also differs between species. Each TCR chain is composed of two extracellular domains: Variable (V) region and a Constant (C) region. The Constant region is proximal to the cell membrane, followed by a transmembrane region and a short cytoplasmic tail, while the Variable region binds to the peptide/MHC complex. The variable domain of both the TCRα and TCRβ chains has three hypervariable complementarity determining regions (CDRs), denoted CDR1, CDR2, and CDR3. In some embodiments, CDR3 is the main antigen-recognizing region. In some embodiments, TCRα chain genes comprise V and J, and TCRβ chain genes comprise V, D and J gene segments that contribute to TCR diversity. The constant domain of the TCR consists of short connecting sequences in which a cysteine residue forms disulfide bonds, which form a link between the two chains.

The term "therapeutic TCR genes" can refer to specific combinations of TCRα and TCRβ chains that mediate a desired functionality, for example, being able to facilitate a host's immune system to fight against a disease. Therapeutic TCR genes can be selected from in vitro mutated TCR chains expressed as recombinant TCR libraries by phage-, yeast- or T cell-display systems. Therapeutic TCR genes can be autologous or allogeneic.

The term "cancer" denotes a malignant neoplasm that has undergone characteristic anaplasia with loss of differentiation, increased rate of growth, invasion of surrounding tissue, and is capable of metastasis. The term "cancer" shall be taken to include a disease that is characterized by uncontrolled growth of cells within a subject. In some embodiments, the terms "cancer" and "tumor" are used interchangeably. In some embodiments, the term "tumor" refers to a benign or non-malignant growth.

As used herein, the term "neo-antigen" refers to an antigen derived from a tumor-specific genomic mutation. For example, a neo-antigen can result from the expression of a mutated protein in a tumor sample due to a non-synonymous single nucleotide mutation or from the expression of alternative open reading frames due to mutation induced frame-shifts. Thus, a neo-antigen may be associated with a pathological condition. In some embodiments, "mutated protein" refers to a protein comprising at least one amino acid that is different from the amino acid in the same position of the canonical amino acid sequence. In some embodiments, a mutated protein comprises insertions, deletions, substitutions, inclusion of amino acids resulting from reading frame shifts, or any combination thereof, relative to the canonical amino acid sequence.

"Antibody" denotes a polypeptide including at least a light chain or heavy chain immunoglobulin variable region which specifically recognizes and binds an epitope of an antigen. In some embodiments, antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody. The term antibody includes intact immunoglobulins, as well the variants and portions thereof, such as Fab' fragments, F(ab)'$_2$ fragments, and any other molecule derived from an intact immunoglobulin.

"Genetically engineered cells" are cells that have changes in their genetic makeup using biotechnology. Such changes include transfer of genes within and across species boundaries to produce improved or novel organisms. New DNA is obtained by either isolating and copying the genetic material of interest using recombinant DNA methods or by artificially synthesizing the DNA.

"Genetically engineered T cells" are T cells that have changes in their genetic makeup using biotechnology.

Epitope peptide, epitope protein, and antibody epitope are used interchangeably herein. With regard to certain specifically named epitopes, the name may also be used in place of a word or phrase having the word epitope. For the epitope designated "mur6," the name may refer to either huTRBC1-Mur6 or huTRBC2-Mur6 as appropriate in context.

Various Embodiments Relating to Marked Proteins

Some embodiments described herein relate to a marked protein that can be used for the detection, isolation, or depletion of genetically engineered cells. A marked protein or protein marker can function as a marker; any cells containing the marked protein can be detected, isolated, or depleted by finding the marker. A marked protein can comprise an epitope peptide, which can be identified by a suitable antibody. In some embodiments the marked protein can be used for stimulation of cells. In some embodiments, the marked protein is introduced into T cells to allow detection, isolation or depletion of genetically engineered T cells. In some embodiments, the marked protein is introduced into T cells to allow stimulation of engineered T cells. In some embodiments, the marked protein is introduced into engineered T cells in order to create a 'handle' to deliver components, including but not limited to cytokines, nucleic acids and small molecules. In some embodiments, the marked protein is not used for stimulation.

The diagram of some embodiments is shown in FIG. 1. In some embodiments, the TCR constant domain shown in FIG. 1 can be a TCRα or TCRβ constant domain. A full-length or only a partial TCR constant domain may be used.

In some embodiments, a marked protein comprises a TCR constant domain and an exogenous amino acid variation that comprises a sequence that is detectable and identifiable within the TCR constant domain. In some embodiments the amino acid variation is introduced into the TCR constant domain rather than in the TCR variable domain to preserve TCR specificity and sensitivity. In some embodiments, the antibody epitope is inserted into the constant domain of a TCR chain and not the variable domain of a TCR. In some embodiments the antibody epitope is introduced by amino acid exchange in one or more positions of a TCR chain and not by addition of additional exogenous amino acids to the TCR chain.

To be detectable and identifiable means to be able to be discovered or identified by molecular biology techniques or some other related technique. For example, a marked protein is detectable and identifiable if it can bind to a specific antibody, then detected and identified by standard molecular biology techniques, which include, but are not limited to, flow cytometry, IHC, immunofluorescence microscopy, western blot, and ELISA. In some embodiments, the marked protein is expressed on the cell surface, so accessible to extracellular antibody binding.

An exogenous amino acid variation refers to an amino acid sequence not found natively in the species of the TCR constant domain. The exogenous amino acid variation can be an amino acid sequence from another species, or an artificial sequence. Furthermore, it can be a continuous or a discontinuous amino acid sequence. For example, in some embodiments, the TCR constant domain is from one species and the exogenous amino acid variation is from another species. In some embodiments, the TCR constant domain is from human and the exogenous amino acid variation is from non-human species. In some embodiments, the non-human species is mouse.

An exogenous amino acid variation can be derived from mutating certain amino acids of a TCR constant domain. For example, certain amino acids of human TCR constant domain can be mutated so that a piece of the amino acid sequence of human TCR constant domain has changed to a murine TCR sequence. By this way, a murine epitope can be introduced into the human TCR constant domain resulting in a marked protein, while the total number of amino acids of the marked protein is the same as the native human TCR constant protein. Thus, one of the advantages of this approach is that it does not increase the size of a marked protein as compared to the native human TCR constant domain. In addition, the marked protein is incorporated into the TCRbeta constant domain, so it has the same stability and expression as the TCR itself. Furthermore, the introduction of selective amino acids from the murine TCR constant domain rather than use of complete murine TCR constant domains may reduce the immunogenicity of the marker protein. In some embodiments, the mutation comprises 10 amino acid mutations. In some embodiments, the mutation comprises 6 amino acid mutations. In some embodiments, the mutations are only introduced into a one of the two TCR constant domains.

There are other ways that an exogenous amino acid variation can be introduced into a TCR constant domain. For example, a piece of amino acid sequence of a TCR constant domain of a first species can be inserted into and replace a sequence within a TCR constant domain of a second species having the same number of amino acids to make a marked protein. This approach also does not increase the size of a marked protein as compared to the native TCR constant domain of the second species.

In some embodiments, the TCR constant domain comprises a sequence encoded by the human T cell receptor beta constant 2 (TRBC2) gene. In some embodiments, the exogenous amino acid variation comprises a sequence of the murine TCR β chain constant region (TCR Cβ domain). In some embodiments, the exogenous amino acid variation comprises one or more of the following 10 amino acid mutations: K4R, F7T, Y37F, N106E, E108K, T110P, Q111E, D112G, R113S, A114P. In some embodiments, the exogenous amino acid variation includes 2, 3, 4, 5, 6, 7, 8, 9, or 10 of these mutations.

To facilitate discrimination of genetically engineered cells from unmodified cells at a single cell level, antibody reagents are useful to detect protein markers that are unique to the engineered cells. Published studies have shown that hybrid murinized TCRs, in which human TCR Variable domains are linked to mouse TCR Constant domains, are functional and can be detected using the anti-mouse TCR Cβ antibody H57 (Cohen et al, Cancer Res 2006). As used herein, "H57" may refer to any antibody or antigen binding fragment thereof that retains the selective binding properties described herein and has at least the variable regions of H57. This antibody does not bind to human TCR Cβ domains, and therefore can uniquely identify engineered T cells expressing murinized TCRs. The disadvantage of such full TCR constant domain murinization is that it could increase the immunogenicity of the introduced TCR genes (Davis et al, Clin Cancer Res 2010), and that it does not allow the in-frame exonic knock-in of therapeutic TCR genes into the human TCRα or TCRβ constant locus. To overcome these limitations, in some embodiments, a "minimized" murine epitope-containing TCR Cβ domain is generated, in which 10 amino acids are swapped (K4R, F7T, Y37F, N106E, E108K, T110P, Q111E, D112G, R113S, A114P, where the numbering is according to the Ensembl genome browser. Gene: TRBC2 (ENSG00000211772)) in the sequence of the human TRBC2 gene. In some embodiments, the numbering of these residues is with reference to the numbering arrangement within SEQ ID NO: 8. Thus, a reference to "as numbered within SEQ ID NO: 8" denotes the amino acid positional numbering system within SEQ ID NO: 8, not the sequence itself. Of these 10 amino acids, K4 and F7 are part of the TCR Cβ A strand, Y37 is part of the TCR Cβ B strand, and N106-A114 are part of the TCR Cβ FG loop (Sasada et al, J Exp Med 2002). In some embodiments, a "minimized" murine epitope-containing TCR Cβ domain is generated ("huTRBC2-Mur6"), in which 6 amino acids are swapped (K4R, E108K, T110P, Q111E, D112G, R113S) in the sequence of the human TRBC2 gene. These murine epitope-containing TCRβ chains can efficiently pair with full human TCRα chains and be detected at the cell surface by the H57 antibody, which allows the detection, isolation, and depletion of TCR-modified T cells. Furthermore, these murine epitope-containing TCRβ chains are compatible with the in-frame exonic knock-in of therapeutic TCR genes into the human TCRα or TCRβ constant locus.

In some embodiments, the exogenous amino acid variation is detectable and identifiable by an antibody, a nanobody, a Fab fragment or a DARPin®. A nanobody, also known as a single-domain antibody, is an antibody fragment consisting of a single monomeric variable antibody domain; like a whole antibody, it is able to bind selectively to a specific antigen. DARPins® (an acronym for designed ankyrin repeat proteins) are genetically engineered antibody mimetic proteins typically exhibiting highly specific and high-affinity target protein binding; DARPins® are derived from naturally occurring ankyrin proteins, a protein class that mediates high-affinity protein-protein interactions in nature. In some embodiments, the exogenous amino acid variation comprises an antibody epitope, which binds to certain specific antibodies and is detectable and identifiable by such antibodies. The epitope may be a continuous or discontinuous sequence. In some embodiments, position 4 and positions 108-113 in TRBC2 are of murine origin. Detection of TCR-modified T cells with the marked protein according to some embodiments is based on antibody staining that can be detected by flow cytometry.

In some embodiments, the exogenous amino acid variation is detectable and identifiable by an anti-mouse TCR Cβ antibody H57. H57 specifically binds to mouse TCR Cβ domains and does not bind to human TCR Cβ domains. When a murine epitope detectable by H57 is introduced into human TCR Cβ domains, the resulted marked protein can be distinguished from proteins having the native human TCR Cβ domains. Any antibody epitope domains existing in TCRα or TCRβ constant domains (TRAC and TRBC, respectively) of other species may be utilized in similar fashion, such as the antibody epitope detectable by the mouse anti-rat TCR αβ antibody R73.

In some embodiments, targeted mutation of amino acids in human TRAC or TRBC may be used to create artificial antibody epitopes for which an antibody can be created.

In some embodiments, a marked protein is provided. It can be used for the detection, isolation, or depletion of genetically engineered cells expressing such a marked protein, comprising the marked protein of any aforementioned embodiments. In some embodiments, the genetically engineered cells comprise genetically engineered T cells. In some embodiments, the genetically engineered T cells comprise T cells that have been modified by the introduction of therapeutic TCR genes. The term "therapeutic TCR genes" can refer to specific combinations of TCRα and TCRβ chains that mediate a desired functionality, for example, being able to facilitate a host's immune system to fight against a disease.

Approaches based on currently available technologies for the detection of TCR-modified T cells have various drawbacks. Typically, TCR protein expression in TCR-modified T cells is detected by MHC multimers or TCR V domain-specific antibodies (Altman et al. Science 2006; Faint et al. J Immunol Methods 1999). In addition, TCR Cβ domain-specific antibodies have been used as pan-αβTCR antibodies (clone IP26; Schober et al. Nat Biomed Eng 2019), or to detect TCRs containing the human TRBC1 domain (clone JOVI-1; Maciocia et al. Nat Med 2017) or murine Trbc1/2 domains (clone H57; Mall et al. Cancer Res 2016). However, MHC multimers need to be specifically generated for each TCR specificity, which depending on the HLA-allele restriction are not available for certain TCRs; TCR V domain-specific antibodies are only available for certain TCR V domains; TCR V domain-specific antibodies and TCR Cβ domain-specific antibodies cannot be used if the TCR-modified T cells are present in a pool among other T cells that utilize the same TCR V domain or TCR Cβ domain. In addition, the use of fully murine TCR constant domains is undesirable due to possible immunogenicity of large murine protein sequences; furthermore, a therapeutic TCR gene construct based on fully murine TCR constant domains cannot be integrated in-frame in human TCRα or TCRβ constant loci and requires the co-delivery of an exogenous polyA signal for efficient expression. Consequently, the gene template needed for fully murine TCR constant domains will increase in size, possibly negatively impacting gene delivery efficiency when a site-specific knock-in approach is utilized.

Similarly, approaches based on currently available technologies for the isolation of TCR-modified T cells have various drawbacks. Such approaches utilize any antibody-based isolation method (e.g. utilizing flow cytometry or magnetic bead-based isolation). Most commonly, isolation of TCR-modified T cells is performed by MHC multimer-based reagents (Knabel et al. Nat Med 2002). As discussed above, MHC multimers need to be specifically generated for each TCR specificity, which depending on the HLA-allele restriction are not available for certain TCRs. Other isolation methods include:

the use of antibody epitopes placed in the TCR antigen-binding domain (e.g. described by Kieback et al. PNAS 2008). Addition or modification of amino acids can be assumed to interfere with TCR antigen fine specificity and TCR sensitivity as it may alter the structure of the binding domain. Hence, this concept requires feasibility studies for each individual TCR and will likely impact antigen binding for some TCRs.

the use of TCR V domain or human TRBC1-specific antibodies. Also as discussed above, such reagents are only available for certain TCR V domains and cannot be used if the TCR-modified T cells are present in a pool among other T cells that utilize the same TCR V domain or human TRBC1.

the use of cell surface marker proteins that are expressed in conjunction with the therapeutic TCR gene, e.g. the co-expression of a truncated LNGFR or EGFR protein. However, the inclusion of such cell surface markers increases the size of the transgene, which can impair the efficiency of the genetic engineering and subsequent transgene expression as well as enhance the immunogenicity of the engineered T cells.

In addition, approaches based on currently available technologies for the depletion of TCR-modified T cells also have various drawbacks. A number of 'safety switches' have been described for adoptive T cell therapy, including TCR and CAR therapy. Described systems include:

the use of antibody epitopes placed in the TCR antigen-binding domain (e.g. described by Kieback et al. PNAS 2008). This concept needs to be tested for each individual TCR and will likely impact antigen binding for a fraction of TCRs.

the use of additional transgenes, such as Herpes Simplex Virus TK (Bonini et al. Science 1997; Ciceri et al. Lancet Oncol 2009) or inducible Caspase-9 (Straathof et al. Blood 2005; Di Stasi et al. N Engl J Med 2011), which can be selectively activated in vivo. However, the inclusion of such markers increases the size of the transgene that needs to be delivered into the cells, which can impair the efficiency of the genetic engineering and subsequent transgene expression.

In comparison to currently available technologies, some embodiments provided herein can offer one or more of the following advantages:

1. Reduced immunogenicity: some embodiments introduce a limited number of amino acid changes into the human TRBC domain. A fully murine Trbc2 gene as described by Cohen et al. Cancer Res 2006 contains 33 foreign amino acids compared to the human TRBC2 gene. In contrast, a murine epitope-containing TRBC2 gene as described in some embodiments contains only 10 or fewer foreign amino acids, such as 9, 8, 7, 6, 5, 4, 3, or 2 amino acids that are not human but are murine.

2. Broad and generic utility for all human TCRs: unlike alternative technologies such as TCR V domain-specific antibodies, MHC multimers or TCR frame-work modifications, some embodiments described herein can be used for all TCRs independent of their TCR V domain usage, MHC-restriction and antigen-specificity.

3. Highly specific detection: some embodiments allow highly specific detection of TCR-modified T cells even in the absence of genetic knock-out of the endogenous TCR chains. Alternative technologies, such as TCR V domain- and human TRBC1-specific antibodies may specifically react with a sizeable fraction of endogenous TCR chains preventing accurate detection and specific isolation or depletion of TCR-modified T cells.

4. Allows in-frame exonic knock-in of therapeutic TCR genes into the human TCR locus: For example, TCRα locus knock-in of a therapeutic TCR construct utilizing a fully murinized Trbc gene as described by Schober et al (Nat Biomed Eng 2019) requires the co-delivery of a fully murinized Trac gene and a Bovine Growth Hormone poly(A) sequence for exogenous transcriptional termination. In contrast, TCRβ chains utilizing a murine epitope-containing TRBC2 gene as described in some embodiments can efficiently pair with fully human TCRα chains and therefore are compatible with in-frame exonic TCRα locus knock-in and endogenous transcriptional termination. This means that the therapeutic gene construct decreases by ~500 bp in size, which increases the efficiency of the genetic engineering process.

5. Avoids substantial increase in the size of the therapeutic TCR gene cassette: some embodiments are based on mutation of selected amino acids in the human TCR constant domain into their murine counterpart. Alternative technologies for detection, isolation and/or depletion of TCR-modified T cells include the use of additional proteins (e.g. truncated EGFR, truncated LNGFR, HSV-TK and inducible Caspase-9). Thereby, the size of the delivered transgene is increased, which can impair the efficiency of the genetic engineering and subsequent transgene expression. Furthermore, the inclusion of additional cell surface expressed proteins in the transgene may increase the immunogenicity of the engineered T cells.

In some embodiments, the T cells that have been modified by the introduction of therapeutic TCR genes are used for cancer treatment. In some embodiments, the cancers are solid tumors. Therapeutic TCR genes can be selected from in vitro mutated TCR chains expressed as recombinant TCR libraries by phage-, yeast- or T cell-display systems. Therapeutic TCR genes can also refer to neo-antigen-specific TCR genes from tumor biopsies on an individual patient basis. Following their identification, such neo-antigen TCR genes are then introduced into patient T cells via genetic engineering, thereby redirecting the antigen specificity of the T cells towards tumor neo-antigens. Finally, the genetically engineered T cells are administered back to the patient via intravenous infusion to treat those cancers. These embodiments can be applied to all cancers that are eligible for engineered adoptive T cell therapy.

In some embodiments, to make a marked protein in a therapeutic TCR gene construct, a murine epitope is introduced into the human TCR Cβ domain to allow detection of the introduced TCR in a genetically engineered T cell by the anti-mouse TCR Cβ antibody H57. H57 is an antibody that was first described in Kubo et al, J Immunol 1989. In some embodiments, H57-597 is used. H57-597 is a hamster mAb directed to an epitope of the C region of TCR β chain. The H57-597 antibody does not cross-react with γ/δ TCR-bearing T cells. Immobilized or soluble H57-597 antibody can activate α/β TCR-bearing T cells. Some embodiments described herein relate to a marked protein used for the detection, isolation, or depletion of genetically engineered T cells that have been modified by the introduction of therapeutic TCR genes, wherein the marked protein is derived from the murine TCR Cβ domain and introduced into the human TCR Cβ2 domain by mutation of existing amino acids within the human TCR Cβ2 domain.

In some embodiments a marked protein is provided for the detection, isolation or depletion of a cell modified with a novel TCR gene for the treatment of cancer, comprising the marked protein of any one of the embodiments provided herein.

Some embodiments relate to a kit used for detection, isolation or depletion of genetically engineered cells having the marked protein of any one of the above embodiments, comprising an antibody or binding agent that recognizes the marked protein. In some embodiments, the kit includes magnetic beads linked to the H57 antibody, which can be used to isolate or deplete T cells expressing the murine epitope-containing TCRβ chain. In some embodiments, the kit includes staining agents for detecting genetically engineered cells in tissue. In some embodiments, the genetically engineered cells comprise T cells. In some embodiments, the T cells have been modified by the introduction of therapeutic TCR genes. In some embodiments, the T cells that have been modified by the introduction of therapeutic TCR genes are used for cancer treatment.

Various Embodiments Relating to a Marked Protein Used for Targeted Delivery

Some embodiments relate to a marked protein used for targeted delivery of one or more payloads to genetically engineered cells expressing such a marked protein, comprising the marked protein of any one of embodiments described herein.

In some embodiments, the delivery of one or more payloads is achieved by conjugation to an antibody, an antibody mimetic protein or any other antigen-binding scaffold. In some embodiments, the delivery of one or more payloads is achieved by conjugation to the H57 antibody.

In some embodiments, the delivered payload is a protein, a small molecule, a nucleic acid, a liposome, or a nanoparticle. In some embodiments, the payload is a bi- or tri-specific antibody.

In some embodiments, the delivered payload is a cytokine. In some embodiments, the delivered payload is selected from the group of IL-1β, IL-2, IL-4, IL-6, IL-7, IL-10, IL-12, IL-15, IL-17, IL-18, IL-21, IL-23, IL-27, IFN-α, IFN-β, IFN-γ, and TNF-4α. In some embodiments, the cytokine is modified in its sequence in order to modulate interaction with its natural receptor molecule.

In some embodiments, the payload is an agonist or antagonist for a receptor molecule expressed by T cells. In some embodiments, the agonist binds to CD27, CD28, CD137 or CD278. In some embodiments, the antagonist binds to TGF-beta Receptor, PD-1, CTLA-4, Vista, steroid receptor or $A_1$-, $A_{2A}$-, $A_{2B}$- or $A_3$-adenosine receptor.

In some embodiments, the payload is a small molecule that modulates activation, differentiation, proliferation, survival or effector function of T cells. In some embodiments, the small molecule inhibits signaling of either TGF-beta Receptor, PD-1, CTLA-4, Vista, steroid receptor or $A_1$-, $A_{2A}$-, $A_{2B}$- or $A_3$-adenosine receptor.

In some embodiments, the payload is a nucleic acid that modulates T cell activation, differentiation, proliferation, survival or effector function. In some embodiments, the nucleic acid comprises a miRNA, shRNA or siRNA.

Some embodiments relate to a method for targeted delivery of one or more payloads to genetically engineered cells expressing a marked protein. The method includes a) obtaining a conjugate comprising the one or more payloads and a binding agent, wherein the binding agent specifically binds to the marked protein, and b) contacting the genetically engineered cells with the conjugate.

In some embodiments, the binding agent is an antibody, an antibody mimetic protein, or any other antigen-binding scaffold.

In some embodiments, the one or more payloads is a protein, a small molecule, a nucleic acid, a liposome, or a nanoparticle.

As appreciated herein, approaches based on currently available technologies for targeted delivery of payloads to engineered T cells can have various drawbacks. Most approaches either target mouse T cells or non-engineered human T cells using antibodies that bind endogenous markers present on the cell surface (e.g. CD3e or PD-1). Some research describes the targeting of fluorescent liposomes to adoptively transferred mouse T cells using an anti-Thy1.1 F(ab')₂ fragment conjugated to a PEGylated liposome labeled with the fluorescent lipophilic tracer dye DiD (Zheng et al., J Control Release, 2013). Another research describes the targeting of TGFβ receptor inhibition to adoptively transferred mouse T cells using an anti-Thy1.1 F(ab')₂ fragment conjugated to a PEGylated liposome loaded with the TGFβR1 inhibitor SB525334 (Zheng et al., ACS Nano, 2017). Another describes the targeting of TGFβ receptor inhibition to mouse T cells using an anti-PD-1 F(ab')₂ fragment conjugated to a PEGylated PLGA-based nanoparticle loaded with the TGFβR1 inhibitor SD-208 (Schmid et al., Nat Commun, 2017). Another describes the targeting of CAR DNA constructs to mouse T cells using an anti-CD3εF (ab')₂ fragment conjugated to a nanoparticle loaded with two DNA plasmids, one encoding a CD19 CAR gene flanked by piggyBac inverted repeats and one encoding the hyperactive piggyBac iPB7 transposase gene (Smith et al., Nature Nanotech, 2017). Another describes the targeting of transcription factor mRNA to human T cells using an anti-CD3ε antibody conjugated to a nanoparticle loaded with mRNA encoding the Foxo1$_{3A}$ variant transcription factor (Moffett et al., Nat Commun, 2017). Still another describes the targeting of TGFβ receptor inhibition to mouse T cells using an anti-CD8α VHH nanobody conjugated to an amphiphilic gold nanoparticle loaded with the TGFβR1 inhibitor SB525334 (Yang et al., Biomater Sci, 2019). However, these technologies do not provide a solution for the targeted delivery of payloads to engineered human T cells used in adoptive T cell therapy.

Some technologies allow for the targeting of IL-2 cytokine activity to human T cells and NK cells using an anti-PD-1 antibody fused to a mutant IL-2 polypeptide (IL2v) that has been engineered to bind to IL-2Rβγ, but not to IL-2Rα (WO/2018/184964, 2018). Other research describes the targeting of type I interferon cytokine activity to mouse T cells and cDC1 DCs using an anti-CD8α antibody fused to a mutant human IFN-α that has been engineered to be ~100-fold less active on mouse cells than WT mouse IFN-α (Huyghe et al., EMBO Mol Med, 2020). Another describes the targeting of IL-21 cytokine activity to human T cells using an anti-PD-1 antibody fused to a mutant IL-21 polypeptide that has been engineered to be >1000-fold less active than free WT IL-21 (Shen et al., Front Immunol, 2020). However, these technologies do not provide a solution for the targeted delivery of cytokine activity to engineered human T cells used in adoptive T cell therapy.

Some research targets engineered human CAR T cells using a DARPin® that binds to the introduced truncated HER2 marker gene. This involves the targeting of IL-2 and IL-15 cytokine activity to human CAR T cells expressing truncated HER2 as a transduction marker gene, using the anti-HER2 DARPin® G3 fused to Neo-2/15, an IL-2 and IL-15 mimetic that has been engineered to bind to IL-2Rβγ, but not to IL-2Rα (Leung et al., AACR 2020 Abstract #2222, 2020). However, this does not provide a solution for the targeted delivery of cytokine activity to engineered human T cells used in adoptive T cell therapy in which no additional marker gene is co-delivered besides the therapeutic TCR or CAR gene.

Some embodiments described herein can overcome one or more of the drawbacks described above. Various embodiments described herein target engineered human T cells without the need to introduce an additional marker gene, hence do not have to increase the size of the therapeutic gene cassette, which maximizes gene editing efficiencies.

In some embodiments, the TCR Cβ domain murine epitope embodiments distinguish themselves from the above in the sense that one can target engineered human T cells without the need to introduce an additional marker gene, hence one does not have to increase the size of the therapeutic gene cassette, which assists in gene editing efficiencies.

Various Embodiments Relating to a 2A Peptide Epitope

Some embodiments relate to an antibody epitope that can be inserted or made part of a TCR chain. In some embodiments, the epitope can be used for the detection of genetically engineered cells expressing such an antibody epitope, wherein the antibody epitope is attached to a TCR chain or a Chimeric Antigen Receptor. In some embodiments, the genetically engineered cells comprise a nucleotide construct encoding a peptide comprising the antibody epitope. In some embodiments, detection of the genetically engineered cells is based on antibody staining that can be detected by flow cytometry. The antibody can specifically bind and recognize the antibody epitope.

As shown in FIG. 2A-2D, in some embodiments, the antibody epitope is attached to the C-terminus or the N-terminus of a TCR chain, which can be either a constant or variable chain. In other embodiments, the antibody epitope is inserted into a TCR chain. In some embodiments, the antibody epitope is used to connect TCRα and TCRβ chains. In some embodiments, the position of the antibody epitope depends on the expression order of the TCR chains. Some embodiments can include genes other than TCR that encode proteins containing an antibody epitope sequence. Examples include Chimeric Antigen Receptor (CAR) transgenes that are fused to a second transgene, e.g. to modulate T cell function. Some embodiments can include more than one antibody epitope. Some embodiments can have 2, 3, 4, 5, 6, 7, 8, 9, or 10 antibody epitopes, where the antibody epitopes can be the same or different. Any antibody epitope can be used in these embodiments as long as there is an antibody that can specifically detect the epitope. In some embodiments, the antibody used is compatible with use in flow cytometry. In some embodiment the antibody epitope is attached to the C-terminus of the TCR constant domain and hence located intracellularly thereby reducing immunogenicity as the antibody epitope is not accessible for antibody-mediated immune responses. In some embodiments, the antibody epitope is attached to the TCR constant domain to avoid interference with TCR specificity and sensitivity.

In some embodiments, the genetically engineered cells comprise T cells. In some embodiments, the T cells have been modified by the introduction of therapeutic TCR or CAR genes. In some embodiments, the T cells that have been modified by the introduction of therapeutic TCR or CAR genes are used for cancer treatment. The term "therapeutic TCR genes" can refer to specific combinations of TCRα and TCRβ chains that mediate a desired functionality, for example, being able to facilitate a host's immune system to fight against a disease.

In some embodiments, the antibody epitope comprises a 2A peptide sequence, a HA.11 epitope tag, a FLAG epitope tag, a Myc epitope tag, or a V5 epitope tag. These epitope tags can be specifically detected using a flow cytometry-compatible antibody. In some embodiments, the antibody epitope comprises a peptide comprising up to the same number of amino acids as the 2A peptide. A skilled person in the art understands that any epitope tags, as long as they comprise up to the same number of amino acids as the 2A peptide, may be used in making the antibody epitope.

2A peptides, or 2A self-cleaving peptides, are a class of 18-22 aa-long peptides, which are derived from viruses.

Four members of the 2A peptides family are frequently used in life science research. They are P2A, T2A, E2A, or F2A. P2A is derived from porcine teschovirus-1 2A; T2A is derived from thosea asigna virus 2A; E2A is derived from equine rhinitis A virus; F2A is derived from foot-and-mouth disease virus 18.

In some embodiments, the 2A peptide can be P2A, T2A, E2A, or F2A. In some embodiments the 2A peptide serves a dual purpose: first it allows to link expression of two protein sequences; and second it allows for the detection of at least one of the two protein sequences. As used herein, "gene" when used in reference to encoding one of the peptides, such as the 2A peptide, denotes a nucleotide sequence that encodes for the peptide (the 2A peptide, for example). It is not meant to denote a naturally occurring gene arrangement, but as a shorthand for the nucleic acid sequence that encodes for the relevant peptide.

In some embodiments, the antibody epitope comprises a 2A peptide sequence fragment or a sequence at least 90% identical thereto, wherein the 2A peptide sequence is not a full 2A sequence.

In some embodiments, the peptide sequence comprises a sequence of SEQ ID NO: 1 (CGDVEENPG). In some embodiments, the peptide sequence comprises a sequence of SEQ ID NO: 6 (GDVEENPG). In some embodiments, the peptide sequence comprises a sequence of SEQ ID NO: 7 (GDVESNPG). In some embodiments, the peptide sequence comprises a sequence which is at least 75% identical to SEQ ID NO: 1.

In some embodiments, the antibody epitope can be identified by the monoclonal anti-2A peptide antibody 3H4. 3H4 is a recently developed antibody by Novus Biologicals. It can be used in western blotting (Yu et al. Viruses 2020), immunoprecipitation, and immunocytochemistry/immunofluorescence.

Some embodiments relate to an antibody epitope used for the detection of genetically engineered T cells that have been modified by the introduction of therapeutic TCR genes, comprise the antibody epitope of any one of above embodiments.

Some embodiments relate to an antibody epitope for the detection of a cell modified with a novel TCR or CAR gene for the treatment of cancer, comprise the antibody epitope of any one of above embodiments.

Some embodiments relate to a kit used for detection of genetically engineered cells expressing the antibody epitope of any one of above embodiments. In some embodiments, the genetically engineered cells comprise T cells. In some embodiments, the T cells have been modified by the introduction of therapeutic TCR genes. In some embodiments, the T cells that have been modified by the introduction of therapeutic TCR genes are used for cancer treatment. In some embodiments, the kit includes an antibody or binding agent that specifically binds to the antibody epitope. In some embodiments, the antibody or binding agent can include a fluorescent or detectable marker.

Some embodiments relate to a genetic construct comprising a gene capable of expressing a 2A peptide sequence or a sequence that is at least 90% identical thereto, wherein the construct is configured for the expression of multiple proteins from a single open reading frame, and wherein the gene does not increase the size of the genetic construct by more than 25 amino acids.

In some embodiments, the 2A peptide sequence comprises a 2A peptide sequence fragment or a sequence at least 90% identical thereto. The 2A peptide sequence is not a full 2A sequence. In some embodiments, the 2A peptide sequence comprises a sequence of SEQ ID NO: 2, SEQ ID NO: 3, SEQ ID NO: 6, or a sequence at least 75% identical to SEQ ID NO: 2, SEQ ID NO: 3, or SEQ ID NO: 6. (SEQ ID NO: 2=EGRGSLLTCGDVEENPGP; SEQ ID NO: 3=ATNFSLLKQAGDVEENPGP; SEQ ID NO: 6=GDVEENPG).

In cell therapy using genetically engineered T cells, the antigen specificity of such T cells has to be redirected. To redirect the antigen specificity of T cells, both an exogenous TCRα and TCRβ chain sequence should be introduced. Therefore, to maximize the genetic engineering efficiency, a therapeutic TCR gene construct should facilitate the simultaneous expression of two TCR genes. One way to achieve this is by using 2A self-cleaving peptide sequences, which allows the co-expression of two proteins at an equimolar ratio from a single open reading frame (Ryan and Drew. EMBO J 1994). Notably, 2A peptide-based TCR transgenes display increased expression and functionality compared to IRES-based TCR transgenes (Leisegang et al. J Mol Med 2008), presumably due to enhanced pairing of the introduced TCR chains.

In some embodiments, in the therapeutic TCR gene construct, the TCRα and TCRβ chain are co-expressed using an intervening epitope (e.g., marker or label) sequence, such as the 2A peptide sequence, that is covalently attached to the TCR Cα or TCR Cβ domain (depending on the order of expression). Since 2A peptide sequences are normally not present in mammalian cells, such peptides could serve as protein markers to track the genetically engineered T cells. To discriminate engineered T cells from unmodified T cells, antibody reagents can be used that can detect the engineered T cells at a single cell level. A flow cytometry-based staining procedure has been generated in which therapeutic TCR genes can be detected using the monoclonal anti-2A peptide antibody 3H4. Since the 2A peptide marker is covalently attached to the intracellular domain of the TCRβ chain, it is important that this staining procedure is carried out in membrane permeabilized cells. These 2A peptide-linked TCRβ chains allow efficient detection of TCR-modified T cells using the 3H4 antibody, with very little background signal stemming from wildtype T cells. Furthermore, these 2A peptide-linked TCRβ chains are compatible with the in-frame exonic knock-in of therapeutic TCR genes into the human TCR locus.

In comparison to currently available technologies, a protein marker based on the antibody epitope according to various embodiments described herein for the detection, isolation, or depletion of TCR-modified T cells offers the following advantages: (a) does not increase the size of the therapeutic gene construct by more than 25 amino acids, (b) has minimal immunogenicity, (c) can be used for every therapeutic TCR gene without a requirement for optimization depending on the antigen-specificity of the TCR, and (d) is compatible with the use of fully human TCR constant domains. Due to its intracellular location, this marker is suitable to detect, but not isolate or deplete T cells engineered to express a therapeutic TCR.

More specifically, for the antibody epitope comprising a 2A peptide epitope, some advantages over currently available technologies can include, in some embodiments, one or more of the following:

1. Reduced immunogenicity: the disclosed invention introduces a limited number of amino acid changes compared to alternative technologies such as fully murine TCR constant domains. Of note, although 2A peptide sequences are virus-derived, they do not appear to induce immune responses in immunocompetent individuals (Arber et al, Gene Ther 2013).

2. Broad and generic utility for all human TCRs; can be used for every therapeutic TCR gene without a requirement for optimization depending on the antigen-specificity of the TCR.

3. Highly specific detection, details can be found in examples 3 and 4.

4. Allows in-frame exonic knock-in of therapeutic TCR genes into the human TCR locus.

5. Avoids substantial increase of the therapeutic TCR gene cassette; the addition of a 2A peptide does not substantially alter the size of a transgene because the 2A peptide is small. This is important because a larger transgene typically leads to lower integration efficiency and higher DNA toxicity during gene delivery.

Some embodiments relate to a genetically engineered cell expressing the marked protein of any one of the preceding embodiments. Some embodiments relate to a genetically engineered cell expressing the antibody epitope of any one of the preceding embodiments. Some embodiments relate to a genetically engineered cell containing the genetic construct of any one of the preceding embodiments.

The marked protein or antibody epitope may be introduced into any suitable cells. Suitable cells include, without limitation, mammalian cells, insect cells, yeast, and bacteria. In some embodiments, suitable carriers include viruses, yeast, bacteria, and phage. While the present disclosure uses the term "cells" throughout for simplicity, it is contemplated herein that all such disclosures of "cells" herein, includes not just various forms of T cells (such as immortalized T cells), yeast and bacteria, but can also be more generically used with any carrier, including viruses and phage. Accordingly, the disclosure around "cells" as used herein (with reference to cells into which a combinatorial library may be introduced), can include eukaryotic cells, prokaryotic cells, and to denote an option where viruses and phages can also be employed as carriers. The cells can be a cell line, immortalized cells, or primary cells. In some embodiments, the cells are human cells, or are derived from a human cell. In some embodiments, the population of cells comprises immortalized T cells or primary T cells. In some embodiments, the cells are engineered, e.g., genetically modified, to reduce or eliminate endogenous or background expression of the functional property by the cells. In some embodiments, the cells are engineered, e.g., genetically modified, to enhance the ability of the cells to exhibit the functional property when introduced with the marked protein or antibody epitope. In some embodiments, the cells are engineered, e.g., genetically modified, to promote growth and/or maintenance of the population in culture. In some embodiments, the cells of the population do not comprise an endogenous polypeptide conferring the at least one functional property to the cells. In some embodiments, the cells are genetically modified to introduce or enhance or eliminate or reduce expression of one or more of CD4, CD8 and CD28. In some embodiments, the genetically modified cells are T cells.

Some data that support various embodiments described herein are shown in FIGS. 3-9. In these and other embodiments, the sequences listed in Table 1 may be useful. FIGS. 10-17 also depict various sequences from the below table.

TABLE 1

| Sequence Description | Sequence | SEQ ID NO: |
|---|---|---|
| Immunogen used to raise 2A peptide antibody | CGDVEENPG | 1 |
| T2A peptide sequence | EGRGSLLTCGDVEENPGP | 2 |
| P2A peptide sequence | ATNFSLLKQAGDVEENPGP | 3 |
| Human TCR Cβ2 domain containing the murine TCR epitope detectable by the H57 antibody | XDLRNVFPPKVAVFEPSE AEISHTQKATLVCLATGF YPDHVELSWWVNGKEVH SGVSTDPQPLKEQPALND SRYCLSSRLRVSATFWQN PRNHFRCQVQFYGLSEND KWPEGSAKPVTQIVSAEA WGRADCGFTSESYQQGV LSATILYEILLGKATLYAV LVSALVLMAMVKRKDSR G | 4 |
| Human TCR Cβ2 domain linked to the T2A peptide epitope detectable by the 3H4 antibody | XDLKNVFPPKVAVFEPSE AEISHTQKATLVCLATGF YPDHVELSWWVNGKEVH SGVSTDPQPLKEQPALND SRYCLSSRLRVSATFWQN PRNHFRCQVQFYGLSEND EWTQDRAKPVTQIVSAEA WGRADCGFTSESYQQGV LSATILYEILLGKATLYAV LVSALVLMAMVKRKDSR GGSGEGRGSLLTCGDVEE NPGP | 5 |
| A fragment of a T2A or P2A peptide sequence | GDVEENPG | 6 |
| A fragment of a E2A or F2A peptide sequence | GDVESNPG | 7 |
| Human TCR Cβ2 domain [UniProt A0A5B9] | XDLKNVFPPKVAVFEPSE AEISHTQKATLVCLATGF YPDHVELSWWVNGKEVH SGVSTDPQPLKEQPALND SRYCLSSRLRVSATFWQN PRNHFRCQVQFYGLSEND EWTQDRAKPVTQIVSAEA WGRADCGFTSESYQQGV LSATILYEILLGKATLYAV LVSALVLMAMVKRKDSR G | 8 |
| E2A peptide | QCTNYALLKLAGDVESNP GP | 9 |
| F2A peptide | VKQTLNFDLLKLAGDVES NPGP | 10 |
| Human TCR Cβ1 [UniProt P01850] | XDLNKVFPPEVAVFEPSE AEISHTQKATLVCLATGF FPDHVELSWWVNGKEVH SGVSTDPQPLKEQPALND SRYCLSSRLRVSATFWQN PRNHFRCQVQFYGLSEND EWTQDRAKPVTQIVSAEA WGRADCGFTSVSYQQGV LSATILYEILLGKATLYAV LVSALVLMAMVKRKDF | 11 |
| murine Trbc1 | XDLRNVTPPKVSLFEPSK AEIANKQKATLVCLARGF FPDHVELSWWVNGKEVH SGVSTDPQAYKESNYSYC LSSRLRVSATFWHNPRNH FRCQVQFHGLSEEDKWPE GSPKPVTQNISAEAWGRA DCGITSASYQQGVLSATIL YEILLGKATLYAVLVSTL | 12 |

TABLE 1-continued

| Sequence Description | Sequence | SEQ ID NO: |
|---|---|---|
| | VVMAMVRNR | |
| murine Trbc2 | XDLRNVTPPKVSLFEPSK AEIANKQKATLVCLARGF FPDHVELSWWVNGKEVH SGVSTDPQAYKESNYSYC LSSRLRVSATFWHNPRNH FRCQVQFHGLSEEDKWPE GSPKPVTQNISAEAWGRA DCGITSASYHQGVLSATIL YEILLGKATLYAVLVSGL VLMAMVKKKNS | 13 |
| huTRBC1-muFG | EDLNKVFPPEVAVFEPSE AEISHTQKATLVCLATGF FPDHVELSWWVNGKEVH SGVSTDPQPLKEQPALND SRYCLSSRLRVSATFWQN PRNHFRCQVQFYGLSEED KWPEGSPKPVTQIVSAEA WGRADCGFTSVSYQQGV LSATILYEILLGKATLYAV LVSALVLMAMVKRKDF | 14 |
| huTRBC2-muABFG ("mur10") | EDLRNVTPPKVAVFEPSE AEISHTQKATLVCLATGF FPDHVELSWWVNGKEVH SGVSTDPQPLKEQPALND SRYCLSSRLRVSATFWQN PRNHFRCQVQFYGLSEED KWPEGSPKPVTQIVSAEA WGRADCGFTSESYQQGV LSATILYEILLGKATLYAV LVSALVLMAMVKRKDSR G | 15 |
| huTRBC2-muABFG R4K | EDLKNVTPPKVAVFEPSE AEISHTQKATLVCLATGF FPDHVELSWWVNGKEVH SGVSTDPQPLKEQPALND SYCLSSRLRVSATFWQN PRNHFRCQVQFYGLSEED KWPEGSPKPVTQIVSAEA WGRADCGFTSESYQQGV LSATILYEILLGKATLYAV LVSALVLMAMVKRKDSR G | 16 |
| huTRBC2-muABFG T7F | EDLRNVFPPKVAVFEPSE AEISHTQKATLVCLATGF FPDHVELSWWVNGKEVH SGVSTDPQPLKEQPALND SRYCLSSRLRVSATFWQN PRNHFRCQVQFYGLSEED KWPEGSPKPVTQIVSAEA WGRADCGFTSESYQQGV LSATILYEILLGKATLYAV LVSALVLMAMVKRKDSR G | 17 |
| huTRBC2-muABFG F37Y | EDLRNVTPPKVAVFEPSE AEISHTQKATLVCLATGF YPDHVELSWWVNGKEVH SGVSTDPQPLKEQPALND SRYCLSSRLRVSATFWQN PRNHFRCQVQFYGLSEED KWPEGSPKPVTQIVSAEA WGRADCGFTSESYQQGV LSATILYEILLGKATLYAV LVSALVLMAMVKRKDSR G | 18 |
| huTRBC2-muABFG E106N | EDLRNVTPPKVAVFEPSE AEISHTQKATLVCLATGF FPDHVELSWWVNGKEVH SGVSTDPQPLKEQPALND SRYCLSSRLRVSATFWQN | 19 |

21

TABLE 1-continued

| Sequence Description | Sequence | SEQ ID NO: |
|---|---|---|
| | PRNHFRCQVQFYGLSEND KWPEGSPKPVTQIVSAEA WGRADCGFTSESYQQGV LSATILYEILLGKATLYAV LVSALVLMAMVKRKDSR G | |
| huTRBC2-muABFG K108E | EDLRNVTPPKVAVFEPSE AEISHTQKATLVCLATGF FPDHVELSWWVNGKEVH SGVSTDPQPLKEQPALND SRYCLSSRLVSATFWQN PRNHFRCQVQFYGLSEED EWPEGSPKPVTQIVSAEA WGRADCGFTSESYQQGV LSATILYEILLGKATLYAV LVSALVLMAMVKRKDSR G | 20 |
| huTRBC2-muABFG P110T | EDLRNVTPPKVAVFEPSE AEISHTQKATLVCLATGF FPDHVELSWWVNGKEVH SGVSTDPQPLKEQPALND SRYCLSSRLVSATFWQN PRNHFRCQVQFYGLSEED KWTEGSPKPVTQIVSAEA WGRADCGFTSESYQQGV LSATILYEILLGKATLYAV LVSALVLMAMVKRKDSR G | 21 |
| huTRBC2-muABFG E111Q | EDLRNVTPPKVAVFEPSE AEISHTQKATLVCLATGF FPDHVELSWWVNGKEVH SGVSTDPQPLKEQPALND SRYCLSSRLVSATFWQN PRNHFRCQVQFYGLSEED KWPQGSPKPVTQIVSAEA WGRADCGFTSESYQQGV LSATILYEILLGKATLYAV LVSALVLMAMVKRKDSR G | 22 |
| huTRBC2-muABFG G112D | EDLRNVTPPKVAVFEPSE AEISHTQKATLVCLATGF FPDHVELSWWVNGKEVH SGVSTDPQPLKEQPALND SRYCLSSRLVSATFWQN PRNHFRCQVQFYGLSEED KWPEDSPKPVTQIVSAEA WGRADCGFTSESYQQGV LSATILYEILLGKATLYAV LVSALVLMAMVKRKDSR G | 23 |
| huTRBC2-muABFG S113R | EDLRNVTPPKVAVFEPSE AEISHTQKATLVCLATGF FPDHVELSWWVNGKEVH SGVSTDPQPLKEQPALND SRYCLSSRLVSATFWQN PRNHFRCQVQFYGLSEED KWPEGRPKPVTQIVSAEA WGRADCGFTSESYQQGV LSATILYEILLGKATLYAV LVSALVLMAMVKRKDSR G | 24 |
| huTRBC2-muABFG P114A | EDLRNVTPPKVAVFEPSE AEISHTQKATLVCLATGF FPDHVELSWWVNGKEVH SGVSTDPQPLKEQPALND SRYCLSSRLVSATFWQN PRNHFRCQVQFYGLSEED KWPEGSAKPVTQIVSAEA WGRADCGFTSESYQQGV LSATILYEILLGKATLYAV LVSALVLMAMVKRKDSR G | 25 |

22

TABLE 1-continued

| Sequence Description | Sequence | SEQ ID NO: |
|---|---|---|
| huTRBC2-mur7 | EDLRNVTPPKVAVFEPSE AEISHTQKATLVCLATGF YPDHVELSWWVNGKEVH SGVSTDPQPLKEQPALND SRYCLSSRLVSATFWQN PRNHFRCQVQFYGLSEND KWPEGSAKPVTQIVSAEA WGRADCGFTSESYQQGV LSATILYEILLGKATLYAV LVSALVLMAMVKRKDSR G | 26 |
| huTRBC2-mur6 | EDLRNVFPPKVAVFEPSE AEISHTQKATLVCLATGF YPDHVELSWWVNGKEVH SGVSTDPQPLKEQPALND SRYCLSSRLVSATFWQN PRNHFRCQVQFYGLSEND KWPEGSAKPVTQIVSAEA WGRADCGFTSESYQQGV LSATILYEILLGKATLYAV LVSALVLMAMVKRKDSR G | 27 |
| 1G4 alpha chain (full-length) | MKSLRVLLVILWLQLSW VWSQKQEVTQIPAALSVP EGENLVLNCSFTDSAIYN LQWFRQDPGKGLTSLLLI QSSQREQTSGRLNASLDK SSGRSTLYIAASQPGDSAT YLCAVRPLYGGSYIPTFG RGTSLIVHPYIQNPDPAVY QLRDSKSSDKSVCLFTDF DSQTNVSQSKDSDVYITD KTVLDMRSMDFKSNSAV AWSNKSDPACANAFNNSI IPEDTFFPSPESSCDVKLV EKSFETDTNLNFQNLSVIG FRILLLKVAGFNLLMTLR LWSS | 28 |
| 1G4 beta chain (full-length with TRBC2 constant domain) | MSIGLLCCAALSLLWAGP VNAGVTQTPKFQVLKTG QSMTLQCAQDMNHEYMS WYRQDPGMGLRLIHYSV GAGITDQGEVPNGYNVSR STTEDFPLRLLSAAPSQTS VYFCASSYVGNTGELFFG EGSRLTVLEDLKNVFPPK VAVFEPSEAEISHTQKATL VCLATGFYPDHVELSWW VNGKEVHSGVSTDPQPLK EQPALNDSRYCLSSRLRV SATFWQNPRNHFRCQVQ FYGLSENDEWTQDRAKP VTQIVSAEAWGRADCGFT SESYQQGVLSATILYEILL GKATLYAVLVSALVLMA MVKRKDSRG | 29 |
| 1G4 alpha variable region | MKSLRVLLVILWLQLSW VWSQKQEVTQIPAALSVP EGENLVLNCSFTDSAIYN LQWFRQDPGKGLTSLLLI QSSQREQTSGRLNASLDK SSGRSTLYIAASQPGDSAT YLCAVRPLYGGSYIPTFG RGTSLIVHP | 30 |
| 1G4 beta variable region | MSIGLLCCAALSLLWAGP VNAGVTQTPKFQVLKTG QSMTLQCAQDMNHEYMS WYRQDPGMGLRLIHYSV GAGITDQGEVPNGYNVSR STTEDFPLRLLSAAPSQTS VYFCASSYVGNTGELFFG | 31 |

TABLE 1-continued

| Sequence Description | Sequence | SEQ ID NO: |
|---|---|---|
| | EGSRLTVL | |
| H57 VH | EVYLVESGGDLVQPGSSL KVSCAASGFTFSDFWMY WVRQAPGKGLEWVGRIK NIPNNYATEYADSVRGRF TISRDDSRNSIYLQMNRLR VDDTAIYYCTRAGRFDHF DYWGQGTMVTVSS | 32 |
| H57 VL | YELIQPSSASVTVGETVKI TCSGDQLPKNFAYWFQQ KSDKNILLLIYMDNKRPS GIPERFSGSTSGTTATLTIS GAQPEDEAAYYCLSSYG DNNDLVFGSGTQLTVL | 33 |
| IL2v | APASSSTKKTQLQLEHLL LDLQMILNGINNYKNPKL TRMLTAKFAMPKKATEL KHLQCLEEELKPLEEVLN GAQSKNFHLRPRDLISNIN VIVLELKGSETTFMCEYA DETATIVEFLNRWITFAQS IISTLT | 34 |
| Native IL2 [UniProt P60568] | APTSSSTKKTQLQLEHLLL DLQMILNGINNYKNPKLT RMLTFKFYMPKKATELK HLQCLEEELKPLEEVLNL AQSKNFHLRPRDLISNINV IVLELKGSETTFMCEYAD ETATIVEFLNRWITFCQSII STLT | 35 |
| (G4S)3 linker | GGGGSGGGGSGGGGS | 36 |
| FLAG epitope | DYKDDDDK | 37 |
| Myc epitope | EQKLISEEDL | 38 |
| HA.11 epitope | YPYDVPDYA | 39 |
| V5 epitope | GKPIPNPLLGLDST | 40 |

FIG. 3 shows FACS analysis of human primary T cells with knock-in of the NY-ESO-1 1G4 TCR at the endogenous TRAC locus using various repair templates. huTRBC1, fully human TRBC1 sequence; muTrbc2, fully murine Trbc2 sequence without polyA signal; muTrbc2-BGHpA, fully murine Trbc2 sequence with BGH polyA signal; huTRBC1-muFG, human TRBC1 sequence with incorporation of the murine Trbc2 FG loop (predicted H57 binding epitope; Wang et al., EMBO J 1998). The human primary CD3$^+$ T cells were selected and activated with anti-CD3/CD28 beads for 2 days and then electroporated with a TRAC RNP and with a repair template to guide TCR knock-in. 5 days after electroporation, cells were harvested and analyzed by co-staining with an APC anti-mouse TCR Cβ chain antibody (clone H57-597, cat #109212, BioLegend) and a PE-Cy7 anti-human TCR Vβ13.1 antibody (clone H131, cat #362406, BioLegend). The data show that a polyA signal is useful for TCR expression when using a fully murine Trbc2 sequence, and that cells that express a fully murine Trbc2 sequence can be recognized by the H57 antibody. However, incorporation of the murine Trbc2 FG loop into the human TRBC1 sequence, while enabling TCR expression, is not sufficient for H57 antibody recognition.

Figure 4:
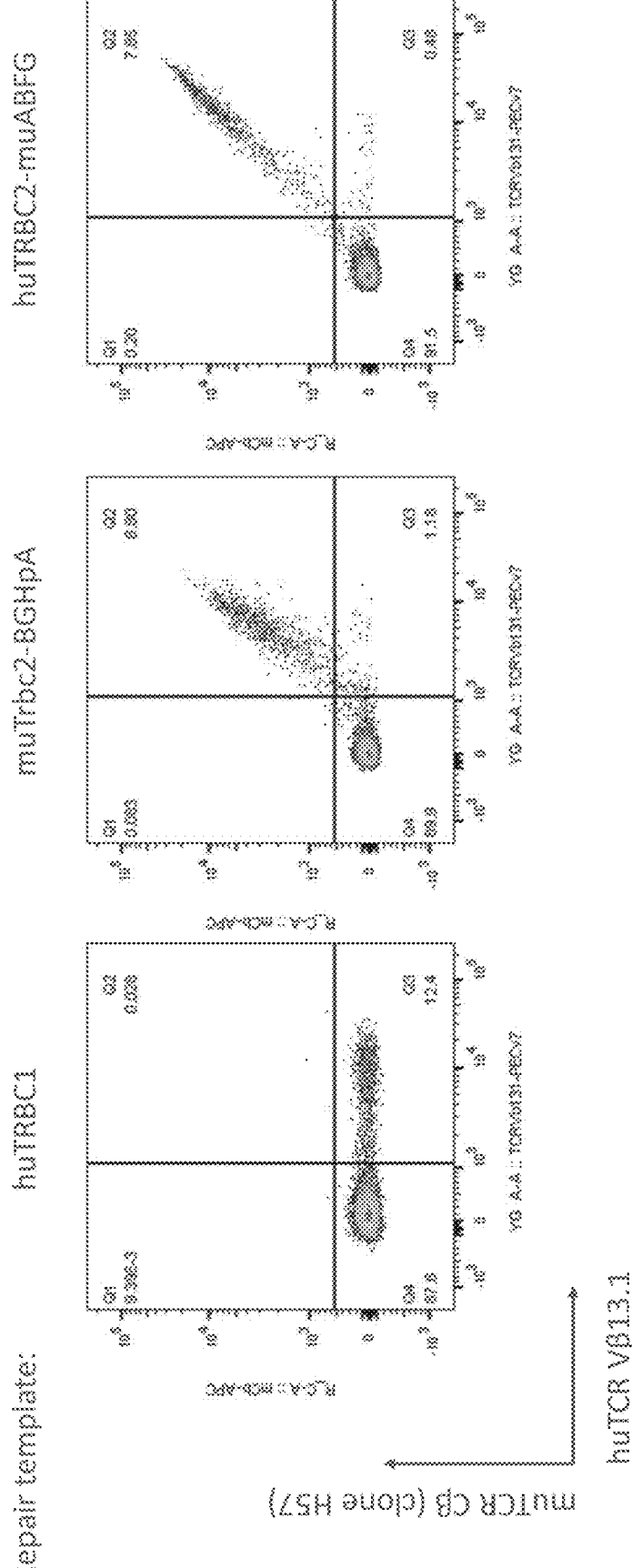
FIG. 4 shows FACS analysis of human primary T cells with knock-in of the NY-ESO-1 1G4 TCR at the endogenous TRAC locus using various repair templates. The data shows that incorporation of 10 amino acid residues from the murine Trbc2 A and B strand, and FG loop into the human TRBC2 sequence is sufficient to enable TCR expression and H57 antibody recognition.

FIG. 4 shows FACS analysis of human primary T cells with knock-in of the NY-ESO-1 1G4 TCR at the endogenous TRAC locus using various repair templates. huTRBC1, fully human TRBC1 sequence; muTrbc2-BGHpA, fully murine Trbc2 sequence with BGH polyA signal; huTRBC2-muABFG, human TRBC2 sequence with incorporation of 10 amino acid residues from the murine Trbc2 A and B strand, and FG loop (predicted H57 binding epitope; Wang et al., EMBO J 1998 and Sasada et al., J Exp Med 2002). The human primary CD3$^+$ T cells were selected and activated with anti-CD3/CD28 beads for 2 days and then electroporated with a TRAC RNP and with a repair template to guide TCR knock-in. 5 days after electroporation, cells were harvested and analyzed by co-staining with an APC anti-mouse TCR Cβ chain antibody (clone H57-597, cat #109212, BioLegend) and a PE-Cy7 anti-human TCR Vβ13.1 antibody (clone H131, cat #362406, BioLegend). The data show that incorporation of 10 amino acid residues from the murine Trbc2 A and B strand, and FG loop into the human TRBC2 sequence is sufficient to enable TCR expression and H57 antibody recognition (amino acid mutations being K4R, F7T, Y37F, N106E, E108K, T110P, Q111E, D112G, R113S, A114P).

Figure 5:
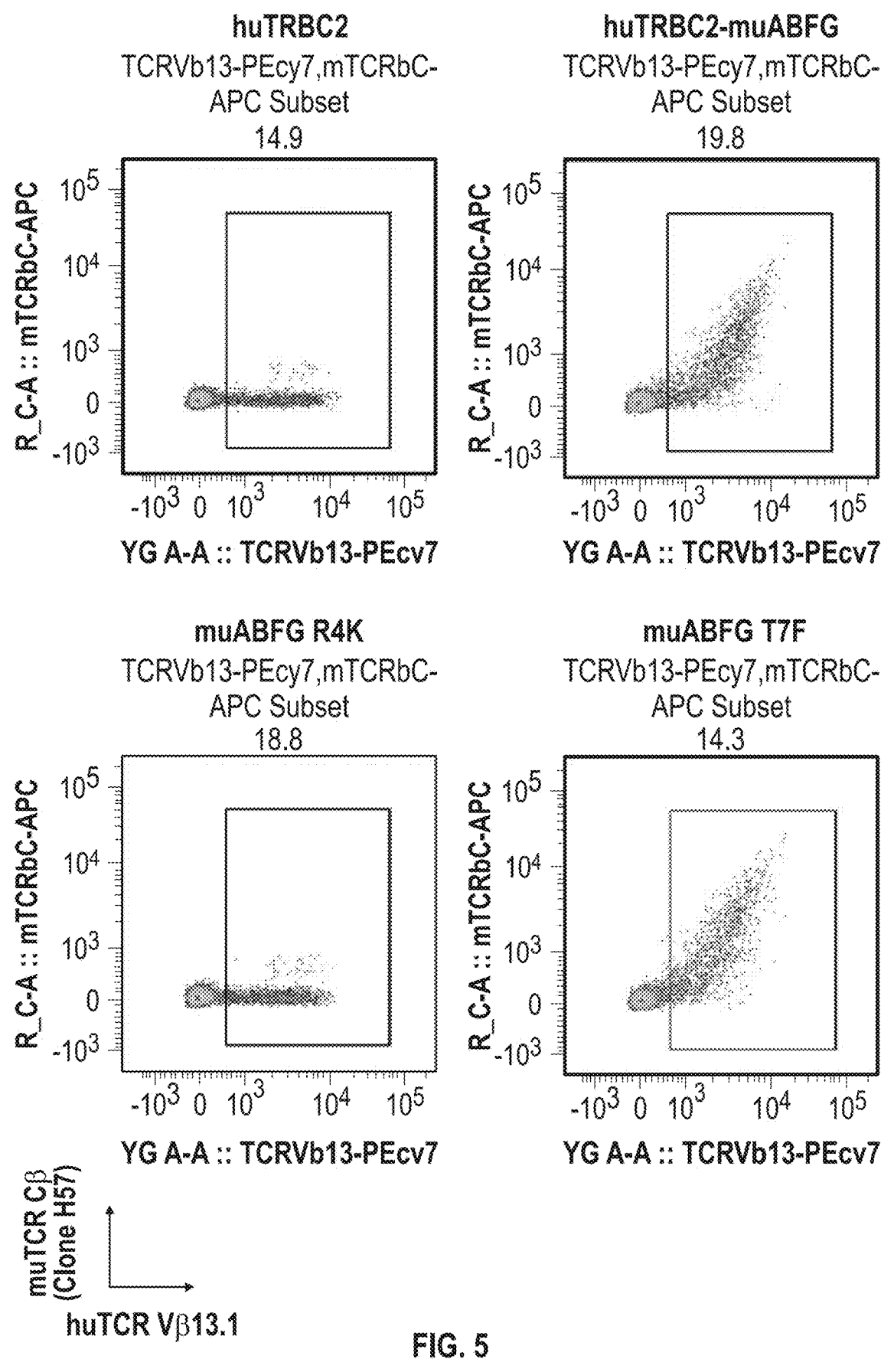
Figure 5:
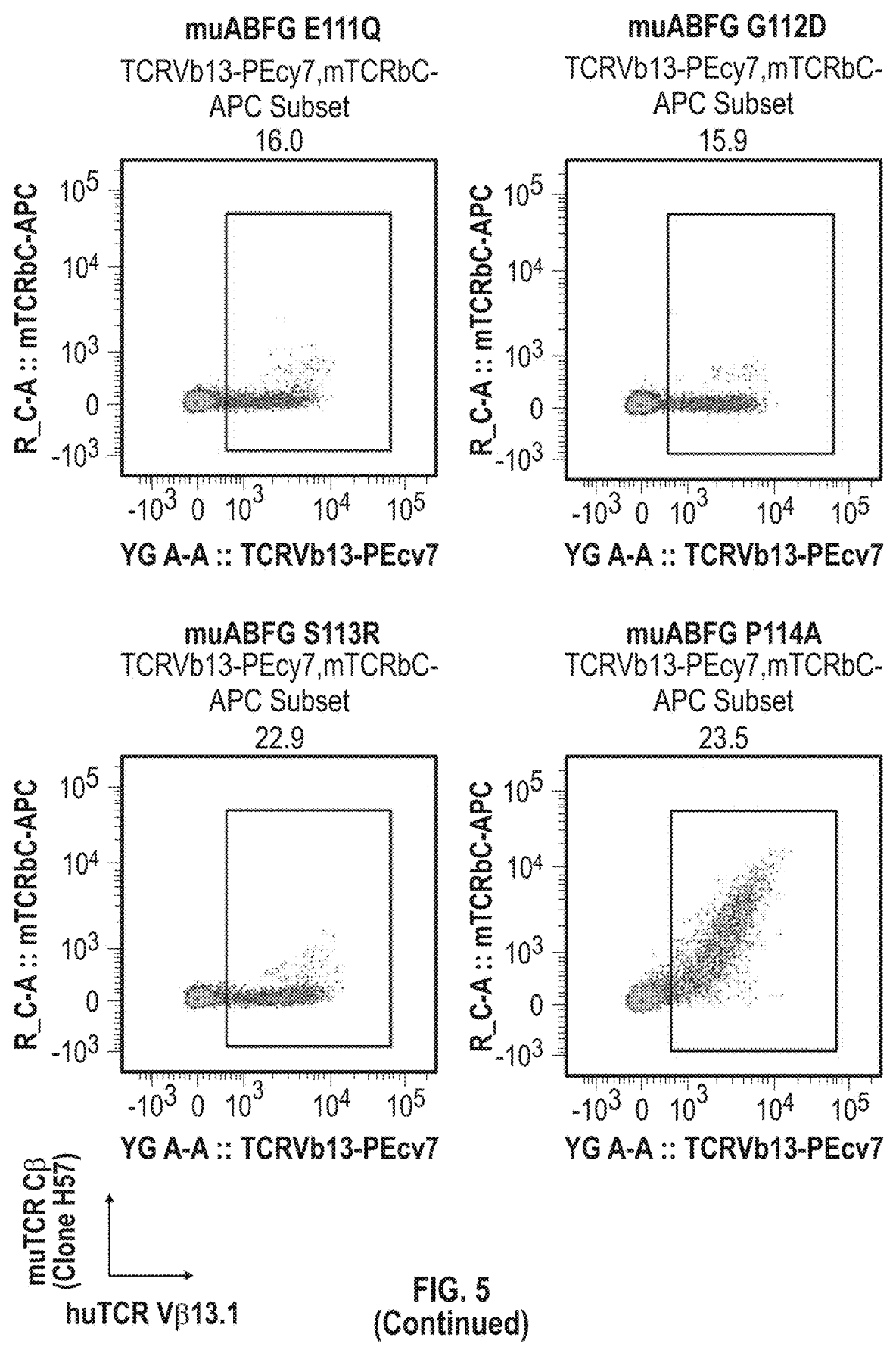

FIG. 5 shows FACS analysis of human primary T cells with knock-in of the NY-ESO-1 1G4 TCR at the endogenous TRAC locus using various repair templates. huTRBC2, fully human TRBC2 sequence; huTRBC2-muABFG, human TRBC2 sequence with incorporation of 10 amino acid residues from the murine Trbc2 A and B strand, and FG loop (predicted H57 binding epitope); muABFG R4K, human TRBC2 sequence with incorporation of 9 amino acid residues from the murine Trbc2 A and B strand, and FG loop, and 1 amino acid residue reverted back to the human counterpart (R4K) to map the minimal H57 binding epitope; muABFG T7F, human TRBC2 sequence with incorporation of 9 amino acid residues from the murine Trbc2 A and B strand, and FG loop, and 1 amino acid residue reverted back to the human counterpart (T7F) to map the minimal H57 binding epitope; muABFG F37Y, human TRBC2 sequence with incorporation of 9 amino acid residues from the murine Trbc2 A and B strand, and FG loop, and 1 amino acid residue reverted back to the human counterpart (F37Y) to map the minimal H57 binding epitope; muABFG E106N, human TRBC2 sequence with incorporation of 9 amino acid residues from the murine Trbc2 A and B strand, and FG loop, and 1 amino acid residue reverted back to the human counterpart (E106N) to map the minimal H57 binding epitope; muABFG K108E, human TRBC2 sequence with incorporation of 9 amino acid residues from the murine Trbc2 A and B strand, and FG loop, and 1 amino acid residue reverted back to the human counterpart (K108E) to map the minimal H57 binding epitope; muABFG P110T, human TRBC2 sequence with incorporation of 9 amino acid residues from the murine Trbc2 A and B strand, and FG loop, and 1 amino acid residue reverted back to the human counterpart (P110T) to map the minimal H57 binding epitope; muABFG E111Q, human TRBC2 sequence with incorporation of 9 amino acid residues from the murine Trbc2 A and B strand, and FG loop, and 1 amino acid residue reverted back to the human counterpart (E111Q) to map the minimal H57 binding epitope; muABFG G112D, human TRBC2 sequence with incorporation of 9 amino acid residues from the murine Trbc2 A and B strand, and FG loop, and 1 amino acid residue reverted back to the human counterpart (G112D) to map the minimal H57 binding epitope; muABFG S113R, human TRBC2 sequence with incorporation of 9 amino acid residues from the murine Trbc2 A and B strand, and FG loop, and 1 amino acid residue reverted back to the human counterpart (S113R) to map the minimal H57 binding epitope; muABFG P114A, human TRBC2 sequence with incorporation of 9 amino acid residues from the murine Trbc2 A and B strand, and FG loop, and 1 amino acid residue reverted back to the human counterpart (P114A) to map the minimal H57 binding epitope. The human primary CD3+ T cells were selected and activated with anti-CD3/CD28 beads for 2 days and then electroporated with a TRAC RNP and with a repair template to guide TCR knock-in. 5 days after electroporation, cells were harvested and analyzed by co-staining with an APC anti-mouse TCR Cβ chain antibody (clone H57-597, cat #109212, BioLegend) and a PE-Cy7 anti-human TCR Vβ13.1 antibody (clone H131, cat #362406, BioLegend). The data show that 6 amino acid residues from the murine Trbc2 A strand and FG loop are necessary to enable H57 antibody recognition (amino acids being R4, K108, P110, E111, G112, and S113).

Figure 6:
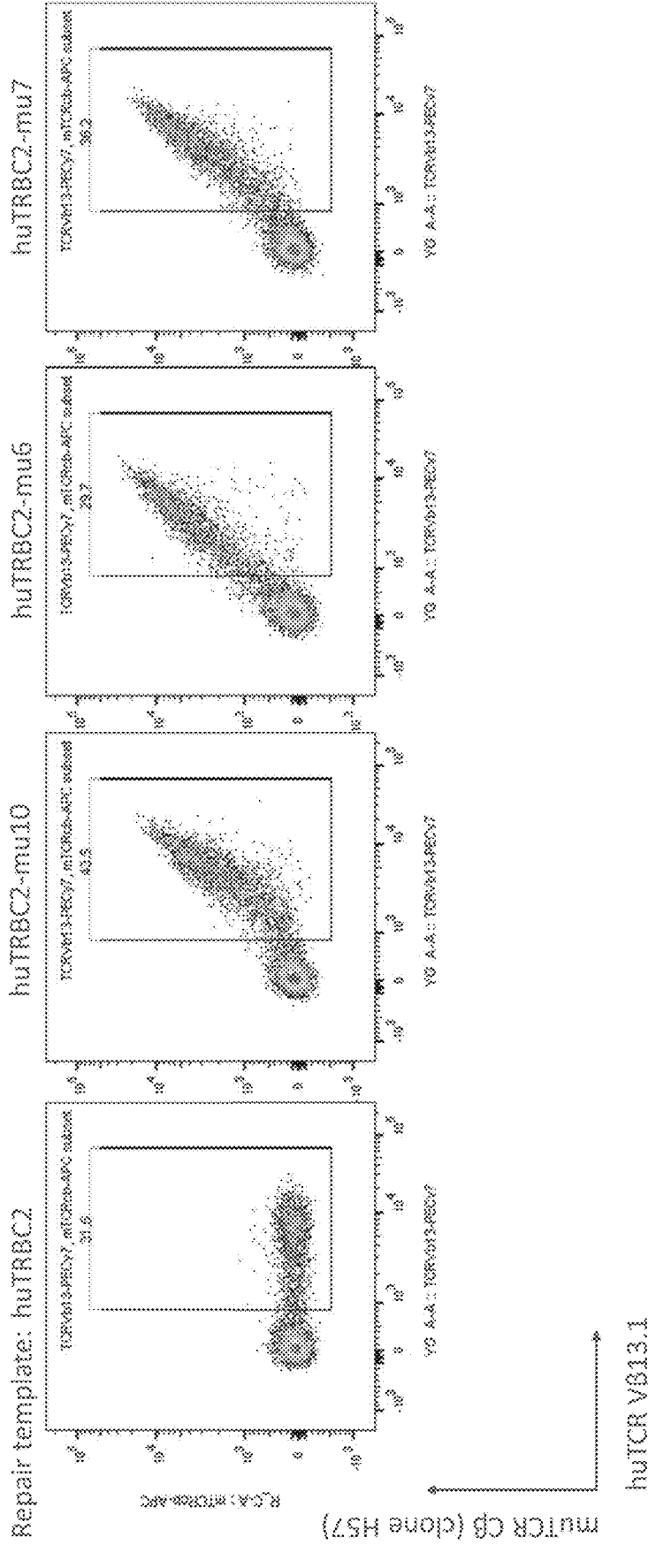
FIG. 6 shows FACS analysis of human primary T cells with knock-in of the NY-ESO-1 1G4 TCR at the endogenous TRAC locus using various repair templates. The data shows that incorporation of 6 amino acid residues from the murine Trbc2 A strand and FG loop into the human TRBC2 sequence is sufficient to enable TCR expression and H57 antibody recognition.

FIG. 6 shows FACS analysis of human primary T cells with knock-in of the NY-ESO-1 1G4 TCR at the endogenous TRAC locus using various repair templates. huTRBC2, fully human TRBC2 sequence; huTRBC2-mur10, human TRBC2 sequence with incorporation of 10 amino acid residues from the murine Trbc2 A and B strand, and FG loop (predicted H57 binding epitope); huTRBC2-mur6, human TRBC2 sequence with incorporation of 6 amino acid residues from the murine Trbc2 A strand, and FG loop (identified minimal H57 binding epitope); huTRBC2-mur7, human TRBC2 sequence with incorporation of 7 amino acid residues from the murine Trbc2 A strand, and FG loop (identified minimal H57 binding epitope+T7). The human primary CD3+ T cells were selected and activated with anti-CD3/CD28 beads for 2 days and then electroporated with a TRAC RNP and with a repair template to guide TCR knock-in. 6 days after electroporation, cells were harvested and analyzed by co-staining with an APC anti-mouse TCR Cβ chain antibody (clone H57-597, cat #109212, BioLegend) and a PE-Cy7 anti-human TCR Vβ13.1 antibody (clone H131, cat #362406, BioLegend). The data show that incorporation of 6 amino acid residues from the murine Trbc2 A strand and FG loop into the human TRBC2 sequence is sufficient to enable TCR expression and H57 antibody recognition (amino acid mutations being K4R, E108K, T110P, Q111E, D112G, R113S).

Figure 7:
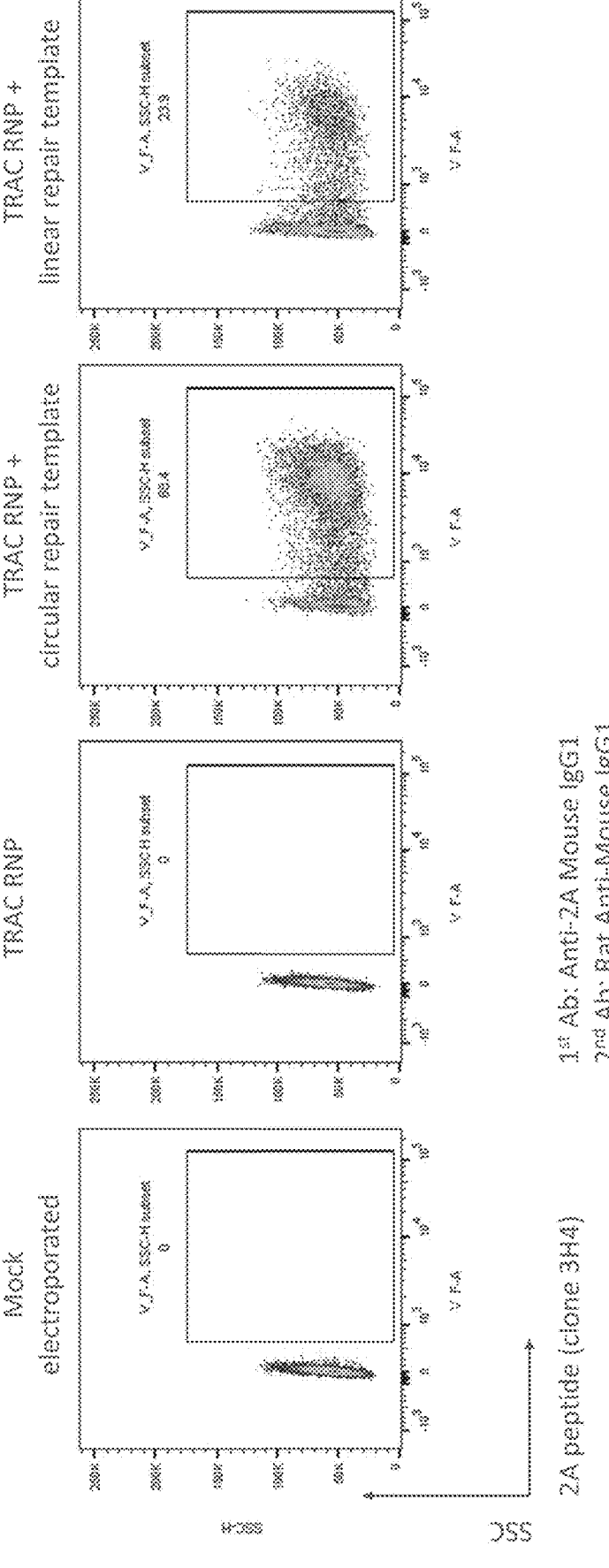
FIG. 7 shows FACS analysis of human primary T cells with knock-in of the NY-ESO-1 1G4 TCR at the endogenous TRAC locus using various repair templates. The data shows that human primary T cells that have been engineered to express an NY-ESO-1 1G4 TCR that contains a T2A peptide sequence can be detected with an anti-2A peptide antibody.

FIG. 7 shows FACS analysis of human primary T cells with knock-in of the NY-ESO-1 1G4 TCR at the endogenous TRAC locus using various repair templates. Mock electroporated, cells were not electroporated; TRAC RNP, cells were electroporated with a TRAC RNP only; TRAC RNP+ circular repair template, cells were electroporated with a TRAC RNP and a circular repair template; TRAC RNP+ linear repair template, cells were electroporated with a TRAC RNP and a linear repair template. The human primary CD3+ T cells were selected and activated with anti-CD3/CD28 beads for 2 days and then electroporated with a TRAC RNP and with a repair template to guide TCR knock-in. 10 days after electroporation, cells were harvested, permeabilized and FACS analyzed by staining with an unconjugated Mouse anti-2A peptide antibody (clone 3H4, cat #NBP2-59627, Novus Biologicals) and a BV421 Rat anti-Mouse IgG1 antibody (clone A85-1, cat #562580, BD Biosciences). All stainings were performed in BD Perm/Wash Buffer (1×). The data show that human primary T cells that have been engineered to express an NY-ESO-1 1G4 TCR that contains a T2A peptide sequence can be detected with an anti-2A peptide antibody.

Figure 8:
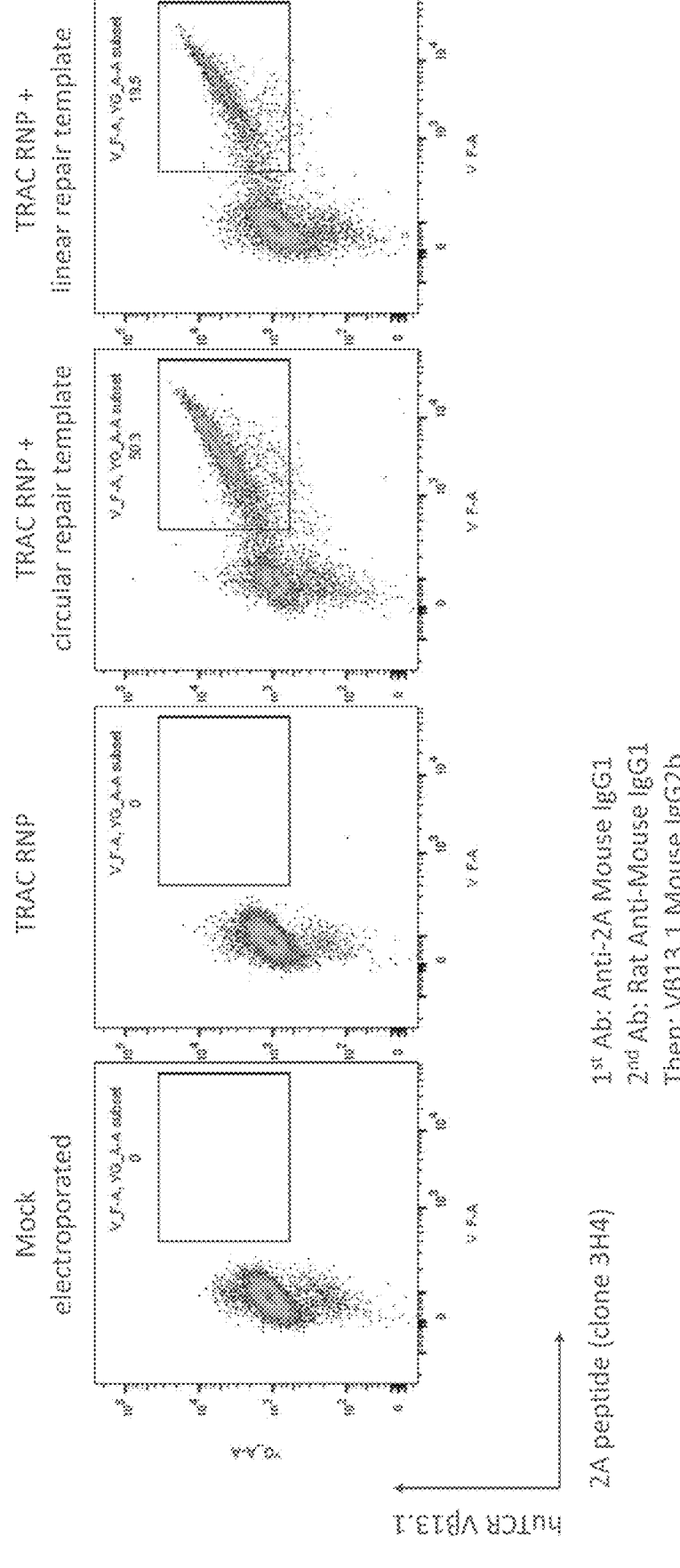
FIG. 8 shows FACS analysis of human primary T cells with knock-in of the NY-E50-1 1G4 TCR at the endogenous TRAC locus using various repair templates. The data shows that human primary T cells that have been engineered to express an NY-ESO-1 1G4 TCR that contains a T2A peptide sequence can be detected with an anti-2A peptide antibody, and that this 2A peptide staining correlates with TCR Vβ13.1 staining.

FIG. 8 shows FACS analysis of human primary T cells with knock-in of the NY-ESO-1 1G4 TCR at the endogenous TRAC locus using various repair templates. Mock electroporated, cells were not electroporated; TRAC RNP, cells were electroporated with a TRAC RNP only; TRAC RNP+ circular repair template, cells were electroporated with a TRAC RNP and a circular repair template; TRAC RNP+ linear repair template, cells were electroporated with a TRAC RNP and a linear repair template. The human primary CD3+ T cells were selected and activated with anti-CD3/CD28 beads for 2 days and then electroporated with a TRAC RNP and with a repair template to guide TCR knock-in. 11 days after electroporation, cells were harvested, permeabilized and FACS analyzed by staining with an unconjugated Mouse anti-2A peptide antibody (clone 3H4, cat #NBP2-59627, Novus Biologicals), a BV421 Rat anti-Mouse IgG1 antibody (clone A85-1, cat #562580, BD Biosciences) and a PE-Cy7 anti-human TCR Vβ13.1 antibody (clone H131, cat #362406, BioLegend). All stainings were performed in BD Perm/Wash Buffer (1×). The data show that human primary T cells that have been engineered to express an NY-ESO-1 1G4 TCR that contains a T2A peptide sequence can be detected with an anti-2A peptide antibody, and that this 2A peptide staining correlates with TCR Vβ13.1 staining.

Figure 9:
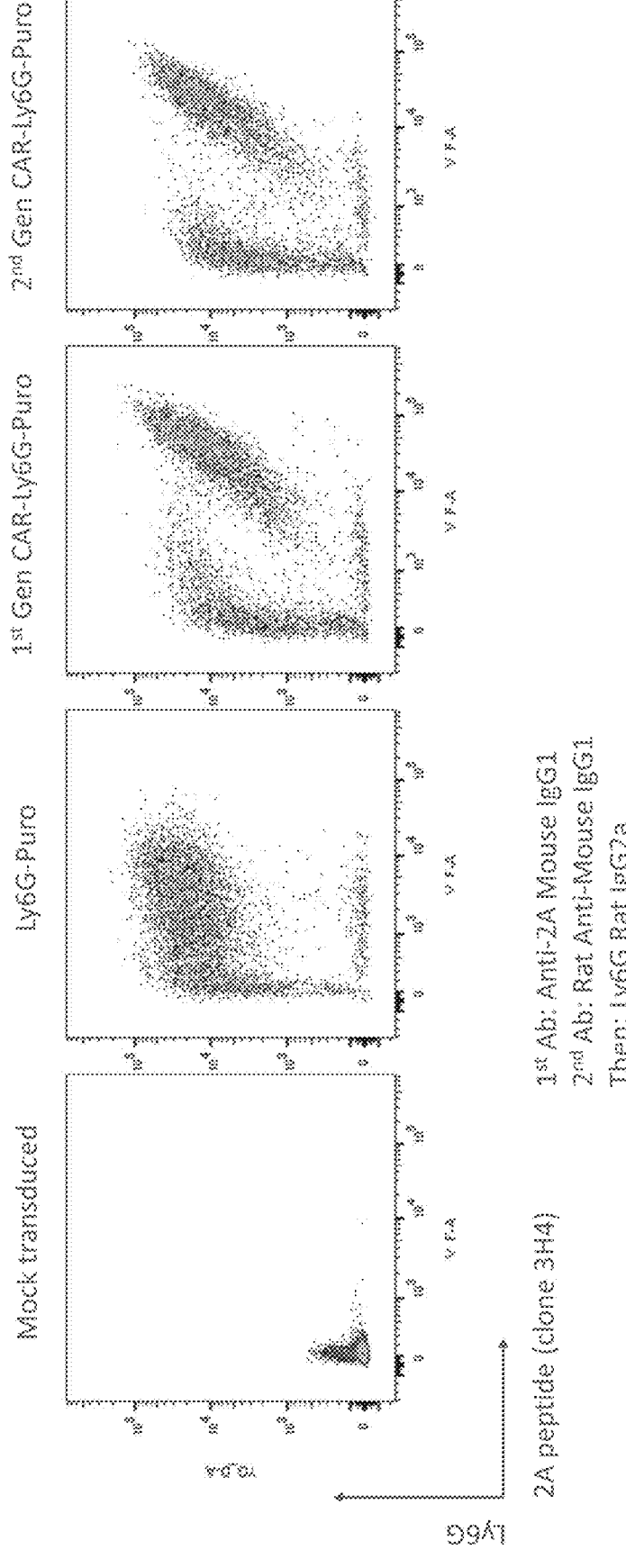
FIG. 9 shows FACS analysis of human primary T cells that have been retrovirally transduced to express a CD19 CAR construct. The data shows that human primary T cells that have been engineered to express a CD19 CAR construct that contains a 2A peptide sequence can be detected with an anti-2A peptide antibody, and that this 2A peptide staining correlates with staining of a transduction marker protein present in the same construct (Ly6G).

FIG. 9 shows FACS analysis of human primary T cells that have been retrovirally transduced to express a CD19 CAR construct. Mock transduced, cells were not transduced; Ly6G-Puro, cells were transduced with a retrovirus containing a Ly6G-P2A-Puro construct; 1st Gen CAR-Ly6G-Puro, cells were transduced with a retrovirus containing a 1st Gen CD19 CAR-T2A-Ly6G-P2A-Puro construct; 2nd Gen CAR-Ly6G-Puro, cells were transduced with a retrovirus containing a 2nd Gen CD19 CAR-T2A-Ly6G-P2A-Puro construct. The human primary CD3+ T cells were selected and activated with anti-CD3/CD28 beads for 2 days and then infected with retrovirus as indicated above. 14 days after transduction, cells were harvested, permeabilized and FACS analyzed by staining with an unconjugated Mouse anti-2A peptide antibody (clone 3H4, cat #NBP2-59627, Novus Biologicals), a BV421 Rat anti-Mouse IgG1 antibody (clone A85-1, cat #562580, BD Biosciences) and a PE/Dazzle 594 anti-Ly6G antibody (clone 1A8, cat #127647, BioLegend). All stainings were performed in BD Perm/Wash Buffer (1×). The data show that human primary T cells that have been engineered to express a CD19 CAR construct that contains a 2A peptide sequence can be detected with an anti-2A peptide antibody, and that this 2A peptide staining correlates with staining of a transduction marker protein present in the same construct (Ly6G).

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

In some embodiments, any of the following arrangements are contemplated:

1. A marked protein comprising:
a TCR constant domain; and
an exogenous amino acid variation that comprises a sequence that is detectable and identifiable within the TCR constant domain.

2. The marked protein of arrangement 1, wherein the TCR constant domain comprises a TCRα or TCRβ constant domain.

3. The marked protein of arrangement 1, wherein the exogenous amino acid variation comprises mutation of a sequence of the TCR constant domain, optionally wherein the marked protein comprises huTRBC1-mur6 or huTRBC2-mur6.

4. The marked protein of arrangement 1, wherein the TCR constant domain is from one species and the exogenous amino acid variation is from another species.

5. The marked protein of arrangement 4, wherein the TCR constant domain is from human and the exogenous amino acid variation is from non-human species.

6. The marked protein of arrangement 5, wherein the non-human species is mouse.

7. The marked protein of arrangement 3, wherein the TCR constant domain comprises a sequence encoded by the human TRBC2 gene.

8. The marked protein of arrangement 3, wherein the exogenous amino acid variation comprises a sequence of the murine TCR Cβ domain.

9. The marked protein of arrangement 3, wherein the mutation comprises 10 amino acid mutations.

10. The marked protein of arrangement 9, wherein the mutation forms a discontinuous sequence.

11. The marked protein of arrangement 9, wherein 10 amino acid mutations are K4R, F7T, Y37F, N106E, E108K, T110P, Q111E, D112G, R113S, A114P, as numbered according to the numbering system of SEQ ID NO: 8.

12. The marked protein of arrangement 3, wherein the mutation comprises 6 amino acid mutations.

13. The marked protein of arrangement 12, wherein 6 amino acid mutations are K4R, E108K, T110P, Q111E, D112G, R113S, optionally wherein the marked protein comprises SEQ ID NO: 27.

14. The marked protein of arrangement 1, wherein the exogenous amino acid variation is detectable and identifiable by an antibody, a nanobody, a Fab fragment or a DARPin.

15. The marked protein of arrangement 1, wherein the exogenous amino acid variation is detectable and identifiable by an anti-mouse TCR Cβ antibody H57-597.

16. A marked protein used for the detection, isolation, or depletion of genetically engineered cells expressing such a marked protein, comprising the marked protein of any one of the arrangements 1-15.

17. The marked protein of arrangement 16, wherein the genetically engineered cells comprise genetically engineered T cells.

18. The marked protein of arrangement 17, wherein the genetically engineered T cells comprise T cells that have been modified by the introduction of therapeutic TCR genes.

19. The marked protein of arrangement 18, wherein the T cells that have been modified by the introduction of therapeutic TCR genes are used for cancer treatment.

20. A marked protein used for the detection, isolation, or depletion of genetically engineered T cells that have been modified by the introduction of therapeutic TCR genes, wherein the marked protein is derived from the murine TCR Cβ domain and introduced into the human TCR Cβ2 domain by mutation of existing amino acids within the human TCR Cβ2 domain.

21. A marked protein for the detection, isolation or depletion of a cell modified with a novel TCR gene for the treatment of cancer, comprising the marked protein of any one of the arrangements 1-20.

22. A kit used for detection, isolation or depletion of genetically engineered cells having the marked protein of any one of the arrangements 1-21, comprising an antibody that recognizes the marked protein.

23. The kit of arrangement 22, wherein the genetically engineered cells comprise T cells.

24. The kit of arrangement 23, wherein the T cells have been modified by the introduction of therapeutic TCR genes.

25. The kit of arrangement 24, wherein the T cells that have been modified by the introduction of therapeutic TCR genes are used for cancer treatment.

26. A marked protein used for targeted delivery of one or more payloads to genetically engineered cells expressing such a marked protein, comprising the marked protein of any one of the arrangements 1-15.

27. The marked protein of arrangement 26, wherein the delivery of one or more payloads is achieved by conjugation to an antibody, an antibody mimetic protein or any other antigen-binding scaffold.

28. The marked protein of arrangement 27, wherein the antibody is an anti-mouse TCR Cβ antibody H57-597.

29. The marked protein of arrangement 26, wherein the one or more payloads is a protein, a small molecule, a nucleic acid, a liposome, or a nanoparticle.

30. The marked protein of arrangement 26, wherein the delivered payload is a cytokine.

31. The marked protein of arrangement 30 wherein the cytokine is selected from the group of IL-1β, IL-2, IL-4, IL-6, IL-7, IL-10, IL-12, IL-15, IL-17, IL-18, IL-21, IL-23, IL-27, IFN-α, IFN-β, IFN-γ, and TNF-α.

32. The marked protein of arrangement 30, wherein the cytokine is modified in its sequence in order to modulate interaction with its natural receptor molecule.

33. The marked protein of arrangement 30, wherein the cytokine is an agonist or antagonist for a receptor molecule expressed by T cells.

34. The marked protein of arrangement 26, wherein the payload is an agonist or antagonist for a receptor molecule expressed by T cells.

35. The marked protein of arrangement 34, wherein the agonist binds to CD27, CD28, CD137 or CD278.

36. The marked protein of arrangement 34, wherein the antagonist binds to TGF-beta Receptor, PD-1, CTLA-4, Vista, steroid receptor or $A_1$-, $A_{2A}$-, $A_{2B}$- or $A_3$-adenosine receptor.

37. The marked protein of arrangement 26, wherein the payload is a small molecule that modulates activation, differentiation, proliferation, survival or effector function of T cells.

38. The marked protein of arrangement 37, wherein the small molecule inhibits signaling of either TGF-beta Receptor, PD-1, CTLA-4, Vista, steroid receptor or $A_1$-, $A_2A$-, $A_{2B}$- or $A_3$-adenosine receptor.

39. The marked protein of arrangement 26, wherein the payload is a nucleic acid that modulates T cell activation, differentiation, proliferation, survival or effector function.

40. The marked protein of arrangement 39, wherein the nucleic acid is a miRNA, shRNA or siRNA.

41. The marked protein of arrangement 26, wherein the payload is a bi- or tri-specific antibody.

42. A method for targeted delivery of one or more payloads to genetically engineered cells expressing a marked protein, the method comprising:
    obtaining a conjugate comprising the one or more payloads and a binding agent, wherein the binding agent specifically binds to the marked protein, and
    contacting the genetically engineered cells with the conjugate.

43. The method of arrangement 42, wherein the binding agent is an antibody, an antibody mimetic protein, or any other antigen-binding scaffold.

44. The method of arrangement 42, wherein the one or more payloads is a protein, a small molecule, a nucleic acid, a liposome, or a nanoparticle.

45. An antibody epitope used for the detection of genetically engineered cells expressing such an antibody epitope, wherein the antibody epitope is attached to a TCR chain or a Chimeric Antigen Receptor (CAR).

46. The antibody epitope of arrangement 45, wherein the antibody epitope is attached to the C-terminus or the N-terminus of a TCR chain, or the C-terminus or the N-terminus of a CAR.

47. The antibody epitope of arrangement 45, wherein the antibody epitope is inserted into a TCR chain or a CAR.

48. The antibody epitope of arrangement 45, wherein genetically engineered cells comprise T cells.

49. The antibody epitope of arrangement 48, wherein T cells have been modified by the introduction of therapeutic TCR or CAR genes.

50. The antibody epitope of arrangement 49, wherein T cells that have been modified by the introduction of therapeutic TCR or CAR genes are used for cancer treatment.

51. The antibody epitope of arrangement 45, wherein the antibody epitope is used to connect TCRα and TCRβ chains, or to connect a CAR with a protein encoded by another gene.

52. The antibody epitope of arrangement 45 comprising a 2A peptide sequence, a HA.11 epitope tag, a FLAG epitope tag, a Myc epitope tag, a V5 epitope tag, or a peptide comprising up to a same number of amino acids as the 2A peptide.

53. The antibody epitope of arrangement 52, wherein the 2A peptide can be P2A, T2A, E2A, or F2A.

54. The antibody epitope of arrangement 45 comprising: a 2A peptide sequence fragment or a sequence at least 90% identical thereto, wherein the 2A peptide sequence is not a full 2A sequence.

55. The antibody epitope of arrangement 54, wherein the peptide sequence comprises a sequence of SEQ ID NO: 1 (CGDVEENPG) or at least 75% identical thereto.

56. The antibody epitope of arrangement 54 or 55, wherein the antibody epitope can be identified by monoclonal anti-2A peptide antibody 3H4.

57. An antibody epitope used for the detection of genetically engineered T cells that have been modified by the introduction of therapeutic TCR genes, comprising the antibody epitope of any one of arrangements 45-56.

58. An antibody epitope for the detection of a cell modified with a novel TCR or CAR gene for the treatment of cancer, comprising the antibody epitope of any one of arrangements 45-56.

59. A kit used for detection of genetically engineered cells, comprising the antibody epitope of any one of arrangements 45-56.

60. The kit of arrangement 59, wherein the genetically engineered cells comprise T cells.

61. The kit of arrangement 60, wherein the T cells have been modified by the introduction of therapeutic TCR genes.

62. The kit of arrangement 61, wherein the T cells that have been modified by the introduction of therapeutic TCR genes are used for cancer treatment.

63. A genetic construct comprising: a nucleotide sequence capable of expressing a 2A peptide sequence or a sequence that is at least 90% identical thereto, wherein the construct is configured for the expression of multiple proteins from a single open reading frame, and wherein the nucleotide sequence does not increase a size of the genetic construct by more than 25 amino acids.

64. The genetic construct of arrangement 63, wherein the 2A peptide sequence comprises a 2A peptide sequence fragment or a sequence at least 90% identical thereto, wherein the 2A peptide sequence is not a full 2A sequence.

65. The genetic construct of arrangement 64, wherein the 2A peptide sequence comprises a sequence of SEQ ID NO: 2, SEQ ID NO: 3, SEQ ID NO: 6, or a sequence at least 75% identical to SEQ ID NO: 2, SEQ ID NO: 3, or SEQ ID NO: 6. (SEQ ID NO: 2=EGRGSLLTCGDVEENPGP; SEQ ID NO: 3=ATNFSLLKQAGDVEENPGP; SEQ ID NO: 6=GDVEENPG).

66. A genetically engineered cell comprising the marked protein of any one of the arrangements 1-15, or the antibody epitope of any one of arrangements 53-55, or the genetic construct of any one of arrangements 63-65.

EXAMPLE 1

This example shows that incorporation of 10 amino acid residues from the murine Trbc2 A and B strand, and FG loop into the human TRBC2 sequence is sufficient to allow for TCR expression and H57 antibody recognition.

FACS analysis was performed with human primary T cells with knock-in of the NY-ESO-1 1G4 TCR at the endogenous TRAC locus using various repair templates. The human primary CD3⁺ T cells were selected and activated with anti-CD3/CD28 beads for 2 days and then electroporated with a TRAC RNP and with a repair template to guide TCR knock-in. 5 days after electroporation, cells were harvested and analyzed by co-staining with an APC anti-mouse TCR Cβ chain antibody (clone H57-597, cat #109212, BioLegend) and a PE-Cy7 anti-human TCR Vβ13.1 antibody (clone H131, cat #362406, BioLegend). Then FACS analysis was performed.

The results are represented in FIG. 3: huTRBC1, fully human TRBC1 sequence; muTrbc2, fully murine Trbc2 sequence without polyA signal; muTrbc2-BGHpA, fully murine Trbc2 sequence with BGH polyA signal; huTRBC1-muFG, human TRBC1 sequence with incorporation of the murine Trbc2 FG loop.

The data show that a polyA signal is useful for TCR expression when using a fully murine Trbc2 sequence, and that cells that express a fully murine Trbc2 sequence can be recognized by the H57 antibody. However, incorporation of the murine Trbc2 FG loop into the human TRBC1 sequence, while enabling TCR expression, is not sufficient for H57 antibody recognition.

Next, incorporation of 10 amino acid residues from the murine Trbc2 A and B strand and FG loop into the human TRBC2 sequence was tested. Similarly, the human primary CD3⁺ T cells were selected and activated with anti-CD3/CD28 beads for 2 days and then electroporated with a TRAC RNP and with a repair template to guide TCR knock-in. 5 days after electroporation, cells were harvested and analyzed by co-staining with an APC anti-mouse TCR Cβ chain antibody (clone H57-597, cat #109212, BioLegend) and a PE-Cy7 anti-human TCR Vβ13.1 antibody (clone H131, cat #362406, BioLegend). Then FACS analysis was performed.

The results are represented in FIG. 4: huTRBC1, fully human TRBC1 sequence; muTrbc2-BGHpA, fully murine Trbc2 sequence with BGH polyA signal; huTRBC2-muABFG, human TRBC2 sequence with incorporation of 10 amino acid residues from the murine Trbc2 A and B strand and FG loop.

The data show that incorporation of 10 amino acid residues from the murine Trbc2 A and B strand and FG loop into the human TRBC2 sequence is sufficient to allow TCR expression and H57 antibody recognition (amino acid mutations being K4R, F7T, Y37F, N106E, E108K, T110P, Q111E, D112G, R113S, A114P).

EXAMPLE 2

This example shows that incorporation of 6 amino acid residues from the murine Trbc2 A strand and FG loop into the human TRBC2 sequence is sufficient to allow for TCR expression and H57 antibody recognition.

FACS analysis was performed with human primary T cells with knock-in of the NY-ESO-1 1G4 TCR at the endogenous TRAC locus using various repair templates. The human primary CD3$^+$ T cells were selected and activated with anti-CD3/CD28 beads for 2 days and then electroporated with a TRAC RNP and with a repair template to guide TCR knock-in. 5 days after electroporation, cells were harvested and analyzed by co-staining with an APC anti-mouse TCR Cβ chain antibody (clone H57-597, cat #109212, BioLegend) and a PE-Cy7 anti-human TCR Vβ13.1 antibody (clone H131, cat #362406, BioLegend). Then FACS analysis was performed.

The results are represented in FIG. 5: huTRBC2, fully human TRBC2 sequence; huTRBC2-muABFG, human TRBC2 sequence with incorporation of 10 amino acid residues from the murine Trbc2 A and B strand, and FG loop (predicted H57 binding epitope); muABFG R4K, human TRBC2 sequence with incorporation of 9 amino acid residues from the murine Trbc2 A and B strand, and FG loop, and 1 amino acid residue reverted back to the human counterpart (R4K) to map the minimal H57 binding epitope; muABFG T7F, human TRBC2 sequence with incorporation of 9 amino acid residues from the murine Trbc2 A and B strand, and FG loop, and 1 amino acid residue reverted back to the human counterpart (T7F) to map the minimal H57 binding epitope; muABFG F37Y, human TRBC2 sequence with incorporation of 9 amino acid residues from the murine Trbc2 A and B strand, and FG loop, and 1 amino acid residue reverted back to the human counterpart (F37Y) to map the minimal H57 binding epitope; muABFG E106N, human TRBC2 sequence with incorporation of 9 amino acid residues from the murine Trbc2 A and B strand, and FG loop, and 1 amino acid residue reverted back to the human counterpart (E106N) to map the minimal H57 binding epitope; muABFG K108E, human TRBC2 sequence with incorporation of 9 amino acid residues from the murine Trbc2 A and B strand, and FG loop, and 1 amino acid residue reverted back to the human counterpart (K108E) to map the minimal H57 binding epitope; muABFG P110T, human TRBC2 sequence with incorporation of 9 amino acid residues from the murine Trbc2 A and B strand, and FG loop, and 1 amino acid residue reverted back to the human counterpart (P110T) to map the minimal H57 binding epitope; muABFG E111Q, human TRBC2 sequence with incorporation of 9 amino acid residues from the murine Trbc2 A and B strand, and FG loop, and 1 amino acid residue reverted back to the human counterpart (E111Q) to map the minimal H57 binding epitope; muABFG G112D, human TRBC2 sequence with incorporation of 9 amino acid residues from the murine Trbc2 A and B strand, and FG loop, and 1 amino acid residue reverted back to the human counterpart (G112D) to map the minimal H57 binding epitope; muABFG S113R, human TRBC2 sequence with incorporation of 9 amino acid residues from the murine Trbc2 A and B strand, and FG loop, and 1 amino acid residue reverted back to the human counterpart (S113R) to map the minimal H57 binding epitope; muABFG P114A, human TRBC2 sequence with incorporation of 9 amino acid residues from the murine Trbc2 A and B strand, and FG loop, and 1 amino acid residue reverted back to the human counterpart (P114A) to map the minimal H57 binding epitope. The data show that 6 amino acid residues from the murine Trbc2 A strand and FG loop are necessary to enable H57 antibody recognition (amino acids being R4, K108, P110, E111, G112, and S113).

Next, human primary CD3$^+$ T cells were selected and activated with anti-CD3/CD28 beads for 2 days and then electroporated with a TRAC RNP and with a repair template to guide TCR knock-in. 6 days after electroporation, cells were harvested and analyzed by co-staining with an APC anti-mouse TCR Cβ chain antibody (clone H57-597, cat #109212, BioLegend) and a PE-Cy7 anti-human TCR Vβ13.1 antibody (clone H131, cat #362406, BioLegend). Then FACS analysis was performed.

The results are represented in FIG. 6: huTRBC2, fully human TRBC2 sequence; huTRBC2-mu10, human TRBC2 sequence with incorporation of 10 amino acid residues from the murine Trbc2 A and B strand, and FG loop (predicted H57 binding epitope); huTRBC2-mur6, human TRBC2 sequence with incorporation of 6 amino acid residues from the murine Trbc2 A strand, and FG loop (identified minimal H57 binding epitope); huTRBC2-mur7, human TRBC2 sequence with incorporation of 7 amino acid residues from the murine Trbc2 A strand, and FG loop (identified minimal H57 binding epitope+T7). The data show that incorporation of 6 amino acid residues from the murine Trbc2 A strand and FG loop into the human TRBC2 sequence is sufficient to enable TCR expression and H57 antibody recognition (amino acid mutations being K4R, E108K, T110P, Q111E, D112G, R113S).

EXAMPLE 3

This example shows that human primary T cells that have been engineered to express an NY-ESO-1 1G4 TCR that contains a T2A peptide sequence can be detected with an anti-2A peptide antibody.

FACS analysis was performed with human primary T cells with knock-in of the NY-ESO-1 1G4 TCR at the endogenous TRAC locus using various repair templates. The human primary CD3$^+$ T cells were selected and activated with anti-CD3/CD28 beads for 2 days and then electroporated with a TRAC RNP and with a repair template to guide TCR knock-in. 10 days after electroporation, cells were harvested, permeabilized and FACS analyzed by staining with an unconjugated Mouse anti-2A peptide antibody (clone 3H4, cat #NBP2-59627, Novus Biologicals) and a BV421 Rat anti-Mouse IgG1 antibody (clone A85-1, cat #562580, BD Biosciences). All stainings were performed in BD Perm/Wash Buffer (1×). Then FACS analysis was performed.

The results are represented in FIG. 7: mock electroporated, cells were not electroporated; TRAC RNP, cells were electroporated with a TRAC RNP only; TRAC RNP+circular repair template, cells were electroporated with a TRAC RNP and a circular repair template; TRAC RNP+linear repair template, cells were electroporated with a TRAC RNP and a linear repair template. The data show that human primary T cells that have been engineered to express an NY-ESO-1 1G4 TCR that contains a T2A peptide sequence can be detected with an anti-2A peptide antibody.

EXAMPLE 4

This example shows that human primary T cells that have been engineered to express an NY-ESO-1 1G4 TCR that contains a T2A peptide sequence can be detected with an anti-2A peptide antibody, and that this 2A peptide staining correlates with TCR Vβ13.1 staining.

FACS analysis was performed with human primary T cells with knock-in of the NY-ESO-1 1G4 TCR at the endogenous TRAC locus using various repair templates. The human primary CD3$^+$ T cells were selected and activated with anti-CD3/CD28 beads for 2 days and then electroporated with a TRAC RNP and with a repair template to guide TCR knock-in. 11 days after electroporation, cells were harvested, permeabilized and FACS analyzed by staining with an unconjugated Mouse anti-2A peptide antibody (clone 3H4, cat #NBP2-59627, Novus Biologicals), a BV421 Rat anti-Mouse IgG1 antibody (clone A85-1, cat #562580, BD Biosciences) and a PE-Cy7 anti-human TCR Vβ13.1 antibody (clone H131, cat #362406, BioLegend). All stainings were performed in BD Perm/Wash Buffer (1×). Then FACS analysis was performed.

The results are represented in FIG. 8: mock electroporated, cells were not electroporated; TRAC RNP, cells were electroporated with a TRAC RNP only; TRAC RNP+circular repair template, cells were electroporated with a TRAC RNP and a circular repair template; TRAC RNP+linear repair template, cells were electroporated with a TRAC RNP and a linear repair template. The data show that human primary T cells that have been engineered to express an NY-ESO-1 1G4 TCR that contains a T2A peptide sequence can be detected with an anti-2A peptide antibody, and that this 2A peptide staining correlates with TCR Vβ13.1 staining.

EXAMPLE 5

This example shows that human primary T cells that have been engineered to express a CD19 CAR construct that contains a 2A peptide sequence can be detected with an anti-2A peptide antibody, and that this 2A peptide staining correlates with staining of a transduction marker protein present in the same construct (Ly6G).

FACS analysis was performed with human primary T cells that have been retrovirally transduced to express a CD19 CAR construct. The human primary CD3$^+$ T cells were selected and activated with anti-CD3/CD28 beads for 2 days and then infected with retrovirus as indicated above. 14 days after transduction, cells were harvested, permeabilized and FACS analyzed by staining with an unconjugated Mouse anti-2A peptide antibody (clone 3H4, cat #NBP2-59627, Novus Biologicals), a BV421 Rat anti-Mouse IgG1 antibody (clone A85-1, cat #562580, BD Biosciences) and a PE/Dazzle 594 anti-Ly6G antibody (clone 1A8, cat #127647, BioLegend). All stainings were performed in BD Perm/Wash Buffer (1×). Then FACS analysis was performed.

The results are represented in FIG. 9: mock transduced, cells were not transduced; Ly6G-Puro, cells were transduced with a retrovirus containing a Ly6G-P2A-Puro construct; 1$^{st}$ Gen CAR-Ly6G-Puro, cells were transduced with a retrovirus containing a 1$^{st}$ Gen CD19 CAR-T2A-Ly6G-P2A-Puro construct; 2$^{nd}$ Gen CAR-Ly6G-Puro, cells were transduced with a retrovirus containing a 2$^{nd}$ Gen CD19 CAR-T2A-Ly6G-P2A-Puro construct. The data show that human primary T cells that have been engineered to express a CD19 CAR construct that contains a 2A peptide sequence can be detected with an anti-2A peptide antibody, and that this 2A peptide staining correlates with staining of a transduction marker protein present in the same construct (Ly6G).

EXAMPLE 6

This example shows a marked protein that can be used for targeted delivery of one or more payloads to genetically engineered cells expressing such a marked protein. The delivery of one or more payloads is achieved by conjugation to the H57 antibody.

An IL2v was fused at its N-terminus to the C-terminus of the H57 IgG Fc domain, optionally through a (G4S)3 linker peptide. The Fc domain comprises one or more amino acid substitutions to reduce binding to an Fc receptor. Substitutions being L234A, L235A and P329G (LALAPG, based on a human IgG1 Fc domain).

FACS analysis was performed on TCR knockout CD8hi Jurkat cells engineered to express the human TRBC2-Mur6 1G4 TCR. FACS analysis was also done on human primary T cells with knock-in of the huTRBC2-Mur6 1G4 TCR at the endogenous TRAC locus. The huTRBC2-mur6-expressing cells were pre-incubated with various concentrations of an H57 antibody, or with H57-IL2 or H57-IL2v immunocytokines for 30 minutes. Then, cells were FACS analyzed by staining with an APC anti-mouse TCR-Cβ antibody (clone H57-597, Cat #553174, BD Biosciences) and FITC anti-human IL2 antibody (clone 5344.111, cat #340448, BD Biosciences). Staining was performed in PBS containing 2% FBS.

Figure 18:
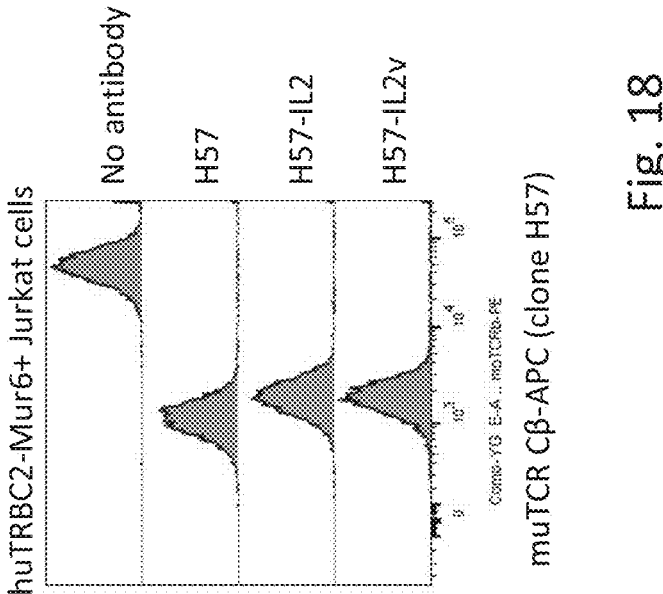
FIG. 18 shows a FACS histogram of huTRBC2-Mur6 1G4 TCR Jurkat cells stained with a labeled H57 antibody after pre-incubation with no antibody, H57, H57-IL2, or H57-IL2v, where decreased staining reflects binding of the pre-incubated antibody or fusion protein.
Figure 19:
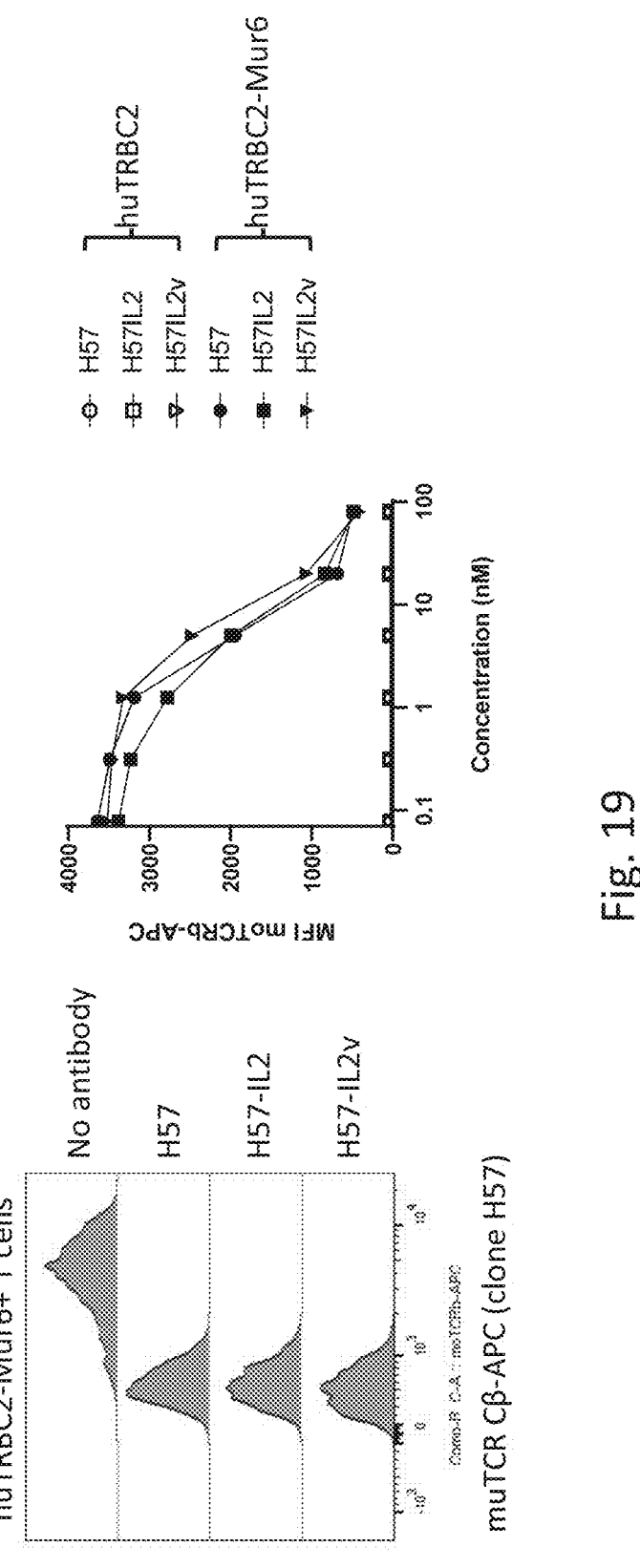
FIG. 19 shows a FACS histogram and competition concentration curve of huTRBC2-Mur6 1G4 TCR primary T cells stained with a labeled H57 antibody after pre-incubation with no antibody, H57, H57-IL2, or H57-IL2v, where decreased staining reflects binding of the pre-incubated antibody or fusion protein.
Figure 20:
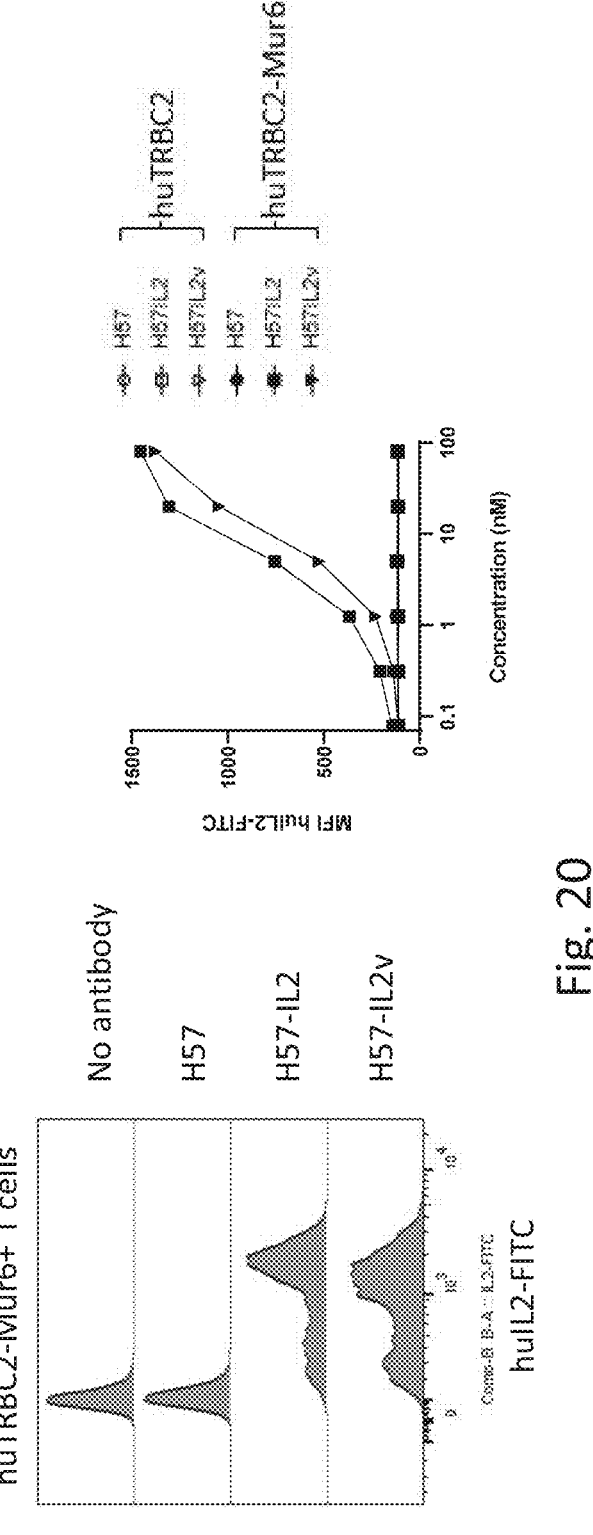
FIG. 20 shows a FACS histogram of huTRBC2-Mur6 1G4 TCR primary T cells stained with a labeled antibody directed to IL2 and a binding concentration curve.

FIG. 18 shows that 20 ng/mL of H57, as well as H57-IL2 and H57-IL2v block huTRBC2-Mur6 binding of the APC anti-mouse TCR-Cβ antibody on huTRBC2-Mur6 1G4 Jurkat cells. FIG. 19 demonstrates that H57, as well as H57-IL2 and H57-IL2v block huTRBC2-Mur6 binding of the APC anti-mouse TCR-Cβ antibody on human primary huTRBC2-Mur6 1G4 TCR T cells. huTRBC2-Mur6 1G4 T cell incubated with H57-IL2 or H57-IL2v showed strong staining with FITC anti-human IL2 antibody, as shown in FIG. 20, demonstrating presence of IL2 on the surface of these cells. Incubation of H57-IL2 and H57-IL2v on human primary huTRBC2 1G4 T cells not expressing a Mur6 epitope did result in IL2 staining, indicating Mur6-specific targeting of IL2 by the immunocytokines. Together, these data show that the Mur6 epitope can be used to mediate targeted cytokine delivery to 1G4 TCR-engineered cells expressing a huTRBC2-Mur6 constant domain by H57-IL2 and H57-IL2 antibody-cytokine fusion proteins.

EXAMPLE 7

This example assesses in vitro the stimulatory capacity of the H57-IL2v conjugate on T cell proliferation.

The H57-IL2v conjugate from example 6 will be added to CFSE-labeled primary human T cells that have been preactivated with PHA over night, after which the cells will be cultured for an additional 4 days. An irrelevant antibody-IL2v conjugate will be used as a control. After 4 days, the stimulatory capacity of the H57-IL2v conjugate on T cell proliferation will be assessed by measuring CFSE dilution as well as CD25 upregulation on the T cells using flow cytometry.

In an experiment using an alternative to CFSE, the H57-IL2 and H57-IL2v conjugates from example 6 were added to Celltrace Violet (CTV)-labeled primary human T cells with knock-in of the huTRBC2 1G4 TCR or the huTRBC2-Mur6 1G4 TCR at the endogenous TRAC locus, after which the cells were cultured for 4 days. Non-targeted recombinant IL-2 is used as a control. After 1 day, the stimulatory capacity of the H57-IL2 and H57-IL2v conjugates was assessed by measuring expression of T cell activation markers CD69 and CD25. FACS analysis was performed by co-staining with a PE anti-human CD69 antibody (Clone FN50, Cat #557050, BD Biosciences) and BV711 anti-human CD25 antibody (Clone 2A3. Cat #563159, BD Biosciences) After 4 days of culture, the stimulatory capacity of the H57-IL2 and H57-IL2v conjugates on T cell proliferation was assessed by measuring CTV dilution and cell counts of the T cells using flow cytometry. All staining was performed in PBS containing 2% FBS.

Figure 21:
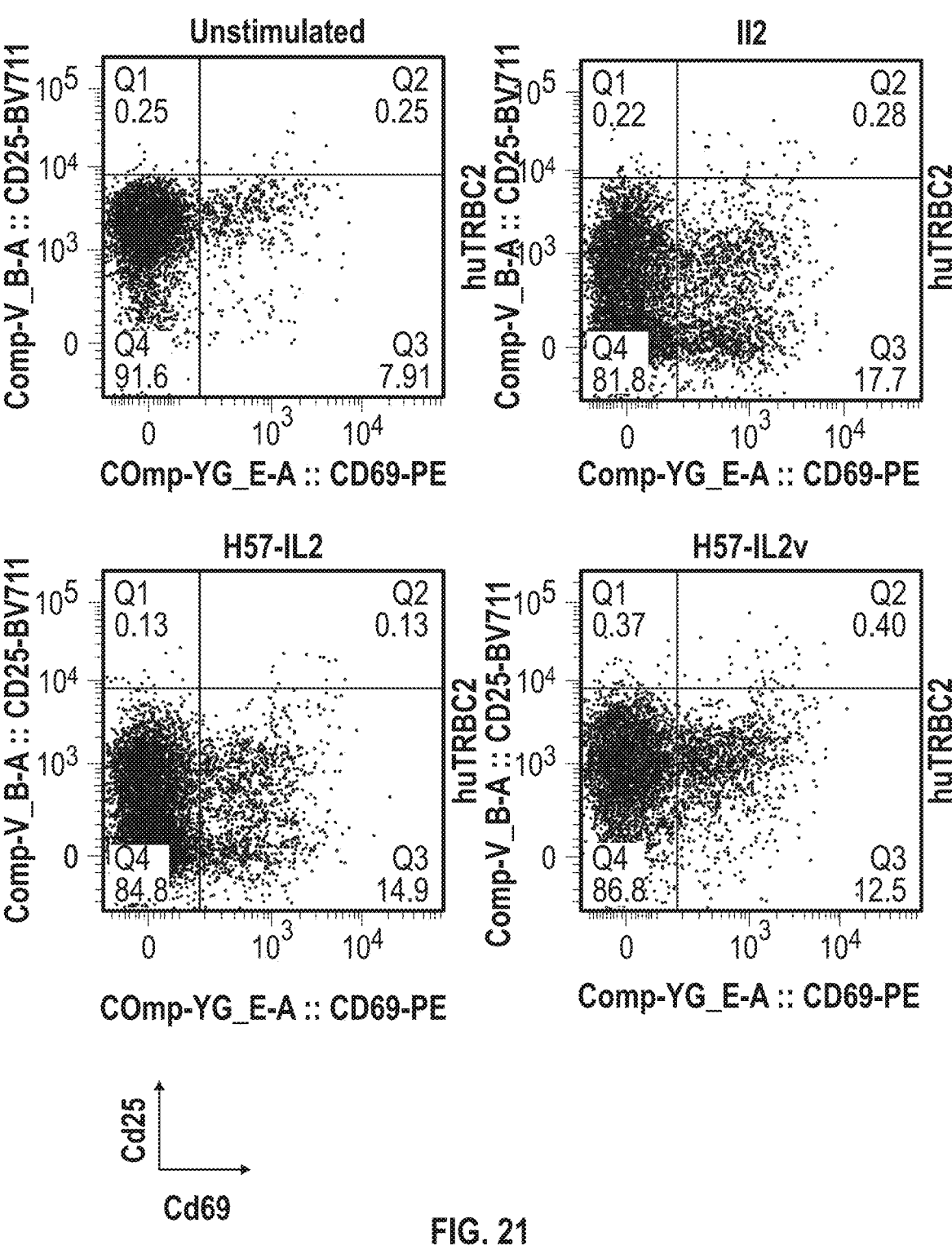
FIG. 21 shows FACS plots of the stimulation response as measured by CD25 and CD69 expression in response to IL2, H57-IL2, or H57-IL2v fusion proteins.
Figure 21:
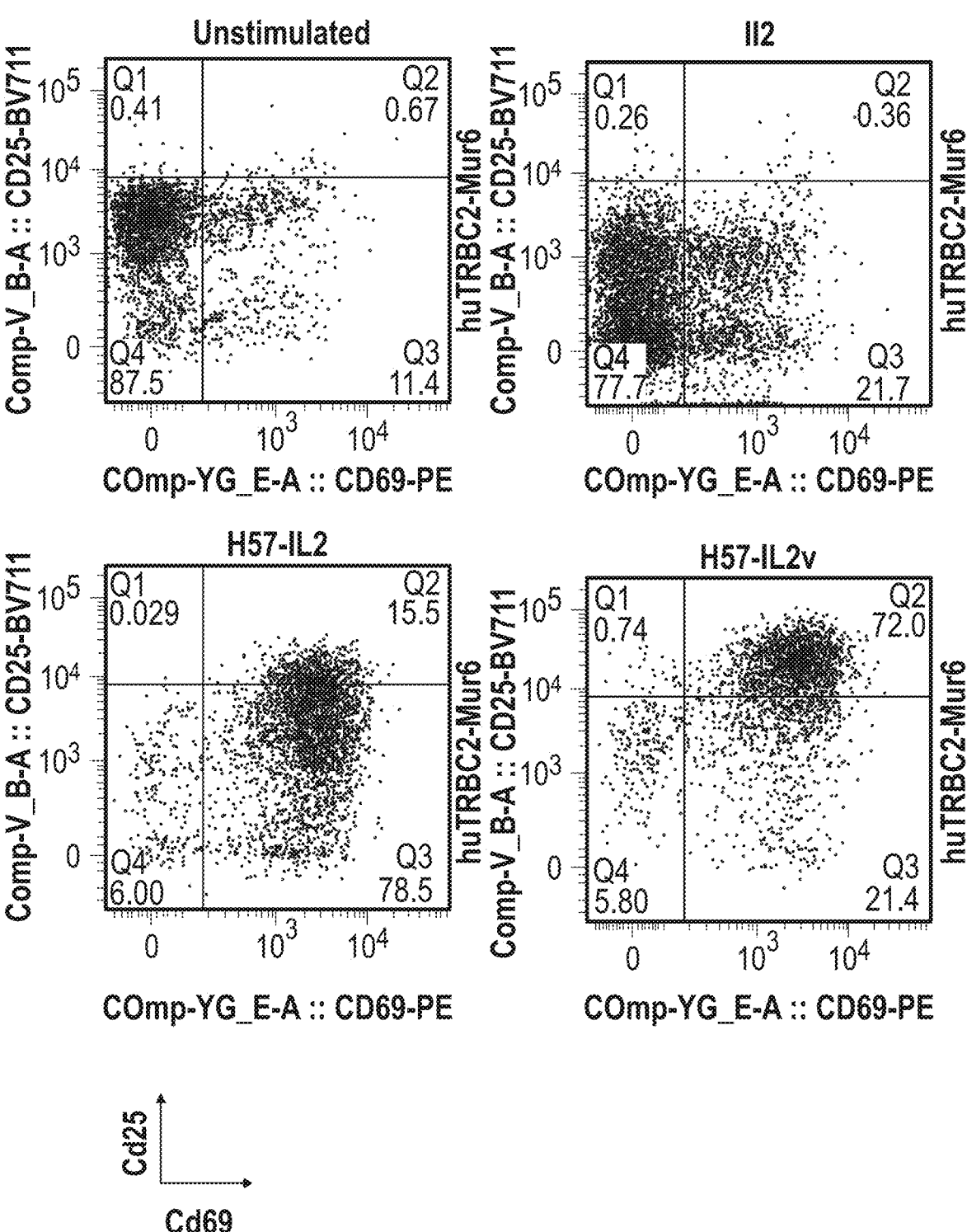

FIG. 21 depicts dot plots showing expression of T cell activation markers CD69 and CD25 after incubation of 1 nM of IL2, H57-IL2 and H57-IL2v on primary human T cells with knock-in of the huTRBC2 1G4 TCR or the huTRBC2-Mur6 1G4 TCR for 1 day. The graphs in FIGS. 22A and 22B show the percentage of CD69-expressing T cells (FIG. 22A) and CD25high T cells (FIG. 22B) over a range of (immuno) cytokine concentrations. These results demonstrate that H57-IL2 and H57-IL2v conjugates strongly and specifically stimulate T cells expressing the huTRBC2-Mur6 1G4 TCR.

Figure 23:
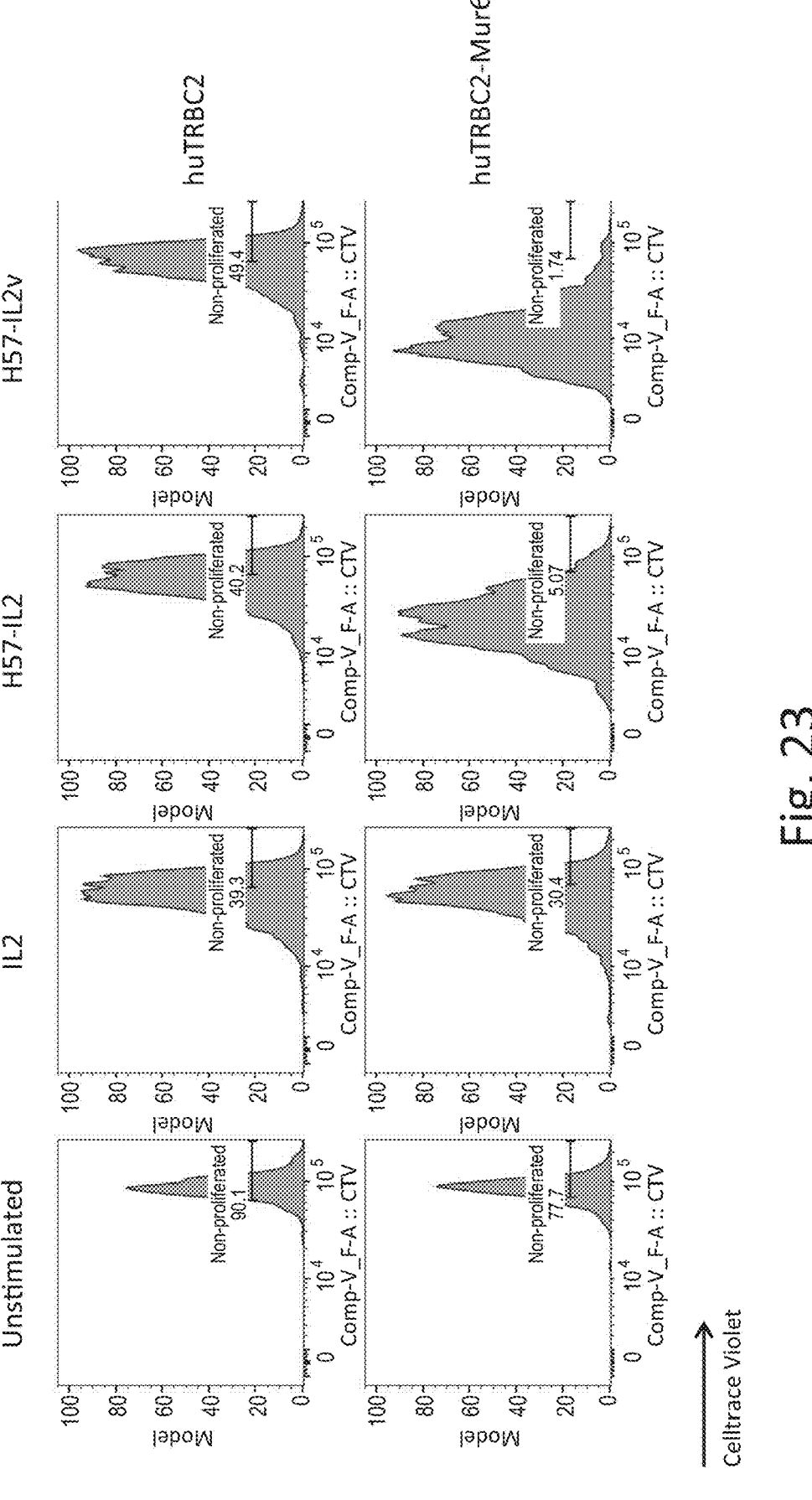
FIG. 23 shows a FACS histogram demonstrating the increase in proliferation as measured by cell trace violet in response to IL2, H57-IL2, or H57-IL2v fusion proteins.
Figure 24:
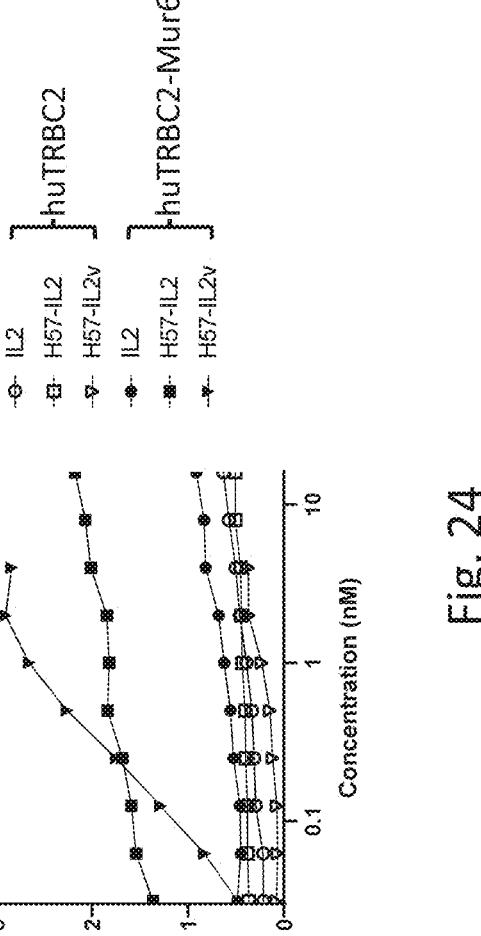
FIG. 24 shows increase in proliferation as measured by cell trace violet over a range of concentrations of IL2, H57-IL2, or H57-IL2v fusion proteins.

In FIG. 23, histograms show CTV dilution of T cells after incubation of 1 nM of IL2, H57-IL2 and H57-IL2v on primary human T cells with knock-in of the huTRBC2 1G4 TCR or the huTRBC2-Mur6 1G4 TCR for 4 days. Furthermore, FIG. 24 shows the mean proliferation cycle derived from CTV FACS measurements, calculated as the 2 log of $MFI_{undivided}/MFI_{all\ cells}$ over a range of (immuno)cytokine concentrations. These results demonstrate that mur6 targeting with H57-IL2 and H57-IL2v specifically promote T cell proliferation on T cells expressing the huTRBC2-Mur6 1G4 TCR. Together, these data that the Mur6 epitope on 1G4 TCR-engineered T cells allows specific cytokine targeting using H57-IL2 and H57-IL2v immunocytkines, thereby inducing epitope-specific T cell stimulation.

EXAMPLE 8

This example shows how H57-IL2v conjugate affects tumor growth and T cell accumulation in the tumor in vivo.

NSG mice are used here. The NSG mouse (NOD scid gamma mouse) is a brand of immunodeficient laboratory mice, developed and marketed by Jackson Laboratory, which carries the strain NOD. NSG mice will be subcutaneously implanted with NY-ESO-1+A375 melanoma cells, after which they will receive NY-ESO-1 TCR-expressing primary human T cells. Thereafter, mice will receive weekly injections with the H57-IL2v conjugate or a vehicle control. Then, the effects on tumor growth and T cell accumulation in the tumor will be measured over time.

EXAMPLE 9

This example shows that incorporation of 6 amino acid residues from the murine Trbc2. A strand and FG loop into the human TRBC1 or TRBC2 sequence is sufficient to allow for TCR expression and H57 antibody recognition.

FACS analysis was performed on human primary T cells with knock-in of the NY-ESO-1—specific 1G4 TCR at the endogenous TRAC locus using various DNA repair templates. Human primary CD3$^+$ T cells from 3 healthy donors (BC45, BC46, and BC48) were selected and activated with anti-CD3/CD28 beads (cat #40203D, ThermoFisher Scientific) for 2 days and then electroporated with a TRAC RNP and with a DNA repair template to guide TCR knock-in, as well as with a TRBC RNP to guide endogenous TCRβ chain knock-out. 5 days after electroporation, 1G4 TCR-engineered T cells were harvested and FACS analyzed by co-staining with an PE anti-mouse TCR Cβ chain antibody (clone H57-597, cat #553172, BD Biosciences) and a Brilliant Violet 421 anti-human TCR Cβ chain antibody (clone IP26, cat #306722, BioLegend).

Figure 25:
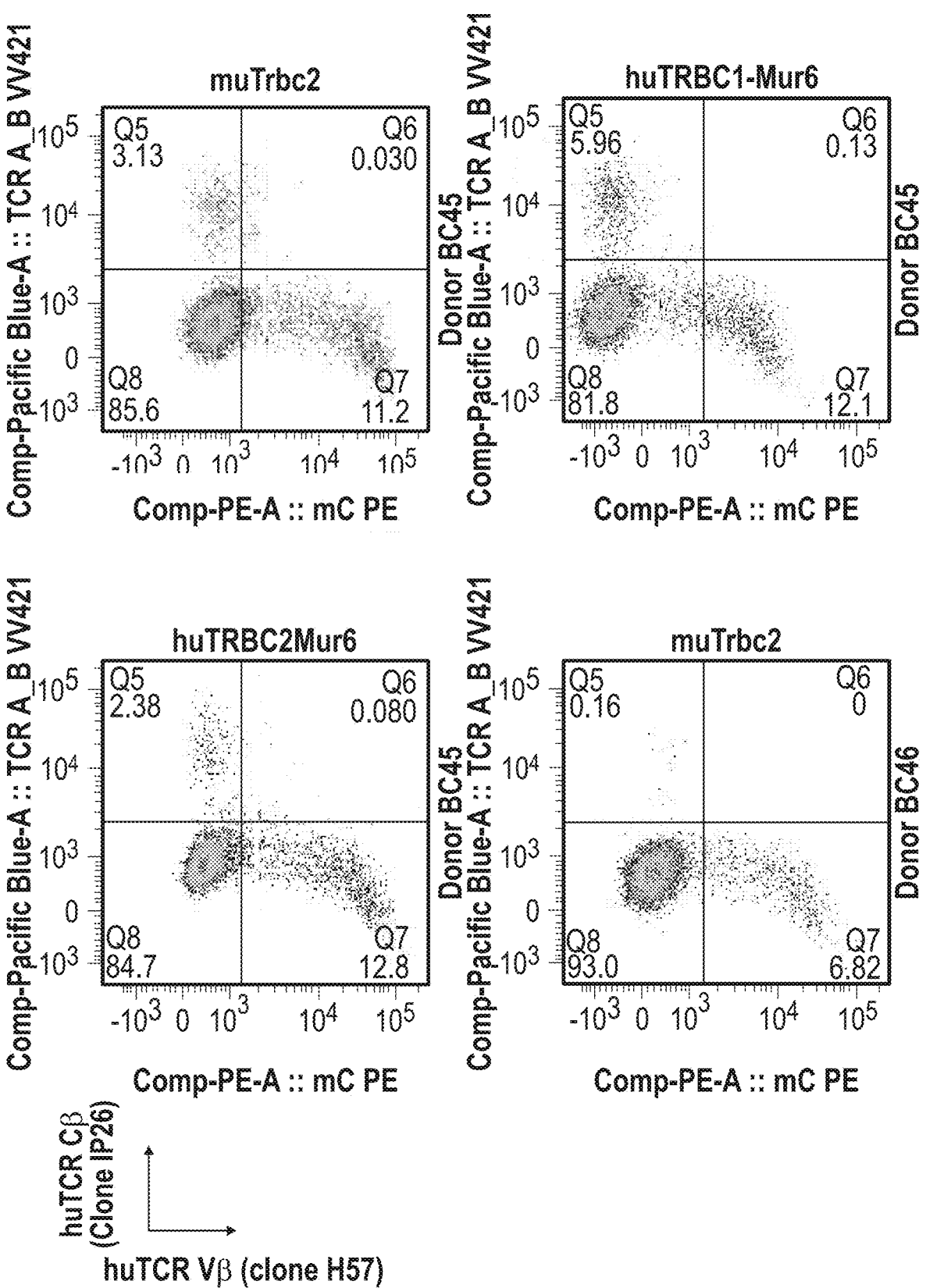
FIG. 25 shows FACS plots of the binding of H57 and an antibody that binds to human TCR beta constant domain for muTRBC2, huTRBC1-Mur6, and huTRBC2-Mur6 1G4 expressing cells.
Figure 25:
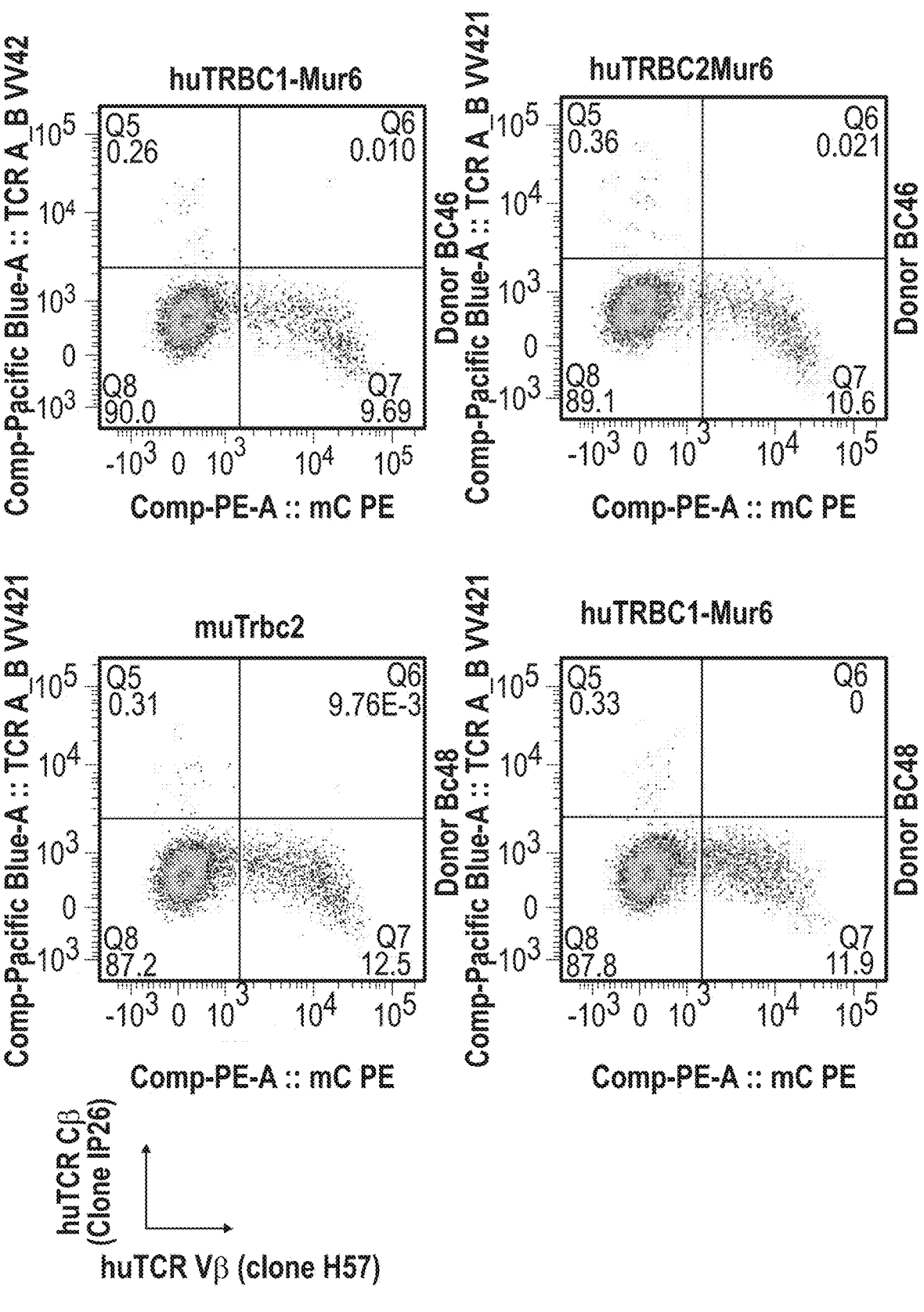

The results are represented in FIG. 25: muTrbc2 depicts a 1G4 TCR with fully murine Trbc2 constant domain sequence; huTRBC1-Mur6 depicts a 1G4 TCR with human TRBC1 constant domain sequence with incorporation of 6 amino acid residues from the murine Trbc2 A strand, and FG loop (identified minimal H57 binding epitope); huTRBC2-Mur6 depicts a 1G4 TCR with human TRBC2 constant domain sequence with incorporation of 6 amino acid residues from the murine Trbc2 A strand, and FG loop (identified minimal H57 binding epitope). The data show that incorporation of 6 amino acid residues from the murine Trbc2 A strand and FG loop into the human TRBC1 or TRBC2 sequence is sufficient to enable TCR expression and H57 antibody recognition (amino acid mutations being N4R, E108K, T110P, Q111E, D112G, R113S for huTRBC1-Mur6 and K4R, E108K, T110P, Q111E, D112G, R113S for huTRBC2-Mur6, respectively).

EXAMPLE 10

This example shows that incorporation of 6 amino acid residues from the murine Trbc2 A strand and FG loop into the human TRBC2 sequence does not interfere with TCR function as measured by T cell cytokine production.

FACS analysis was performed on human primary T cells with knock-in of the NY-ESO-1—specific 1G4 TCR at the endogenous TRAC locus using various DNA repair templates. Human primary CD3+ T cells from 3 healthy donors (BC20, BC93, and BC97) were selected and activated with anti-CD3/CD28 beads (cat #40203D, ThermoFisher Scientific) for 2 days and then electroporated with a TRAC RNP and with a DNA repair template to guide TCR knock-in, as well as with a TRBC RNP to guide endogenous TCRβ chain knock-out. 12 days after electroporation, 1G4 TCR-engineered T cells were harvested and co-cultured with JY target cells that had been loaded with various concentrations of NY-ESO-1 peptide (SLLMWITQC) ranging from 101 to 107 pg/mL. After co-culture for 4 hours, GolgiPlug protein transport inhibitor (cat #555028, BD Biosciences) was added, and cells were co-cultured for another 16 hours. Then, cells were harvested, permeabilized and FACS analyzed by co-staining with a PE anti-human IFN-γ antibody (clone 25723.11, cat #340452, BD Biosciences) and a FITC anti-human IL-2 antibody (clone 5344.111, cat #340448, BD Biosciences). All stainings were performed in BD Perm/ Wash Buffer (1×; cat #555028, BD Biosciences).

Figure 26B:
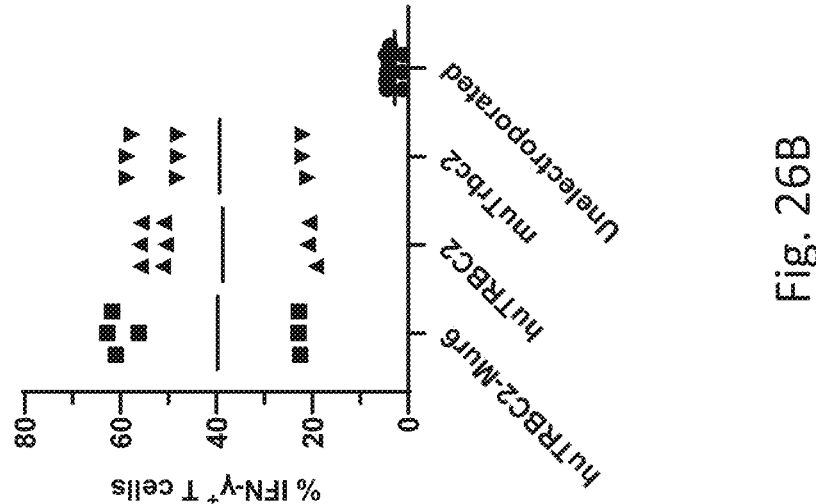
Figure 26D:
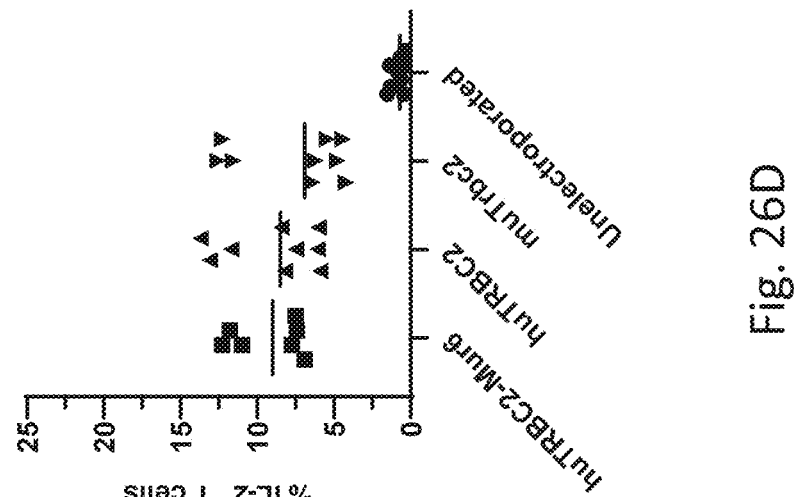

The results are represented in FIGS. 26A-26D: huTRBC2-Mur6 depicts a 1G4 TCR with human TRBC2 constant domain sequence with incorporation of 6 amino acid residues from the murine Trbc2 A strand, and FG loop (identified minimal H57 binding epitope); huTRBC2 depicts a 1G4 TCR with fully human TRBC2 constant domain sequence; muTrbc2 depicts a 1G4 TCR with fully murine Trbc2 constant domain sequence; Unelectroporated depicts unedited T cells. FIG. 26A shows the IFN-γ production in response to different peptide doses from T cells of 1 representative healthy donor (BC93). Symbols depict the geometric mean % IFN-γ+ T cells from 3 technical replicates per peptide dose; error bars depict the geometric standard deviation. FIG. 26B shows a summary of the IFN-γ production in response to the highest peptide dose tested (107 pg/mL) from T cells of 3 healthy donors. Symbols depict the % IFN-γ+ T cells from 3 technical replicates of each of the T cell donors; lines depict geometric means. FIG. 26C shows the IL-2 production in response to different peptide doses from T cells of 1 representative healthy donor (BC97). Symbols depict the geometric mean % IL-2+ T cells from 3 technical replicates per peptide dose; error bars depict the geometric standard deviation. FIG. 26D shows a summary of the IL-2 production in response to the highest peptide dose tested (107 pg/mL) from T cells of 3 healthy donors. Symbols depict the % IL-2+ T cells from 3 technical replicates of each of the T cell donors; lines depict geometric means. Together, these data show that 1G4 TCR-engineered T cells expressing a huTRBC2-Mur6 constant domain can mediate equivalent cytokine production to 1G4 TCR-engineered T cells expressing a huTRBC2 or muTrbc2 constant domain, indicating that incorporation of the Mur6 epitope into human TRBC2 does not impair TCR function.

EXAMPLE 11

This example shows that incorporation of 6 amino acid residues from the murine Trbc2 A strand and FG loop into the human TRBC2 sequence does not interfere with TCR function as measured by T cell target cell killing.

IncuCyte live-cell analysis was performed on human primary T cells with knock-in of the NY-ESO-1—specific 1G4 TCR at the endogenous TRAC locus using various DNA repair templates. Human primary CD3+ T cells from 3 healthy donors (BC20, BC93, and BC97) were selected and activated with anti-CD3/CD28 beads (cat #40203D, ThermoFisher Scientific) for 2 days and then electroporated with a TRAC RNP and with a DNA repair template to guide TCR knock-in, as well as with a TRBC RNP to guide endogenous TCRβ chain knock-out. 12 days after electroporation, 1G4 TCR-engineered T cells were harvested and co-cultured inside of an IncuCyte S3 live-cell analysis system (Sartorius) with NY-ESO-1+ A375-GFP+ tumor cells, with the number of live GFP+ tumor cells being quantified every 2 hours for a total of 72 hours.

Figure 27A:
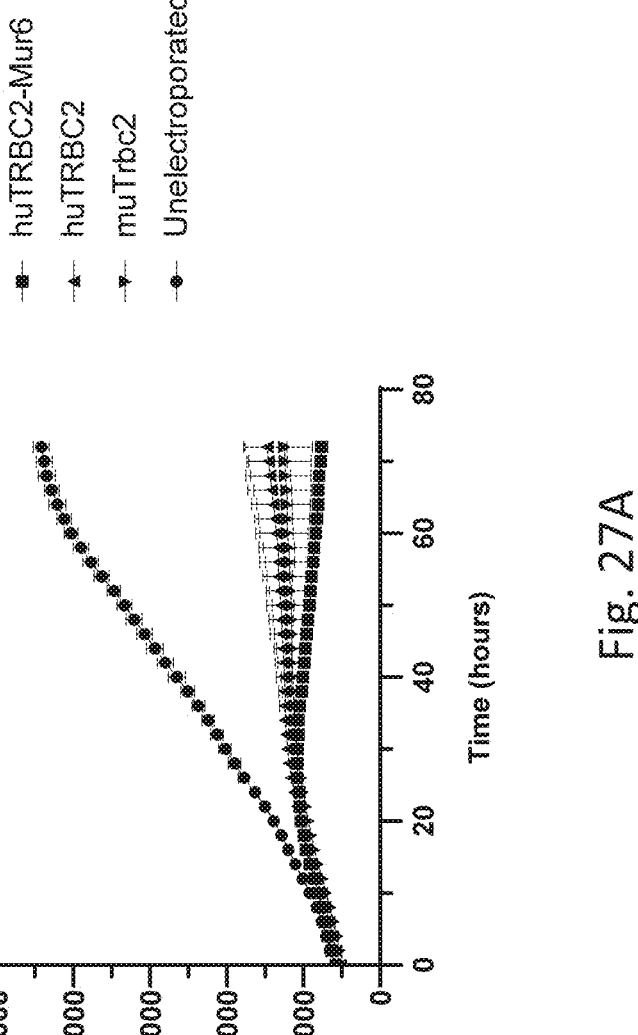
FIG. 27A shows the time-course of target cell number during co-culture with muTRBC2, huTRBC2, and huTRBC2-Mur6 1G4 TCR expressing T cells.
Figure 27B:
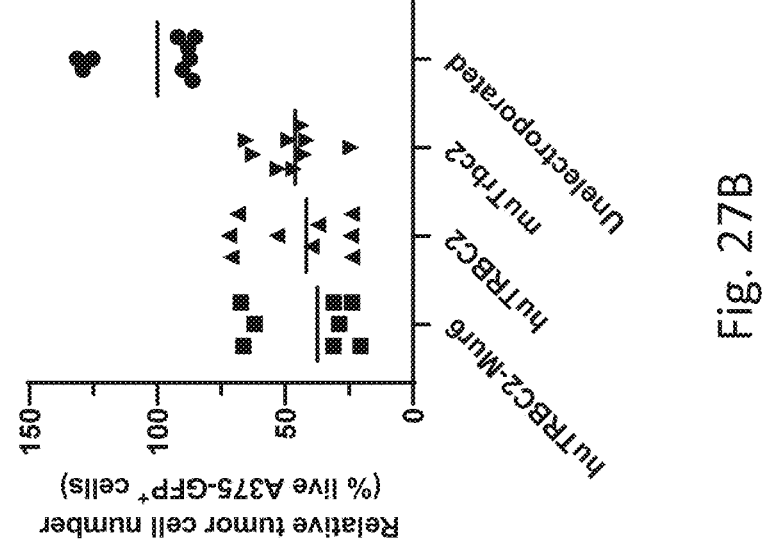
FIG. 27B shows a dot plot of the remaining relative cell number in individual experiments for the latest time point (72 hours).

The results are represented in FIGS. 27A and 27B: huTRBC2-Mur6 depicts a 1G4 TCR with human TRBC2 constant domain sequence with incorporation of 6 amino acid residues from the murine Trbc2 A strand, and FG loop (identified minimal H57 binding epitope); huTRBC2 depicts a 1G4 TCR with fully human TRBC2 constant domain sequence; muTrbc2 depicts a 1G4 TCR with fully murine Trbc2 constant domain sequence; Unelectroporated depicts unedited T cells. FIG. 27A shows the A375-GFP+ tumor cell killing kinetics by T cells from 1 representative healthy donor (BC97). Symbols depict the geometric mean live tumor cell number from 3 technical replicates per timepoint; error bars depict the geometric standard deviation. FIG. 27B shows a summary of the relative A375-GFP+ tumor cell killing at the final timepoint tested (72 hours) by T cells from 3 healthy donors. Symbols depict the live tumor cell number from 3 technical replicates of each of the T cell donors; lines depict geometric means. To calculate the relative tumor cell number, data were normalized to the geometric mean of the unelectroporated T cells, which was set at 100%. Together, these data show that 1G4 TCR-engineered T cells expressing a huTRBC2-Mur6 constant domain can mediate equivalent target cell killing to 1G4 TCR-engineered T cells expressing a huTRBC2 or muTrbc2 constant domain, indicating that incorporation of the Mur6 epitope into human TRBC2 does not impair TCR function.

What is claimed is:

1. A marked protein comprising:
a human TCR constant domain, wherein the TCR constant domain comprises a TCRα or TCRβ constant domain; and
an exogenous amino acid variation that comprises a sequence that is detectable and identifiable within the TCR constant domain, wherein the exogenous amino acid variation is from a non-human species, wherein the exogenous amino acid variation consists of 1 to 10 amino acid mutations, and wherein at least one of the mutations is in a FG loop.

2. The marked protein of claim 1, wherein the non-human species is a mouse.

3. The marked protein of claim 1, wherein the TCR constant domain comprises a sequence encoded by a human TRBC2 gene.

4. The marked protein of claim 1, wherein the exogenous amino acid variation comprises a sequence of a murine TCR Cβ domain.

5. The marked protein of claim 4, wherein the exogenous amino acid variation consists of 1, 2, 3, 4, 5, 6, 7, 8, 9, or 10 amino acid mutations selected from the group consisting of: K4R, F7T, Y37F, N106E, E108K, T110P, Q111E, D112G, R113S, and A114P, as numbered according to the numbering system of SEQ ID NO: 8.

6. The marked protein of claim 4, wherein the exogenous amino acid variation comprises 6 amino acid mutations.

7. The marked protein of claim 6, wherein the 6 amino acid mutations are: K4R, E108K, T110P, Q111E, D112G, and R113S, as numbered according to the numbering system of SEQ ID NO: 8.

8. The marked protein of claim 1, wherein the exogenous amino acid variation is detectable and identifiable by an antibody, a single-domain antibody, a Fab fragment or a designed ankyrin repeat protein.

9. The marked protein of claim 1, wherein the exogenous amino acid variation is detectable and identifiable by an anti-mouse TCR Cβ antibody H57-597.

10. A genetically engineered cell comprising the marked protein of claim 1.

11. The marked protein of claim 1, wherein the marked protein comprises huTRBC2-mur6 (SEQ ID NO: 27), huTRBC2-mur7 (SEQ ID NO: 26), huTRBC2-mur10 (SEQ ID NO: 15), or any one of SEQ ID NOs: 17-19 or 25.

12. The marked protein of claim 1, wherein the marked protein comprises huTRBC1-mur6 or huTRBC1-muFG (SEQ ID NO: 14).

13. The marked protein of claim 1, wherein the exogenous amino acid variation consists of 6, 7, 8, 9, or 10 amino acid mutations, wherein the marked protein comprises human TCRβC1 and the mutations are selected from the group consisting of: N4R, F7T, N106E, E108K, T110P, Q111E, D112G, R113S, and A114P, as numbered according to the numbering system of SEQ ID NO: 11, or wherein the marked protein comprises human TCRβC2 and the mutations are selected from the group consisting of: K4R, F7T, Y37F, N106E, E108K, T110P, Q111E, D112G, R113S, and A114P, as numbered according to the numbering system of SEQ ID NO: 8.

14. The marked protein of claim 13, wherein the marked protein comprises human TCRβC1 and the exogenous amino acid variation consists of N4R, E108K, T110P, Q111E, D112G, and R113S, as numbered according to the numbering system of SEQ ID NO: 11.

15. The marked protein of claim 13, wherein the exogenous amino acid variation consists of K4R, E108K, T110P, Q111E, D112G, and R113S, as numbered according to the numbering system of SEQ ID NO: 8.

16. The marked protein of claim 13, wherein the exogenous amino acid variation consists of K4R, E108K, T110P, Q111E, D112G, and R113S, and 1, 2, 3 or 4 additional mutations selected from the group consisting of: F7T, Y37F, N106E and A114P, as numbered according to the numbering system of SEQ ID NO: 8.

17. The marked protein of claim 13, wherein the exogenous amino acid variation consists of K4R, Y37F, E108K, T110P, Q111E, D112G, and R113S as numbered according to the numbering system of SEQ ID NO: 8.

18. The marked protein of claim 13, wherein the exogenous amino acid variation consists of K4R, F7T, Y37F, N106E, E108K, T110P, Q111E, D112G, and R113S, as numbered according to the numbering system of SEQ ID NO: 8.

19. The marked protein of claim 13, wherein the exogenous amino acid variation consists of K4R, Y37F, N106E, E108K, T110P, Q111E, D112G, R113S, and A114P as numbered according to the numbering system of SEQ ID NO: 8.

20. The marked protein of claim 13, wherein the exogenous amino acid variation consists of K4R, F7T, N106E, E108K, T110P, Q111E, D112G, R113S, and A114P as numbered according to the numbering system of SEQ ID NO: 8.

21. The marked protein of claim 13, wherein the exogenous amino acid variation consists of K4R, F7T, Y37F, E108K, T110P, Q111E, D112G, R113S, and A114P as numbered according to the numbering system of SEQ ID NO: 8.

22. The marked protein of claim 13, wherein the exogenous amino acid variation consists of K4R, F7T, Y37F, N106E, E108K, T110P, Q111E, D112G, R113S, and A114P as numbered according to the numbering system of SEQ ID NO: 8.

* * * * *